(12) United States Patent
Yang et al.

(10) Patent No.: US 8,299,067 B2
(45) Date of Patent: Oct. 30, 2012

(54) 5-DEMETHOXYFUMAGILLOL AND DERIVATIVES THEREOF

(75) Inventors: Dan Yang, Hong Kong (HK); Chengyong Li, Jiaxing (CN); Shiwu Chen, Lanzhou (CN)

(73) Assignees: Versitech Limited, Hong Kong (CN); Morningside Ventures Limited, Hong Kong (CN)

( * ) Notice: Subject to any disclaimer, the term of this patent is extended or adjusted under 35 U.S.C. 154(b) by 683 days.

(21) Appl. No.: 12/410,473

(22) Filed: Mar. 25, 2009

(65) Prior Publication Data

US 2009/0247503 A1    Oct. 1, 2009

Related U.S. Application Data

(60) Provisional application No. 61/039,798, filed on Mar. 27, 2008.

(51) Int. Cl.
| | |
|---|---|
| *A61K 31/535* | (2006.01) |
| *A61K 31/497* | (2006.01) |
| *A61K 31/445* | (2006.01) |
| *C07D 413/00* | (2006.01) |
| *C07D 405/00* | (2006.01) |
| *C07D 401/00* | (2006.01) |
| *C07D 205/00* | (2006.01) |
| *C07D 303/00* | (2006.01) |

(52) U.S. Cl. .......... 514/231.5; 514/254.1; 514/326; 544/147; 544/374; 546/207; 548/517; 548/950; 549/332

(58) Field of Classification Search .......... 544/122, 544/336, 147, 374; 546/207; 548/517, 950; 514/231.5, 254.1, 326; 549/332
See application file for complete search history.

(56) References Cited

U.S. PATENT DOCUMENTS 6,040,337 A * 3/2000 Hong et al. .......... 514/475

\* cited by examiner

*Primary Examiner* — Taylor Victor Oh
(74) *Attorney, Agent, or Firm* — Saliwanchick, Lloyd & Eisenschenk

(57) ABSTRACT

Provided herein are 5-demethoxyfumagillol and its derivatives. Also provided herein are methods of making the 5-demethoxyfumagillol and derivatives. Also provided herein are biological activities of the 5-demethoxyfumagillol and derivatives and methods of using same for treating diseases.

12 Claims, 2 Drawing Sheets

Control bFGF bFGF+17j bFGF+17n bFGF+17q

5-DEMETHOXYFUMAGILLOL AND DERIVATIVES THEREOF

PRIOR RELATED APPLICATIONS

This application claims priority to U.S. Provisional Patent Application Ser. No. 61/039,798, filed Mar. 27, 2008, which is incorporated herein by reference in its entirety.

FIELD

Provided herein are 5-demethoxyfumagillol and its derivatives. Also provided herein are methods of making the 5-demethoxyfumagillol and derivatives. Also provided herein are biological activities of the 5-demethoxyfumagillol derivatives and methods of using same for treating diseases.

BACKGROUND

Angiogenesis refers to the physiological process involving the formation or growth of new blood vessels from pre-existing vessels. Angiogenesis may be generally controlled by certain chemicals produced in the body. Some of these chemicals stimulate cells to repair damaged blood vessels or form new ones. Other chemicals, such as angiogenesis inhibitors, signal the process to stop.

Therapeutic angiogenesis is the application of specific compounds which may inhibit or induce the creation of new blood vessels in the body in order to combat diseases. The therapeutic application of the principle "angiogenesis" can be divided into two main areas, i.e., anti-angiogenic therapies and pro-angiogenic therapies. The pro-angiogenic therapies generally involves inducing the creation of new blood vessels for treating or preventing cardiovascular diseases, atherosclerotic diseases and related diseases such as coronary heart disease, peripheral arterial disease and wound healing disorders. On the contrary, the anti-angiogenic therapies generally involves inhibiting the creation of new blood vessels for treating cancers, tumors and malignancies.

Angiogenesis can play an important role in the growth and spread of cancer, tumor and malignancy. For example, new blood vessels can feed the cancer or tumor cells with oxygen and nutrients, allow these cells to grow, invade nearby tissue, spread to other parts of the body, and form new colonies of cancer cells.

Angiogenesis inhibitors or antiangiogenic agents, such as fumagillin and derivatives thereof, are expected to be of great clinical potential in treating many diseases, such as solid tumors, diabetic retinopathy, rheumatoid arthritis, psoriasis and obesity (Folkman, J. *Nat. Med.* 1995, 1, 27). Recent clinical studies showed that when given in combination with chemotherapies, some antiangiogenic agents produced much better responses (Jain, R. K. *Science* 2005, 307, 58 and references therein) than chemotherapies alone. It is also reported that fumagillin may be used to treat intestinal infections, such as intestinal microsporidiosis or amebiasis.

Among antiangiogenic agents, fumagillin and its natural or synthetic derivatives, have received close attention because of their biological activities. For example, 5-demethoxyfumagillol is a potent angiogenesis inhibitor isolated in 2004 from *Aspergillus fumigatus* by D. Kim et al. The structure of 5-demethoxyfumagillol was confirmed by an independent synthesis from fumagillol (Kim, D.; Min, J.; Ahn, S. K.; Lee, H. W.; Choi, N. S.; Moon, S. K. *Chem. Pharm. Bull.* 2004, 52, 447). The X-ray structure of a MetAP-2-fumagillin complex (Liu, S.; Widom, J.; Kemp, C. W.; Crews, C. M.; Clardy, J. *Science* 1998, 282, 1324) suggests that generally fumagillin-related compounds selectively and irreversibly inhibit the cobalt-containing type II methionine aminopeptidase (MetAP-2) in the same manner as fumagillin.

The suggested mechanism has been directing the drug design of fumagillin and related natural product derivatives based on such structure-activity relation. For example, TNP-470, a fumagillin derivative, can effectively block tumor growth and metastasis in animal models, and showed promise in phase I/II clinical trials. However, further clinical trials of TNP-470 was stymied by its low half-life values, neurotoxic side effects (fatigue, vertigo, ataxia and loss of concentration) and possible disruption of normal angiogenic process (femal reproductive system, wound healing). Such undesirable properties and side effects generally limit the widespread use of TNP-470 as an anticancer agent ((a) Kruger, E. A.; Figg, W. D. *Expert Opin. Invest. Drugs* 2000, 9, 1383; (b) Griffith, E. C.; Su, Z.; Turk, B. E.; Chen, S.; Chang, Y.-H.; Wu, Z.; Biemann, K.; Liu, J. O. *Chem. Biol.* 1997, 4, 461).

Recently, fumagillin derivatives PPI-2458 (Bernier, S. G.; Lazarus, D. D.; Clark, E.; Doyle, B.; Labenski, M. T.; Thompson, C. D.; Westlin, W. F.; Hannig G. *Proc. Natl. Acad. Sci. U.S.A.* 2004, 101, 10768) and CKD-732 (Kim, E.-J.; Shin, W.-H. *Biol. Pharm. Bull* 2005, 28, 217) have entered into phase I clinical trials in cancer and other diseases. However, both PPI-2458 and CKD-732 have rather complicated structures.

Thus there is a need for further fumagillin derivatives for treating cancer and other diseases. Further, there is a need for angiogenesis inhibitors that are easier to prepare and/or have no or reduced undesirable properties and/or side effects.

SUMMARY

Provided herein are multi-step processes of making 5-demethoxyfumagillol and derivatives thereof from readily available starting materials wherein the processes include a catalytic stereoselective ene cyclization step. In some embodiments, the multi-step processes include using a chiral Lewis acid to catalyze an enantioselective intramolecular carbonyl ene reaction of unsaturated α-keto esters. In other embodiments, derivatives of 5-demethoxyfumagillol are synthesized according to the processes disclosed herein and have been found to be potent angiogenesis inhibitors or antiangiogenic agents.

In one aspect, provided herein are unsaturated α-keto esters comprising Formula (I):

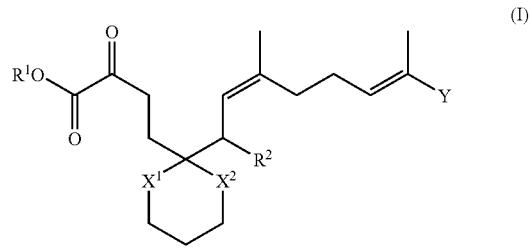

or a stereoisomer thereof, wherein $R^1$ is tosyl, mesyl, triflyl or nonflyl, or unsubstituted or substituted aryl, alkyl, alkenyl or alkynyl; $R^2$ is hydrogen or $OR^3$ where $R^3$ is alkyl, acyl (e.g., acetyl and benzoyl), aryl, arylalkyl (e.g., benzyl), alkylaryl (e.g., methylphenyl); each of $X^1$ and $X^2$ is independently O or S; and Y is $-CH_2-R^4$, $-CH_2-OR^5$, $-C(=O)-R^6$ or $-C(=O)-OR^7$ where each of $R^4$, $R^5$, $R^6$ and $R^7$ is independently H, alkyl, acyl, aryl, arylalkyl, alkylaryl, trialkylsilyl, methoxymethyl, dialkylamino, diarylamino or alkylarylamino.

In some embodiments, the stereoisomer is an enantiomer.

In another aspect, provided herein are processes of making an unsaturated α-keto ester of Formula (I):

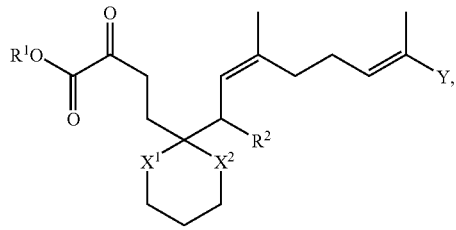

(I)

wherein the process comprises the steps of:
(a) contacting an ester of Formula (II):

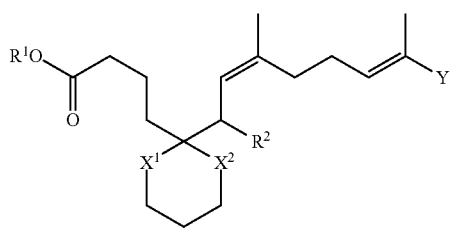

(II)

or a stereoisomer thereof with a base and a peroxide to form an unsaturated α-hydroxyl ester of Formula (III):

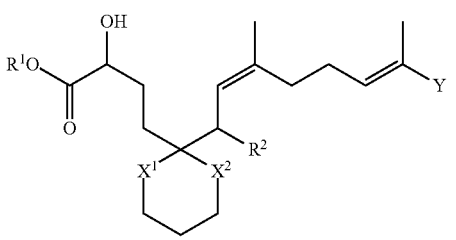

(III)

or a stereoisomer thereof, and
(b) oxidizing the unsaturated α-hydroxyl ester of Formula (III) or a stereoisomer thereof with an oxidant to form the unsaturated α-keto ester of Formula (I), wherein $R^1$, $R^2$, $X^1$, $X^2$ and Y are as defined herein.

In some embodiments, the base is an organolithium reagent such as lithium diisopropylamide (LDA), lithium bis(trimethylsilyl)amide (LiHMDS), lithium hexamethyldisilazide (LiHMDS), methyllithium, butyllithium, hexyllithium, sec-butyllithium, and phenyllithium; an organopotassium reagent such as potassium bis(trimethylsilyl)amide (KHMDS); or an organosodium reagent such as sodium bis(trimethylsilyl)amide (NaHMDS).

In certain embodiments, the peroxide is t-BuOOH. In other embodiments, the oxidant is Dess-Martin periodinane.

In another aspect, provided herein are processes of making an unsaturated α-hydroxyl ester of Formula (III):

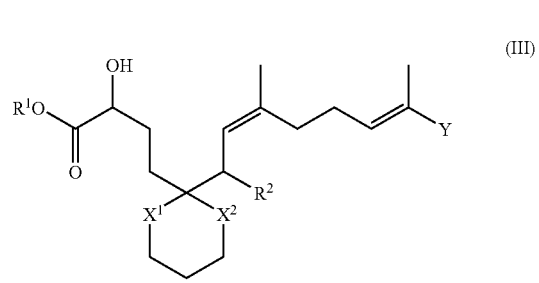

(III)

or a stereoisomer thereof,
wherein the process comprises the steps of:
(a) contacting an aldehyde of Formula (IV):

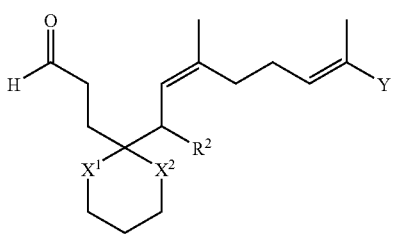

(IV)

or a stereoisomer thereof
with a mixture of isocyanate and $SiCl_4$ in the presence of a catalytic amount of pyridine N-oxide or hexamethylphosphoramide (HMPA); and
(b) quenching the reaction mixture with an alcohol having a formula represented by $R^1OH$ and sodium bicarbonate, wherein $R^1$, $R^2$, $X^1$, $X^2$ and Y are as defined herein.

In another aspect, provided herein is a 5-demethoxyfumagillol intermediate comprising Formula (V):

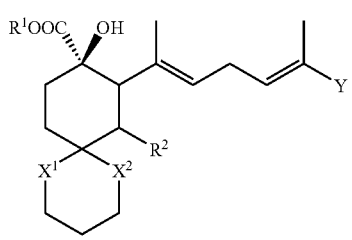

(V)

or a stereoisomer thereof,
wherein $R^1$, $R^2$, $X^1$, $X^2$ and Y are as defined herein.

In some embodiments, the stereoisomer is an enantiomer of Formula (V). In some embodiments, the stereoisomer is a diastereomer of Formula (V).

In another aspect, provided herein are processes of making a 5-demethoxyfumagillol intermediate having formula (V):

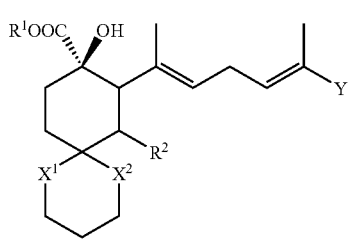

(V)

or a stereoisomer thereof,
wherein the process comprises the step of contacting the unsaturated α-keto ester of Formula (I) with a Lewis acid, and wherein $R^1$, $R^2$, $X^1$, $X^2$ and Y are as defined herein.

In some embodiments, the Lewis acid is copper triflate (Cu(OTf)$_2$), copper hexafluoroantimonate (Cu(SbF$_6$)$_2$), scandium(III) trifluoromethanesulfonate (Sc(OTf)$_3$), ytterbium trifluoromethanesulfonate (Yb(OTf)$_3$), magnesium perchlorate (Mg(ClO$_4$)$_2$) or a combination thereof.

In certain embodiments, the reaction occurs in the presence of a chiral ligand. In other embodiments, the chiral ligand is a bisoxazoline ligand. In further embodiments, the bisoxazoline ligand is (S,S)-2,2-bis(4-phenyl-2-oxazolin-2-yl)propane ((S,S)-Ph-BOX; CAS 131457-46-0), (R,R)-2,2-bis(4-phenyl-2-oxazolin-2-yl)propane ((R,R)-Ph-BOX; CAS 150529-93-4), (S,S)-2,2'-bis(4-tert-butyl-2-oxazoline)propane ((S,S)-tBu-BOX; CAS 132098-54-5), (R,R)-2,2'-bis(4-tert-butyl-2-oxazoline)propane ((R,R)-tBu-BOX; CAS 150529-93-4), 2,6-bis[(4S)-4-isopropyl-2-oxazolinyl]pyridine ((4S)-iPr-PyBOX; CAS 118949-61-4), 2,6-bis[(4R)-4-isopropyl-2-oxazolinyl]pyridine ((4R)-iPr-PyBOX; CAS 131864-67-0), 2,6-bis[(4S)-4-phenyl-2-oxazolinyl]pyridine ((4S)-Ph-PyBOX; CAS 174500-20-0), 2,6-bis[(4R)-4-phenyl-2-oxazolinyl]pyridine ((4R)-Ph-PyBOX; CAS 128249-70-7) or a combination thereof.

In another aspect, provided herein is an unsaturated alcohol having Formula (VI):

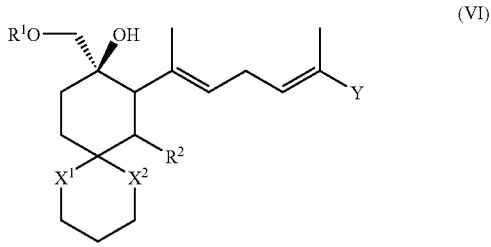

(VI)

or a stereoisomer thereof,
wherein R$^1$ is tosyl, mesyl, triflyl or nonflyl, or unsubstituted or substituted aryl, alkyl, alkenyl or alkynyl; R$^2$ is hydrogen or OR$^3$ where R$^3$ is H, alkyl, acyl, aryl, arylalkyl or alkylaryl; each of X$^1$ and X$^2$ is independently O or S; and Y is —CH$_2$—R$^4$, —CH$_2$—OR$^5$, —C(=O)—R$^6$ or —C(=O)—OR$^7$ where each of R$^4$, R$^5$, R$^6$ and R$^7$ is independently H, alkyl, acyl, aryl, arylalkyl, alkylaryl, trialkylsilyl, methoxymethyl, dialkylamino, diarylamino or alkylarylamino.

In another aspect, provided herein are processes of making an unsaturated alcohol, i.e., a 5-demethoxyfumagillol intermediate, having formula (VI):

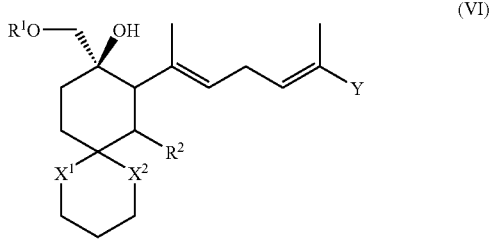

(VI)

or a stereoisomer thereof,
wherein the processes comprise the steps of:
(a) contacting an unsaturated ester of Formula (V) with lithium aluminium hydride (LiAlH$_4$) or diisobutylaluminium hydride (DIBAL-H) to form an unsaturated diol of Formula (VII),

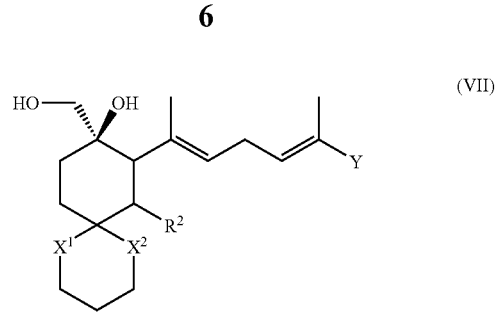

(VII)

or a stereoisomer thereof, and (b) selectively protecting the unsaturated diol of Formula (VII) or a stereoisomer thereof with a tosylate, halide, mesylate or triflate to form the unsaturated ester of Formula (VI), wherein R$^1$ is tosyl, mesyl, triflyl or nonflyl, or unsubstituted or substituted aryl, alkyl, alkenyl or alkynyl; R$^2$ is hydrogen or OR$^3$ where R$^3$ is H, alkyl, acyl, aryl, arylalkyl, alkylaryl; each of X$^1$ and X$^2$ is independently O or S; and Y is —CH$_2$—R$^4$, —CH$_2$—OR$^5$, —C(=O)—R$^6$ or —C(=O)—OR$^7$ where each of R$^4$, R$^5$, R$^6$ and R$^7$ is independently H, alkyl, acyl, aryl, arylalkyl, alkylaryl, trialkylsilyl, methoxymethyl, dialkylamino, diarylamino or alkylarylamino.

In some embodiments, the halide is chloride, bromide or iodide.

In another aspect, provided herein are keto epoxides comprising Formula (VIII):

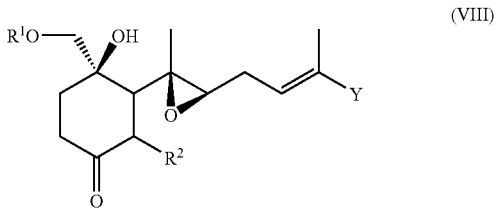

(VIII)

or a stereoisomer thereof,
wherein R$^1$, R$^2$, and Y are as defined herein.

In some embodiments, the stereoisomer is an enantiomer of Formula (VIII). In other embodiments, the stereoisomer is a diastereomer of Formula (VIII).

In another aspect, provided herein are processes of making a keto epoxide, i.e., a 5-demethoxyfumagillol intermediate, having formula (VIII):

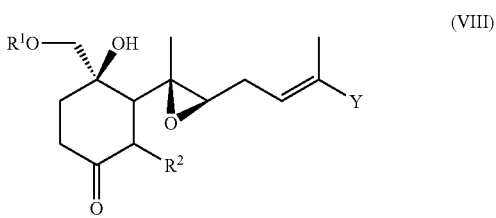

(VIII)

or a stereoisomer thereof,
wherein the process comprises the step of contacting an unsaturated ketone of Formula (IX):

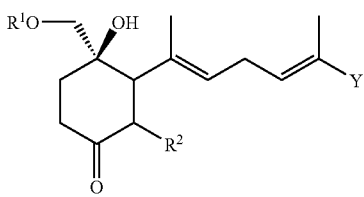

(IX)

or a stereoisomer thereof, with an epoxidation agent in the presence or absence of 4 Å molecular sieves, wherein $R^1$ is tosyl, mesyl, triflyl or nonflyl; $R^2$ is hydrogen or $OR^3$ where $R^3$ is H, alkyl, acyl, aryl, arylalkyl or alkylaryl; and Y is —$CH_2$—$R^4$, —$CH_2$—$OR^5$, —C(=O)—$R^6$ or —C(=O)—$OR^7$ where each of $R^4$, $R^5$, $R^6$ and $R^7$ is independently H, alkyl, acyl, aryl, arylalkyl, alkylaryl, trialkylsilyl, methoxymethyl, dialkylamino, diarylamino or alkylarylamino.

In some embodiments, the contacting step occurs in the presence of 4 Å molecular sieves. In other embodiments, the epoxidation agent is tert-butyl hydroperoxide with titanium isopropoxide or vanadyl acetylacetonate.

In another aspect, provided herein are 5-demethoxyfumagillol derivatives comprising Formula (X), (X'), (X''), (XI) or (XI'):

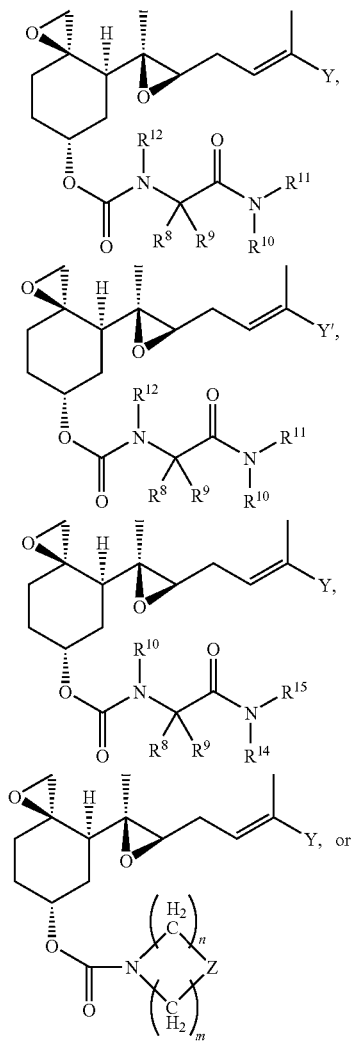

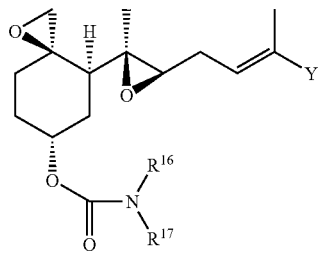

(XI')

or a pharmaceutically acceptable salt, solvate, polymorph or stereoisomer thereof, wherein each of $R^8$, $R^9$, $R^{10}$, $R^{11}$, $R^{12}$, $R^{13}$, $R^{16}$ and $R^{17}$ is independently hydrogen or unsubstituted or substituted aryl such as phenyl, 4-nitrophenyl and 4-fluorophenyl; alkyl such as methyl, ethyl and 2-hydroxyethyl; cycloalkyl such as cyclopropyl and cyclopentyl; alkenyl such as vinyl and allyl; alkynyl such as prop-2-ynyl; arylalkyl; alkylaryl; heterocycloalkyl such as azacyclohexane; heteroaryl such as thiazolyl; or —$(CH_2)_k$—$N_3$; Z is a bond, methylene, O, S or $NR^{13}$; Y is —$CH_2$—$R^4$, —$CH_2$—$OR^5$, —C(=O)—$R^6$ or —C(=O)—$OR^7$; Y' is —$CH_2$—$R^{4'}$, —$CH_2$—$OR^5$, —C(=O)—$R^6$ or —C(=O)—$OR^7$ where each of $R^4$, $R^5$, $R^6$ and $R^7$ is independently H, alkyl, aryl, arylalkyl, alkylaryl, trialkylsilyl, methoxymethyl, dialkylamino, diarylamino or alkylarylamino; $R^{4'}$ is alkyl, acyl, aryl, arylalkyl, alkylaryl, trialkylsilyl, methoxymethyl, dialkylamino, diarylamino or alkylarylamino; each of $R^{14}$ and $R^{15}$ is independently H, unsubstituted or substituted aryl, heteroaryl, cycloalkyl such as cyclopropyl and cyclopentyl, alkenyl such as vinyl and allyl, alkynyl such as prop-2-ynyl, arylalkyl, alkylaryl, or —$(CH_2)_k$—$N_3$; each of n and m is independently an integer from 0 to 9 where the sum of n and m is at least one; and k is an integer from 1 to 10, with the proviso that $R^{14}$ and $R^{15}$ are not both H. In some embodiments, $R^{16}$ and $R^{17}$ are not both H.

In some embodiments, the stereoisomer is an enantiomer of Formula (X) or (XI). In other embodiments, the stereoisomer is a diastereomer of Formula (X) or (XI).

In another aspect, provided herein are processes of making a 5-demethoxyfumagillol derivative having formula (X) or (XI):

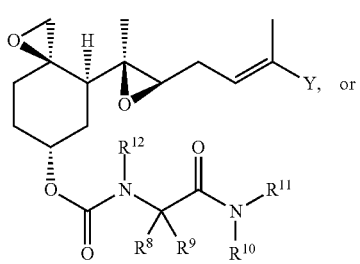

(X)

-continued

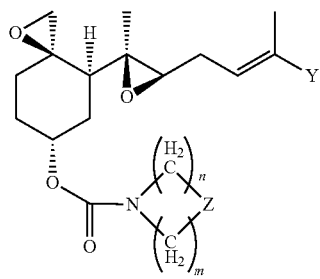
(XI)

or a stereoisomer thereof, wherein the processes comprise the steps of:

(a) reacting a keto epoxide comprising Formula (VIII):

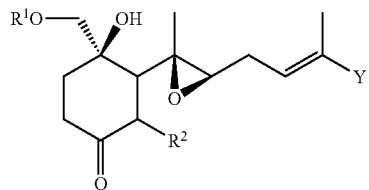
(VIII)

or a stereoisomer thereof, with a base to form 5-demethoxyfumagillol of Formula (XII):

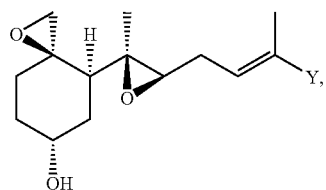
(XII)

or a stereoisomer thereof, (b) contacting the 5-demethoxyfumagillol of Formula (XII) or a stereoisomer thereof with a phenylchloroformate in the presence of a first base to form an active intermediate of Formula (XIII),

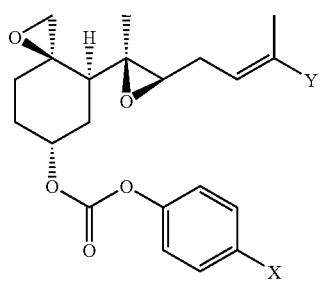
(XIII)

or a stereoisomer thereof, and (c) reacting the active intermediate of Formula (XIII) with an amine of Formula (XIV) or Formula (XV):

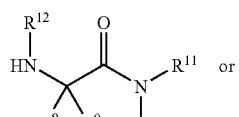
(XIV)

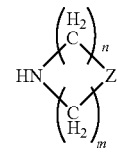
(XV)

or stereoisomer thereof in the presence of a second base, wherein $R^1$ is tosyl, mesyl, triflyl or nonflyl; X is $NO_2$ or hydrogen; each of $R^8$, $R^9$, $R^{10}$, $R^{11}$ and $R^{12}$ is independently hydrogen, unsubstituted or substituted aryl, alkyl, cycloalkyl such as cyclopropyl and cyclopentyl, alkenyl such as vinyl and allyl, alkynyl such as prop-2-ynyl, arylalkyl, alkylaryl, heterocycloalkyl, heteroaryl, or $-(CH_2)_k-N_3$; Z is two hydrogens, two OH groups, methylene, O, S or $NR^{13}$; Y is $-CH_2-R^4$, $-CH_2-OR^5$, $-C(=O)-R^6$ or $-C(=O)-OR^7$ where each of $R^4$, $R^6$, $R^7$ and $R^{13}$ is independently H, alkyl, acyl, aryl, arylalkyl, alkylaryl, trialkylsilyl, methoxymethyl, dialkylamino, diarylamino or alkylarylamino; and each of n and m is independently an integer from 0 to 9 and the sum of n and m is at least one.

In some embodiments, the each of the first base and the second base is independently an organic base such as pyridine or triethylamine. In certain embodiments, the phenylchloroformate is unsubstituted phenylchloroformate or p-nitrophenylchloroformate.

In another aspect, provided herein are methods of treating, managing or preventing a disease that is related to angiogenesis, the method comprising administering a 5-demethoxyfumagillol derivative of disclosed herein, or a pharmaceutically acceptable salt, solvate, polymorph or stereoisomer thereof.

In some embodiments, the disease is a cancer or tumor. In further embodiments, the cancer is prostate cancer, lung cancer, colorectal cancer, bladder cancer, pancreatic cancer, endometrial cancer, ovarian cancer, cutaneous melanoma, leukemia, non-Hodgkin lymphoma or pancreatic cancer.

In another aspect, provided herein are methods of treating, managing or preventing a disease comprising administering a 5-demethoxyfumagillol derivative disclosed herein, or a pharmaceutically acceptable salt, solvate, polymorph or stereoisomer thereof, wherein the disease is a cancer, tumor, diabetic retinopathy, rheumatoid arthritis, psoriasis, obesity, chronic kidney disease or intestinal infection.

In some embodiments, the disease is an intestinal infection selected from intestinal microsporidiosis, taeniasis solium, cysticercosis, amebiasis, anisakiasis, giardiasis, or cryptosporidiosis.

In certain embodiments, the disease occurs in a mammal. In further embodiments, the mammal is a human.

In another aspect, provided herein are pharmaceutical compositions comprising a 5-demethoxyfumagillol derivative disclosed herein, or a pharmaceutically acceptable salt, solvate, polymorph or stereoisomer thereof, and a pharmaceutically acceptable carrier.

In some embodiments, the pharmaceutical composition disclosed herein further comprise at least an ingredient selected from the group consisting of excipients, moisturizers, diluents, metal stearates and combinations thereof. In further embodiments, the pharmaceutical composition disclosed herein is in a single unit dosage form.

In certain embodiments, the pharmaceutical composition disclosed herein further comprises a second chemotherapeutic drug. In further embodiments, the second chemotherapeutic drug is selected from the group consisting of alkylating agents, anti-metabolites, plant alkaloids and terpenoids, vinca alkaloids, podophyllotoxins, taxanes, topoisomerase inhibitors, antitumour antibiotics, and monoclonal antibodies and combinations thereof. dr

DEFINITIONS

Figure 1:
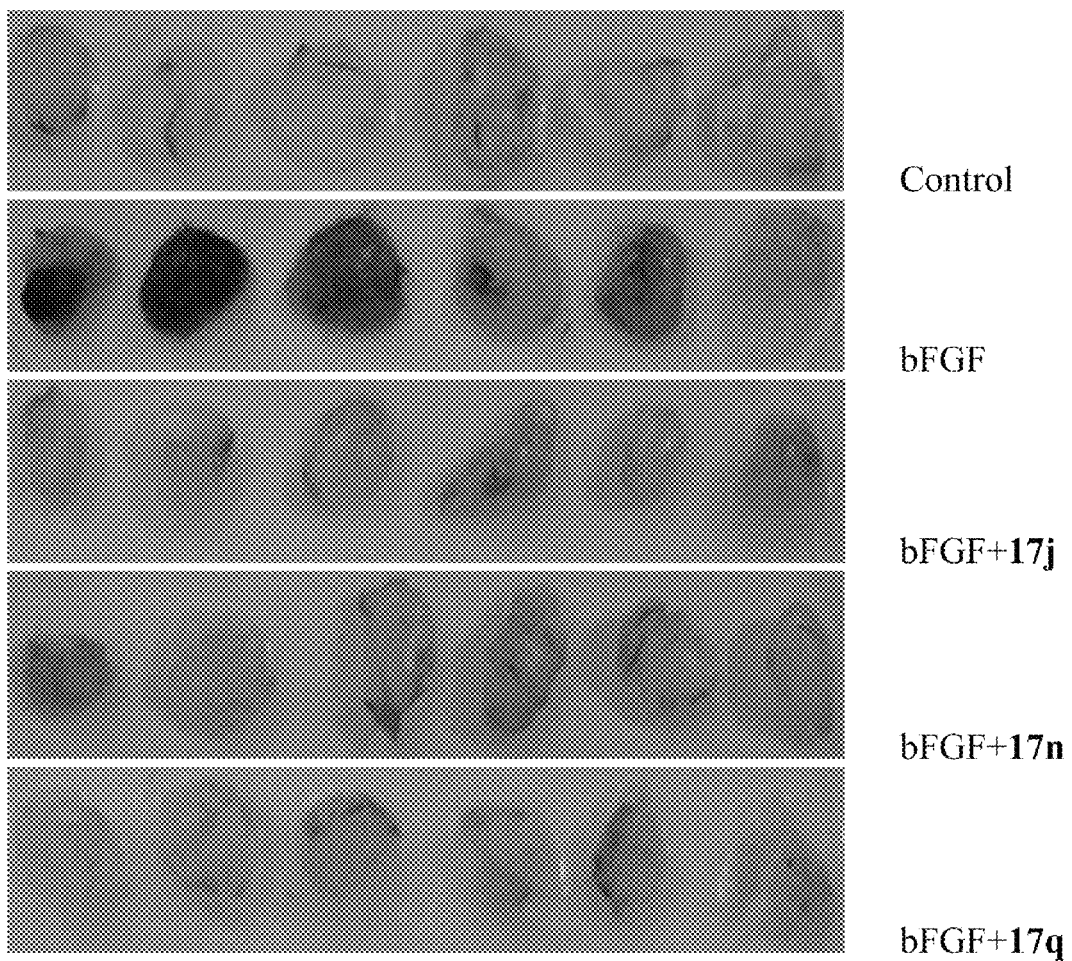
FIG. 1 depicts matrigel plugs taken from mice 10 days after injection of matrigel containing bFGF with or without Compound 17j, 17n or 17q.

To facilitate the understanding of the subject matter disclosed herein, a number of terms, abbreviations or other shorthand as used herein are defined below. Any term, abbreviation or shorthand not defined is understood to have the ordinary meaning used by a skilled artisan contemporaneous with the submission of this application.

"Amino" refers to a primary, secondary, or tertiary amine which may be optionally substituted. Specifically included are secondary or tertiary amine nitrogen atoms which are members of a heterocyclic ring. Also specifically included, for example, are secondary or tertiary amino groups substituted by an acyl moiety. Some non-limiting examples of amino group include —$NR^{13}R^{14}$ wherein each of $R^{13}$ and $R^{14}$ is independently H, alkyl, aryl, aralkyl, alkaryl, cycloalkyl, acyl, heteroalkyl, heteroaryl or heterocycyl.

"Alkyl" refers to a fully saturated acyclic monovalent radical containing carbon and hydrogen, and which may be branched or a straight chain. In some embodiments, alkyl contains from about 1 to about 25 carbon atoms. Examples of alkyl groups are methyl, ethyl, n-propyl, isopropyl, n-butyl, t-butyl, n-heptyl, n-hexyl, n-octyl, and n-decyl. "Lower alkyl" refers to an alkyl radical of one to six carbon atoms, as exemplified by methyl, ethyl, n-butyl, i-butyl, t-butyl, isoamyl, n-pentyl, and isopentyl.

"Alkenyl" or "alkenylene" respectively refers to a monovalent or divalent hydrocarbyl radical which has at least one double bond. The alkenyl or alkenylene group may be cyclic, branched acyclic or straight acyclic. In some embodiments, the alkenyl or alkenylene group contains only one double bond. In other embodiments, the alkenyl or alkenylene group contains two or more double bonds. In further embodiments, the alkenyl or alkenylene group can be a lower alkenyl or alkenylene containing from two to eight carbon atoms in the principal chain. In further embodiments, the alkenyl or alkenylene group can have one double bond and up to 25 carbon atoms, as exemplified by ethenyl, propenyl, isopropenyl, butenyl, isobutenyl, hexenyl, and the like.

"Alkynyl" or "alkynylene" respectively refers to a monovalent or divalent hydrocarbyl radical which has at least a triple bond. In some embodiments, the alkynyl or alkynylene group contains only one triple bond. In other embodiments, the alkynyl or alkynylene group contains two or more triple bonds. In further embodiments, the alkynyl or alkynylene group can be a lower alkynyl or alkynylene containing from two to eight carbon atoms in the principal chain. In further embodiments, the alkynyl or alkynylene group can have one triple bond and up to 20 carbon atoms, as exemplified by ethynyl, propynyl, isopropynyl, butynyl, isobutynyl, hexynyl, and the like.

"Aromatic" or "aromatic group" refers to aryl or heteroaryl.

"Aryl" refers to optionally substituted carbocyclic aromatic groups. In some embodiments, the aryl group includes a monocyclic or bicyclic group containing from 6 to 12 carbon atoms in the ring portion, such as phenyl, biphenyl, naphthyl, substituted phenyl, substituted biphenyl or substituted naphthyl. In other embodiments, the aryl group is phenyl or substituted phenyl.

"Arylalkyl" refers to an alkyl group which is substituted with an aryl group. Some non-limiting examples of aralkyl include benzyl and phenethyl.

"Alkylaryl" refers to an aryl group which is substituted with an alkyl group. Some non-limiting examples of alkaryl include methylphenyl and methylnaphthyl.

"Acyl" refers to a monovalent group of the formula —C(=O)H, —C(=O)-alkyl, —C(=O)-aryl, —C(=O)-aralkyl, or —C(=O)-alkaryl.

"Halogen" or "halo" refers to fluorine, chlorine, bromine and iodine.

"Heteroatom" refers to atoms other than carbon and hydrogen.

"Substituted" as used herein to describe a compound or chemical moiety refers to that at least one hydrogen atom of that compound or chemical moiety is replaced with a second chemical moiety. Non-limiting examples of substituents are those found in the exemplary compounds and embodiments disclosed herein, as well as halogen; alkyl; heteroalkyl; alkenyl; alkynyl; aryl, heteroaryl, hydroxy; alkoxyl; amino; nitro; thiol; thioether; imine; cyano; amido; phosphonato; phosphine; carboxyl; thiocarbonyl; sulfonyl; sulfonamide; ketone; aldehyde; ester; oxo; haloalkyl (e.g., trifluoromethyl); carbocyclic cycloalkyl, which can be monocyclic or fused or non-fused polycyclic (e.g., cyclopropyl, cyclobutyl, cyclopentyl or cyclohexyl) or a heterocycloalkyl, which can be monocyclic or fused or non-fused polycyclic (e.g., pyrrolidinyl, piperidinyl, piperazinyl, morpholinyl or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl or benzofuranyl); amino (primary, secondary or tertiary); o-lower alkyl; o-aryl, aryl; aryl-lower alkyl; —$CO_2CH_3$; —$CONH_2$; —$OCH_2CONH_2$; —$NH_2$; —$SO_2NH_2$; —$OCHF_2$; —$CF_3$; —$OCF_3$; —NH(alkyl); —N(alkyl)$_2$; —NH(aryl); —N(alkyl)(aryl); —N(aryl)$_2$; —CHO; —CO(alkyl); —CO(aryl); —$CO_2$(alkyl); and —$CO_2$(aryl); and such moieties can also be optionally substituted by a fused-ring structure or bridge, for example —$OCH_2O$—. These substituents can optionally be further substituted with a substituent selected from such groups. All chemical groups disclosed herein can be substituted, unless it is specified otherwise. For example, "substituted" alkyl, alkenyl, alkynyl, aryl, hydrocarbyl or heterocyclo moieties described herein are moieties which are substituted with a hydrocarbyl moiety, a substituted hydrocarbyl moiety, a heteroatom, or a heterocyclo. Further, substituents may include moieties in which a carbon atom is substituted with a heteroatom such as nitrogen, oxygen, silicon, phosphorus, boron, sulfur, or a halogen atom. These substituents may include halogen, heterocyclo, alkoxy, alkenoxy, alkynoxy, aryloxy, hydroxy, protected hydroxy, keto, acyl, acyloxy, nitro, amino, amido, cyano, thiol, ketals, acetals, esters and ethers.

"Hydroxy activating group" refers to a labile chemical moiety which is known in the art to activate a hydroxyl group during an activation reaction such as in a substitution reaction. For example, the hydroxy activating group —OB can be activated to form —OH by substituting the B group with a hydrogen. In some embodiments, B is methanesulfonyl (mesyl), p-toluenesulfonyl (tosyl), trifluoromethanesulfonyl (triflyl), nonafluorobutanesulfonyl (nonflyl) or 3-nitrobenzenesulfonyl. Some non-limiting examples of hydroxyl activating group include methanesulfonate (mesylate), p-toluenesulfonate (tosylate), trifluoromethanesulfonate (triflate), nonafluorobutanesulfonate (—OSO$_2$CF$_2$CF$_2$CF$_2$CF$_3$, nonflate), p-nitrobenzoate, phosphonate, halide and the like.

"Hydroxy protecting group" refers to a labile chemical moiety which is known in the art to protect a hydroxy group against undesired reactions during synthetic processes. The hydroxy protecting group may be selectively removed when there is no need for its protection. Some suitable hydroxy protecting groups are described in P. G. M. Wuts and T. H. Greene, "*Greene's Protective Groups in Organic Synthesis*," 4th edition, Wiley-Interscience, New York (2006), which is incorporated herein by reference. Some non-limited examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. In some embodiments, the hydroxy protecting group is acetyl, benzoyl, or trimethylsilyl.

"Reacting", "contacting" or the like refers to contacting one reactant, reagent, solvent, catalyst, reactive group or the like with another reactant, reagent, solvent, catalyst, reactive group or the like. Reactants, reagents, solvents, catalysts, reactive group or the like can be added individually, simultaneously or separately and can be added in any order. They can be added in the presence or absence of heat and can optionally be added under an inert atmosphere. In some embodiments, "reacting" refers to in situ formation or intra-molecular reaction where the reactive groups are in the same molecule.

"Substantially react" refers to that at least a reactant of a reaction is consumed by an amount of more than about 75% by mole, by more than about 80% by mole, by more than about 85% by mole, or by more than about 90% by mole. In some embodiments, "substantially react" refers to that the reactant is consumed by more than about 95% by mole. In other embodiments, "substantially react" refers to that the reactant is consumed by more than about 97% by mole. In further embodiments, "substantially react" refers to that the reactant is consumed by more than about 99% by mole.

"Cancer" refers to a group of diseases in which cells are aggressive (grow and divide without respect to normal limits), invasive (invade and destroy adjacent tissues), and sometimes metastatic (spread to other locations in the body).

Tumor refers to an abnormal proliferation of genetically altered cells. Tumor can be malignant tumor or benign tumor. A benign tumor is a solid neoplasm that stops growing by itself, does not invade other tissues and does not form metastases.

"Diabetic retinopathy" refers to a diabetic eye disease caused by changes in the blood vessels of the retina. In some people with diabetic retinopathy, blood vessels may swell and leak fluid. In other people, abnormal new blood vessels grow on the surface of the retina.

"Rheumatoid arthritis" refers to a chronic, inflammatory autoimmune disorder that causes the immune system to attack the joints. It is a systemic disease, often affecting extra-articular tissues throughout the body including the skin, blood vessels, heart, lungs, and muscles.

"Psoriasis" refers to a chronic (long-lasting) skin disease characterized by scaling and inflammation. Scaling occurs when cells in the outer layer of skin reproduce faster than normal and pile up on the skin's surface. Psoriasis may be related to an abnormal immune system that produces too many of the immune cells, i.e., T cells, in the skin. These T cells may trigger the inflammation and excessive skin cell reproduction seen in people with psoriasis. This leads to inflammation and flaking of skin.

"Obesity" refers to a condition in which the natural energy reserve, stored in the fatty tissue of humans and other mammals, is increased to a point where it is associated with certain health conditions or increased mortality.

"Chronic kidney disease" or "chronic renal disease" refers to a progressive loss of renal function over a period of months or years through five stages. Each stage is a progression through an abnormally low and deteriorating glomerular filtration rate, which is usually determined indirectly by the creatinine level in blood serum.

"Intestinal microsporidiosis" refers to an intestinal infection with microsporidia. "Microsporidiosis" refers to an infection with microsporidia. It is a symptomatic disease develops predominantly in patients with AIDS and includes chronic diarrhea, disseminated infection, and corneal disease.

"Amebiasis" refers to an intestinal infection with a microscopic parasite called *Entamoeba histolytica* (*E. histolytic*). The parasite is an amoeba, a single-celled organism. It is generally asymptomatic, but mild diarrhea to severe dysentery may occur.

"Taeniasis solium" refers to an infection with adult worms that follows ingestion of contaminated pork.

"Cysticercosis" refers to an infection with larvae of Taenia solium from ova in human feces.

"Cryptosporidiosis" refers to an infection with Cryptosporidium. The primary symptom is watery diarrhea.

"Giardiasis" refers to an infection with the flagellated protozoan *Giardia lamblia*. Infection can be asymptomatic or cause symptoms ranging from intermittent flatulence to chronic malabsorption.

"Anisakiasis" refers to an infection with larvae of worms of the genus *Anisakis* and related genera such as Pseudoterranova. Infection is generally acquired by eating raw or poorly cooked saltwater fish.

"Pharmaceutically acceptable salt" refers to a salt of acidic or basic group that may be present in the compounds disclosed herein. Compounds that are basic in nature are capable of forming a wide variety of salts with various inorganic and organic acids. The acids that may be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide, and pamoate. Compounds disclosed herein that include an amino group also can form pharmaceutically acceptable salts with various amino acids, in addition to the acids mentioned above. Compounds disclosed herein that are acidic in nature are capable of forming base salts with various pharmacologically acceptable cations. Non-limiting examples of such salts include alkali metal or alkaline earth metal salts and, particularly, calcium, magnesium, sodium, lithium, zinc, potassium, and iron salts.

"Stereoisomer" refers to all enantiomerically/stereomerically pure and enantiomerically/stereomerically enriched compound disclosed herein.

"Stereomerically pure" or "enantiomerically pure" refers to a compound comprises one stereoisomer and is substantially free of its counter stereoisomer or enantiomer. For example, a compound is stereomerically or enantiomerically pure when the compound contains 80%, 90% or 95% or more of one stereoisomer and 20%, 10% or 5% or less of the counter stereoisomer. In some cases, a compound disclosed herein is considered optically active or stereomerically/enantiomerically pure (i.e., substantially the R-form or substantially the S-form) with respect to a chiral center when the compound is about 80% ee (enantiomeric excess) or greater, preferably, equal to or greater than 90% ee with respect to a particular chiral center and more preferably 95% ee with respect to a particular chiral center.

"Stereomerically enriched" or "enantiomerically enriched" refers to racemic mixtures as well as other mixtures of stereoisomers of compounds disclosed herein (e.g., R/S=30/70, 35/65, 40/60, 45/55, 55/45, 60/40, 65/35 and 70/30).

"Hydrate" refers to a compound of the present invention or a salt thereof, that further includes a stoichiometric or non-stoichiometeric amount of water bound by non-covalent intermolecular forces.

"Solvate" refers to a solvate formed from the association of one or more solvent molecules to a compound of the present invention. The term "solvate" includes hydrates (e.g., monohydrate, dihydrate, trihydrate, tetrahydrate, and the like).

"Polymorph" refers to solid crystalline forms of a compound of the present invention or complex thereof. Different polymorphs of the same compound can exhibit different physical, chemical and/or spectroscopic properties.

"Periodinane compound" refers to a chemical compound containing hypervalent iodine.

"Peroxide" refers to a compound containing an oxygen-oxygen single bond.

DETAILED DESCRIPTION

Provided herein are unsaturated α-keto esters comprising Formula (I):

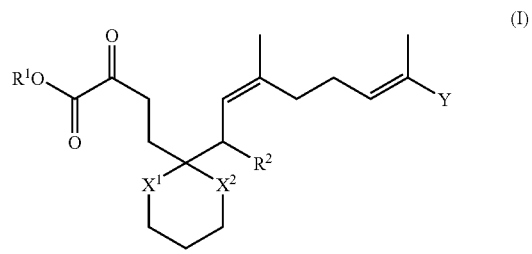

or a stereoisomer thereof, wherein $R^1$ is tosyl, mesyl, triflyl or nonflyl, or unsubstituted or substituted aryl, alkyl, alkenyl or alkynyl; $R^2$ is hydrogen or $OR^3$ where $R^3$ is alkyl, acyl (e.g., acetyl and benzoyl), aryl, arylalkyl (e.g., benzyl), alkylaryl (e.g., methylphenyl); each of $X^1$ and $X^2$ is independently O or S; and Y is —$CH_2$—$R^4$, —$CH_2$—$OR^5$, —$C(=O)$—$R^6$ or —$C(=O)$—$OR^7$ where each of $R^4$, $R^5$, $R^6$ and $R^7$ is independently H, alkyl, acyl, aryl, arylalkyl, alkylaryl, trialkylsilyl, methoxymethyl, dialkylamino, diarylamino or alkylarylamino.

In some embodiments, the stereoisomer is an enantiomer of Formula (I). In certain embodiments, the stereoisomer is a diastereomer of Formula (I). In other embodiments, each of $X^1$ and $X^2$ is S. In certain embodiments, $R^1$ is alkyl such as methyl and t-butyl. In further embodiments, $R^2$ is H. In still further embodiments, Y is alkyl such as methyl. In still further embodiments, each of $X^1$ and $X^2$ is S; $R^1$ is alkyl; $R^2$ is H; and Y is alkyl.

Also provided herein are processes of making an unsaturated α-keto ester of Formula (I):

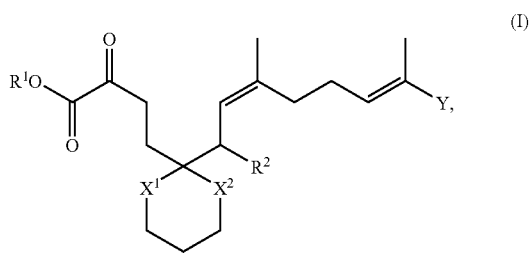

wherein the process comprises oxidizing the unsaturated α-hydroxyl ester of Formula (III):

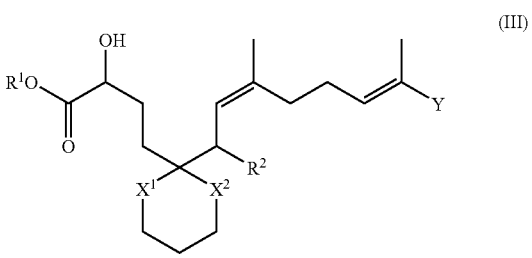

or a stereoisomer thereof,
with an oxidant to form the unsaturated α-keto ester of Formula (I), wherein $R^1$, $R^2$, $X^1$, $X^2$ and Y are as defined herein.

Any oxidant that can oxidize an alcohol to an aldehyde can be used herein. In some embodiments, the oxidant is a periodinane compound. In other embodiments, the oxidant is Dess-Martin periodinane, i. e., 1,1,1-triacetoxy-1,1-dihydro-1,2- benziodoxol-3(1H)-one (CAS 87413-09-0). In further embodiments, the oxidant is pyridinium dichromate (PDC), pyridinium chlorochromate (PCC), tetrapropylammonium perruthenate/N-methylmorpholine N-oxide (TPAP/NMO) or a combination thereof.

The unsaturated α-hydroxyl ester of Formula (III) can be prepared by the methods disclosed herein or by other methods known to skilled artisans. In some embodiments, the unsaturated α-hydroxyl ester of Formula (III) is prepared by contacting an ester of Formula (II):

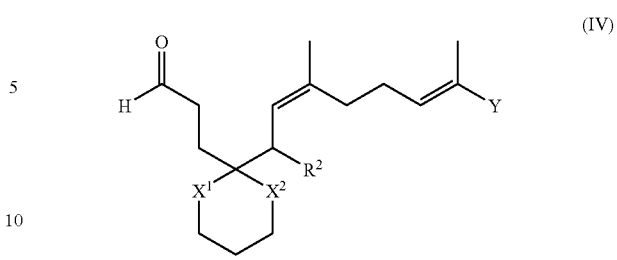

or a stereoisomer thereof with a base and a peroxide.

Any peroxide that contains an oxygen-oxygen single bond can be used herein. Some non-limiting examples of peroxide include compounds having R'—O—O—R" where each of R' and R" is independently H, alkyl or aryl. Other non-limiting examples of peroxide include hydrogen peroxide, superoxides, dioxygenyls, ozones and ozonides compound. In certain embodiments, the peroxide is t-BuOOH.

Any base known to a person skilled in the art can be used herein. In some embodiments, the base is an organolithium reagent such as lithium diisopropylamide (LDA), lithium bis(trimethylsilyl)amide (LiHMDS), lithium hexamethyldisilazide (LiHMDS), methyllithium, butyllithium, hexyllithium, sec-butyllithium, and phenyllithium; an organopotassium reagent such as potassium bis(trimethylsilyl)amide (KHMDS); or an organosodium reagent such as sodium bis(trimethylsilyl)amide (NaHMDS).

In other embodiments, the unsaturated α-hydroxyl ester of Formula (III) is prepared by the steps of:

(a) contacting an aldehyde of Formula (IV):

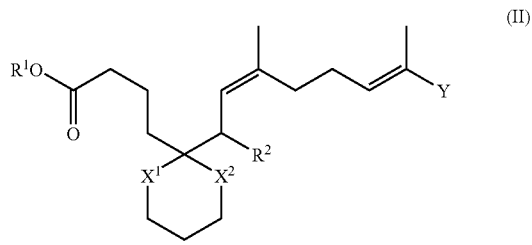

or a stereoisomer thereof with a mixture of isocyanate and $SiCl_4$ in the presence of a catalytic amount of pyridine N-oxide or hexamethylphosphoramide (HMPA); and (b) quenching the reaction mixture with an alcohol having a formula represented by $R^1OH$ and sodium bicarbonate, wherein $R^1$, $R^2$, $X^1$, $X^2$ and Y are as defined herein.

Scheme 1 below depicts embodiments of the preparation of the unsaturated α-keto ester of Formula (I), where each of $X^1$ and $X^2$ is S; $R^1$ is methyl or t-butyl; $R^2$ is H; and Y is methyl, i.e., Compound 7a and 7b, from 1,3-dithiane 1. Each of the acetal 4 and tert-butyl ester 8 contains a 2,2-disubstituted dithiane group and they can be prepared independently through an one-pot reaction with two deprotonation-alkylation sequence as described in Seebach, D.; Corey, E. J., *J. Org. Chem.*, 1975, 40, 231, which is incorporated herein by reference. The acetal 4 can be deprotected to aldehyde 5, which can be then treated with $SiCl_4$ and t-BuNC in the presence of pyridine N-oxide or HMPA, and quenched with MeOH and saturated $NaHCO_3$ solution, to give compound 6a. The tert-butyl ester 8 was converted to 6b through α-hydroxylation with t-BuOOLi (Julia, M.; Jalmes, V. P.-S.; Plé, K.; Verpeaux, J.-N.; Hollingworth, G., *Bull. Soc. Chim. Fr.*, 1996, 133, 15, which is incorporated herein by reference. Compound 6a or 6b can be converted to the cyclization precursors 7a or 7b by Dess-Martin oxidation as described in Dess, D. B.; Martin, J. C., *J. Org. Chem.*, 1983, 48, 4155; and Dess, D. B.; Martin, J. C., *J. Am. Chem. Soc.*, 1991, 113, 7277, both of which are incorporated herein by reference.

Scheme 1

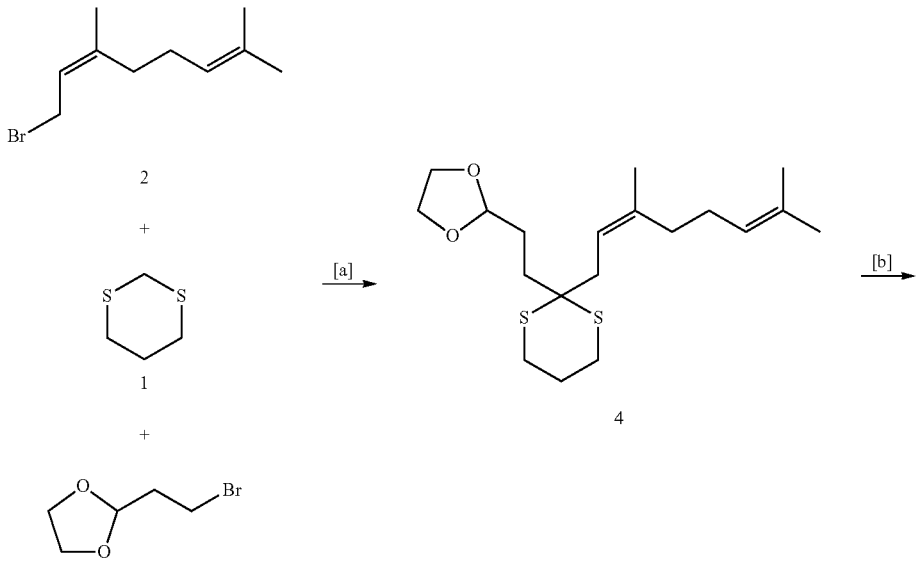

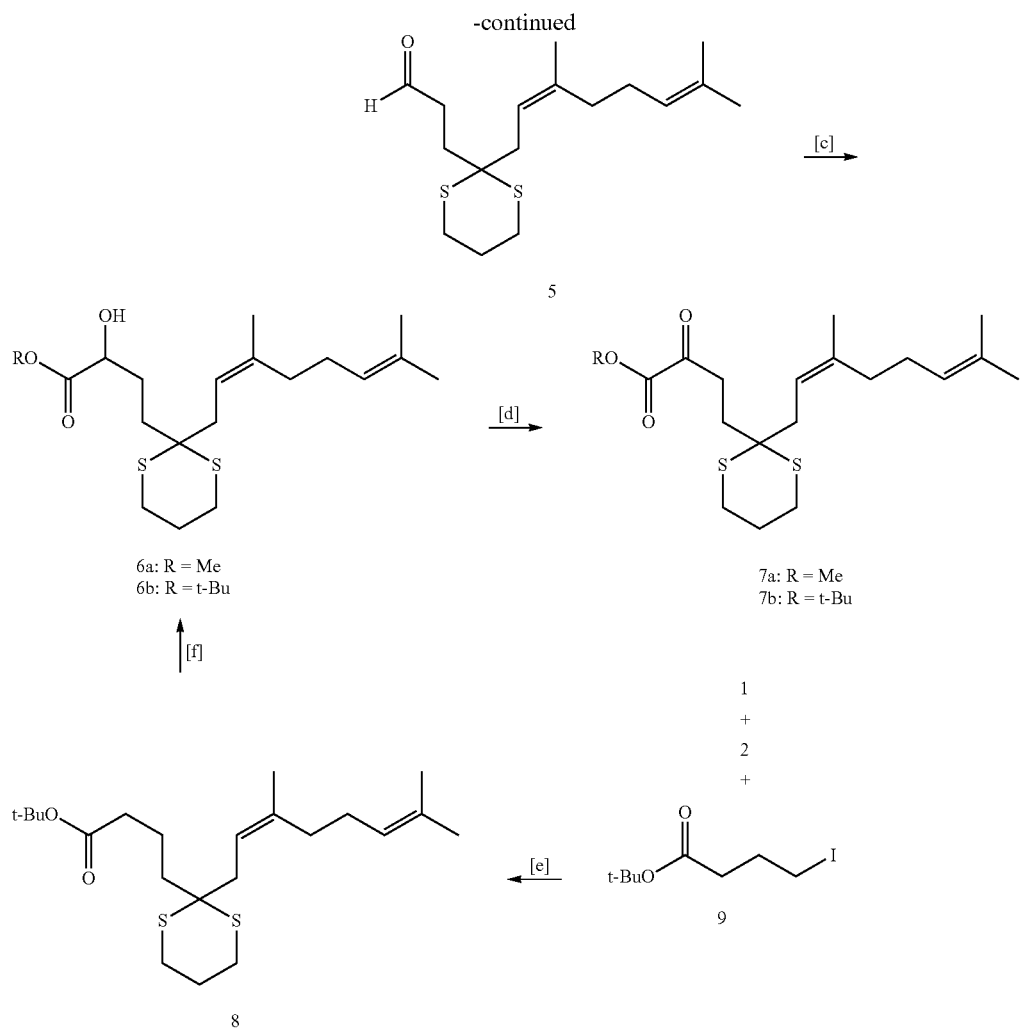

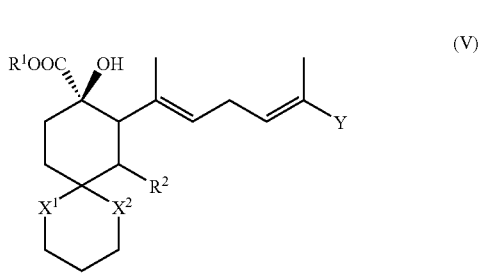

8

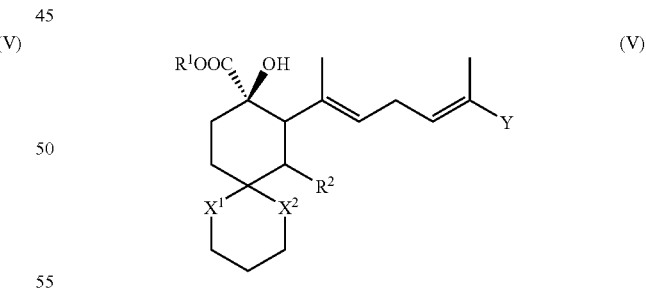

9

Also provided herein is a 5-demethoxyfumagillol intermediate comprising Formula (V):

(V)

or a stereoisomer thereof, wherein $R^1$, $R^2$, $X^1$, $X^2$ and Y are as defined herein.

In some embodiments, the stereoisomer is an enantiomer of Formula (V). In certain embodiments, the stereoisomer is a diastereomer of Formula (V). In other embodiments, each of $X^1$ and $X^2$ is S. In certain embodiments, $R^1$ is alkyl such as methyl and t-butyl. In further embodiments, $R^2$ is H. In still further embodiments, Y is alkyl such as methyl. In still further embodiments, each of $X^1$ and $X^2$ is S; $R^1$ is alkyl; $R^2$ is H; and Y is alkyl.

Also provided herein are processes of making a 5-demethoxyfumagillol intermediate having formula (V):

(V)

or a stereoisomer thereof, wherein the process comprises the step of contacting the unsaturated α-keto ester of Formula (I) with a Lewis acid, and wherein $R^1$, $R^2$, $X^1$, $X^2$ and Y are as defined herein.

In some embodiments, the Lewis acid is copper triflate (Cu(OTf)$_2$), copper hexafluoroantimonate (Cu(SbF$_6$)$_2$), scandium(III) trifluoromethanesulfonate (Sc(OTf)$_3$), ytterbium trifluoromethanesulfonate (Yb(OTf)$_3$), magnesium perchlorate (Mg(ClO$_4$)$_2$) or a combination thereof.

In certain embodiments, the bisoxazoline ligand is (S,S)-2,2-bis(4-phenyl-2-oxazolin-2-yl)propane ((S,S)-Ph-BOX;

CAS 131457-46-0), (R,R)-2,2-bis(4-phenyl-2-oxazolin-2-yl)propane ((R,R)-Ph-BOX; CAS 150529-93-4), (S,S)-2,2'-bis(4-tert-butyl-2-oxazoline)propane ((S,S)-tBu-BOX; CAS 132098-54-5), (R,R)-2,2'-bis(4-tert-butyl-2-oxazoline)propane ((R,R)-tBu-BOX; CAS 150529-93-4), 2,6-bis[(4S)-4-isopropyl-2-oxazolinyl]pyridine ((4S)-iPr-PyBOX; CAS 118949-61-4), 2,6-bis[(4R)-4-isopropyl-2-oxazolinyl]pyridine ((4R)-iPr-PyBOX; CAS 131864-67-0), 2,6-bis[(4S)-4-phenyl-2-oxazolinyl]pyridine ((4S)-Ph-PyBOX; CAS 174500-20-0), 2,6-bis[(4R)-4-phenyl-2-oxazolinyl]pyridine ((4R)-Ph-PyBOX; CAS 128249-70-7) or a combination thereof.

Scheme 2 below depicts embodiments for the preparation of the 5-demethoxyfumagillol intermediate having formula (V) where each of $X^1$ and $X^2$ is S; $R^1$ is methyl or t-butyl; $R^2$ is H; and Y is methyl, i.e., Compound 10a or 10b. The reaction can be promoted by the use of a copper(II) salt with the chiral ligand of Ph-box to provide a combination of good yield, diastereoselectivity, regioselectivity and enatioselectivity.

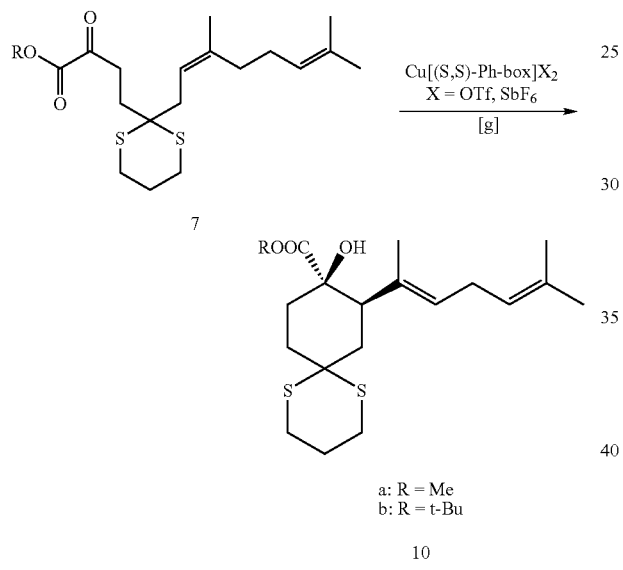

Also provided herein is an unsaturated alcohol comprising Formula (VI):

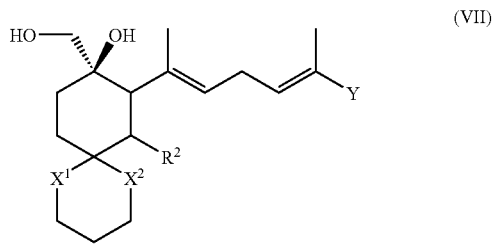

or a stereoisomer thereof,
wherein $R^1$ is tosyl, mesyl, triflyl or nonflyl, or unsubstituted or substituted aryl, alkyl, alkenyl or alkynyl; $R^2$ is hydrogen or $OR^3$ where $R^3$ is H, alkyl, acyl, aryl, arylalkyl or alkylaryl; each of $X^1$ and $X^2$ is independently O or S; and Y is —$CH_2$—$R^4$, —$CH_2OR^5$, —$C(=O)$—$R^6$ or —$C(=O)$—$OR^7$ where each of $R^4$, $R^5$, $R^6$ and $R^7$ is independently H, alkyl, acyl, aryl, arylalkyl, alkylaryl, trialkylsilyl, methoxymethyl, dialkylamino, diarylamino or alkylarylamino.

Also provided herein are processes of making an unsaturated alcohol, i.e. a 5-demethoxyfumagillol intermediate, having formula (VI):

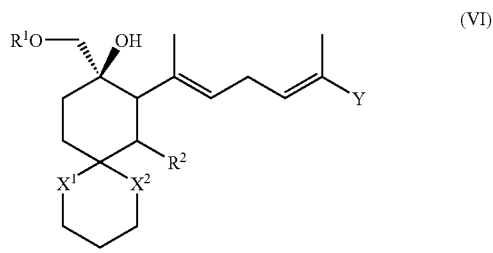

or a stereoisomer thereof,
wherein the processes comprise the steps of:
(a) contacting an unsaturated ester of Formula (V) with LiAlH$_4$ or DIBAL-H to form an unsaturated diol of Formula (VII),

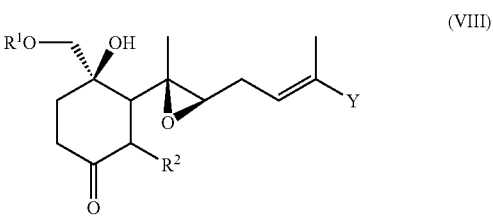

or a stereoisomer thereof, and
(b) selectively protecting the unsaturated diol of Formula (VII) or a stereoisomer thereof with a tosylate, halide, mesylate or triflate to form the unsaturated ester of Formula (VI), wherein $R^1$ is tosyl, mesyl, triflyl or nonflyl, or unsubstituted or substituted aryl, alkyl, alkenyl or alkynyl; $R^2$ is hydrogen or $OR^3$ where $R^3$ is H, alkyl, acyl, aryl, arylalkyl, alkylaryl; each of $X^1$ and $X^2$ is independently O or S; and Y is —$CH_2$—$R^4$, —$CH_2OR^5$, —$C(=O)$—$R^6$ or —$C(=O)$—$OR^7$ where each of $R^4$, $R^5$, $R^6$ and $R^7$ is independently H, alkyl, acyl, aryl, arylalkyl, alkylaryl, trialkylsilyl, methoxymethyl, dialkylamino, diarylamino or alkylarylamino.

In some embodiments, the halide is chloride, bromide or iodide.

Also provided herein are keto epoxides comprising Formula (VIII):

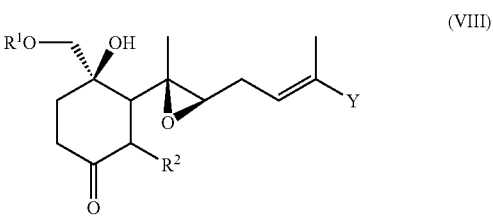

or a stereoisomer thereof,
wherein $R^1$, $R^2$, and Y are as defined herein.

In some embodiments, the stereoisomer is an enantiomer of Formula (VIII). In other embodiments, the stereoisomer is a diastereomer of Formula (VIII). In other embodiments, $R^1$ is tosyl, mesyl, triflyl or nonflyl. In further embodiments, $R^2$ is H. In still further embodiments, Y is alkyl such as methyl. In still further embodiments, $R^1$ is tosylate; $R^2$ is H; and Y is alkyl.

In certain embodiments, Y is —$CH_2$—$R^4$, —$CH_2$—$OR^5$, —C(=O)—$R^6$ or —C(=O)—$OR^7$ where each of $R^5$, $R^6$ and $R^7$ is independently H, alkyl, acyl, aryl, arylalkyl, alkylaryl, trialkylsilyl, methoxymethyl, dialkylamino, diarylamino or alkylarylamino; and $R^4$ is alkyl, acyl, aryl, arylalkyl, alkylaryl, trialkylsilyl, or methoxymethyl.

Also provided herein are processes of making a keto epoxide, i.e. a 5-demethoxyfumagillol intermediate, having formula (VIII):

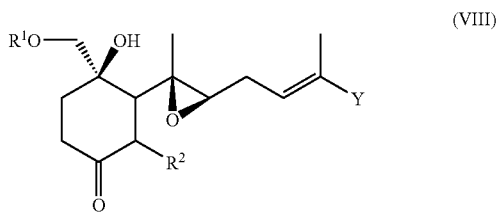

(VIII)

or a stereoisomer thereof,
wherein the processes comprise the step of contacting an unsaturated ketone of Formula (IX):

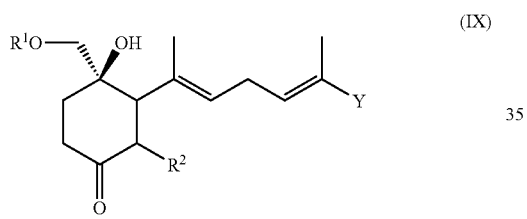

(IX)

or a stereoisomer thereof,
with Ti(iOPr)$_4$ or VO(acac)$_2$ and t-BuOOH in the presence or absence of 4 Å molecular sieves, wherein $R^1$ is tosyl, mesyl, triflyl or nonflyl, or unsubstituted or substituted aryl, alkyl, alkenyl or alkynyl; $R^2$ is hydrogen or $OR^3$ where $R^3$ is H, alkyl, acyl, aryl, arylalkyl or alkylaryl; and Y is —$CH_2$—$R^4$, —$CH_2$—$OR^5$, —C(=O)—$R^6$ or —C(=O)—$OR^7$ where each of $R^4$, $R^5$, $R^6$ and $R^7$ is independently H, alkyl, acyl, aryl, arylalkyl, alkylaryl, trialkylsilyl, methoxymethyl, dialkylamino, diarylamino or alkylarylamino. In some embodiments, the 4 Å molecular sieves are present. In other embodiments, the 4 Å molecular sieves are absent.

Scheme 3 below depicts embodiments for the preparation of the keto epoxide having Formula (VIII) where $R^1$ is tosyl, mesyl, triflyl or nonflyl; $R^2$ is H; and Y is methyl, i.e., Compound 14, as well as Compound 15, i.e., 5-demethoxyfumagillol. Compound 10a or 10b can be converted to 5-demethxoyfumagillol by the multi-step synthesis depicted in Scheme 3. A reduction of Compound 10a or 10b with LiAlH$_4$ smoothly can give diol 11. After selective protection of the primary hydroxyl of diol 11 with p-tosyl group (as described in Hartung et al., *Synthesis,* 1997, 1433, which is incorporated herein by reference), thioacetal cleavage of Compound 12 under the standard Corey condition (as described in Corey et al., *J. Org. Chem.,* 1971, 36, 3553, which is incorporated herein by reference) can lead to Compound 13. Following the literature precedent with slightly modification, hydroxyl directed epoxidation of Compound 13 with Ti(OiPr)$_4$ may lead to Compound 14 (>99% ee). Finally, the epoxide formation can be achieved together with the highly stereo-selective ketone reduction with 2.2 equivalents of K-selectride®, which may lead to Compound 15.

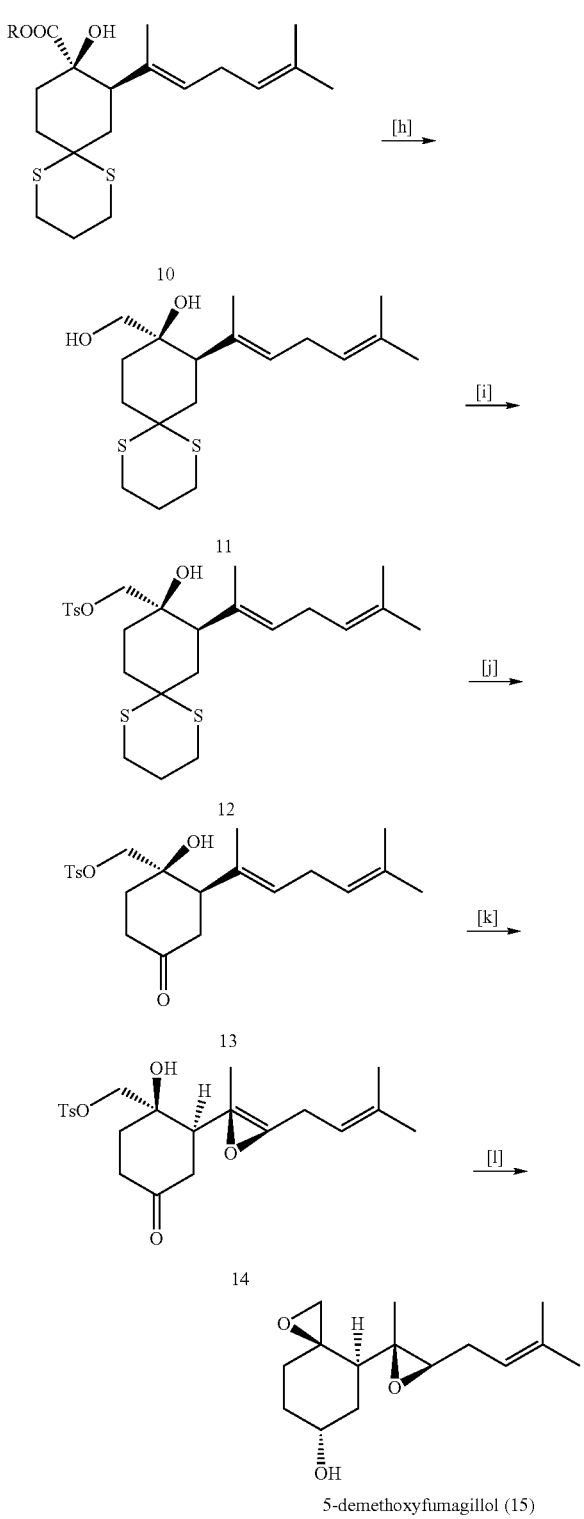

In further embodiments, the 5-demethoxyfumagillol derivative comprises Formula (X), (X'), (X"), (XI) or (XI'):

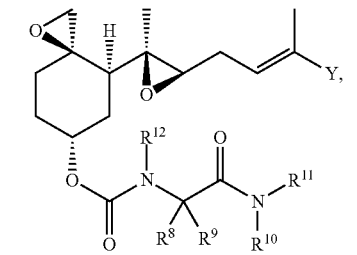
(X)

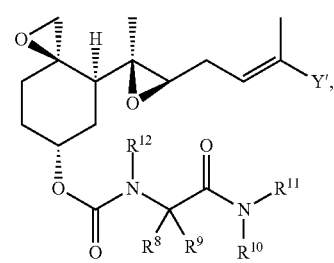
(X')

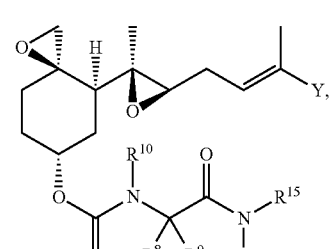
(X")

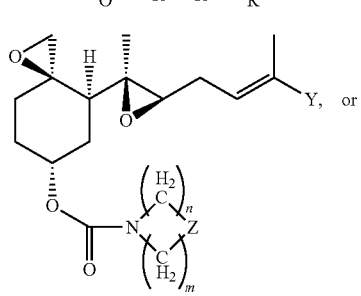
(XI)

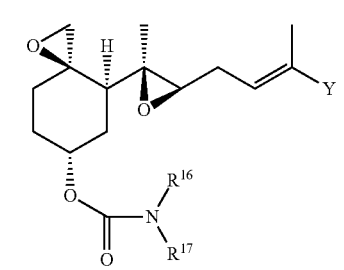
(XI')

or a pharmaceutically acceptable salt, solvate, polymorph or stereoisomer thereof, wherein each of $R^8$, $R^9$, $R^{10}$, $R^{11}$, $R^{12}$, $R^{13}$, $R^{16}$ and $R^{17}$ is independently hydrogen, or unsubstituted or substituted aryl, alkyl, cycloalkyl, alkenyl, alkynyl, arylalkyl, alkylaryl, heterocycloalkyl, heteroaryl, or —$(CH_2)_k$—$N_3$; Z is a bond, methylene, O, S or $NR^{13}$; Y is —$CH_2$—$R^4$, —$CH_2$—$OR^5$, —C(=O)—$R^6$ or —C(=O)—$OR^7$; Y' is —$CH_2$—$R^{4'}$, —$CH_2$—$OR^5$, —C(=O)—$R^6$ or —C(=O)—$OR^7$ where each of $R^4$, $R^5$, $R^6$ and $R^7$ is independently H, alkyl, aryl, arylalkyl, alkylaryl, trialkylsilyl, methoxymethyl, dialkylamino, diarylamino or alkylarylamino; $R^{4'}$ is alkyl, acyl, aryl, arylalkyl, alkylaryl, trialkylsilyl, methoxymethyl, dialkylamino, diarylamino or alkylarylamino; each of $R^{14}$ and $R^{15}$ is independently H, unsubstituted or substituted aryl, heteroaryl, cycloalkyl such as cyclopropyl and cyclopentyl, alkenyl such as vinyl and allyl, alkynyl such as prop-2-ynyl, arylalkyl, alkylaryl, or —$(CH_2)_k$—$N_3$; each of n and m is independently an integer from 0 to 9 where the sum of n and m is at least one; and k is an integer from 1 to 10, with the proviso that $R^{14}$ and $R^{15}$ are not both H.

Also provided herein are processes of making a 5-demethoxyfumagillol derivative having formula (X) or (XI):

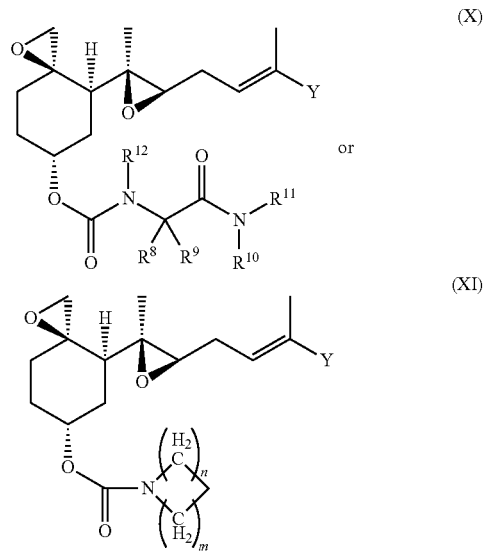

or a stereoisomer thereof, wherein the processes comprise the steps of:

(a) reacting a keto epoxide comprising Formula (VIII):

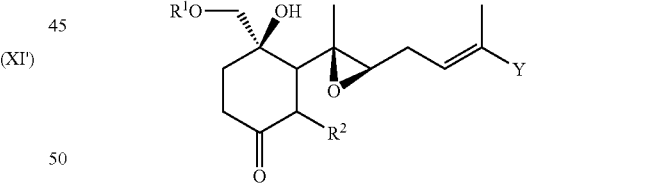

or a stereoisomer thereof,
with a base to form 5-demethoxyfumagillol of Formula (XII):

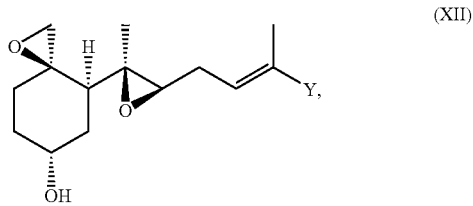

or a stereoisomer thereof, (b) contacting the 5-demethoxyfumagillol of Formula (XII) or a stereoisomer thereof with a phenylchloroformate in the presence of a first base to form an active intermediate of Formula (XIII),

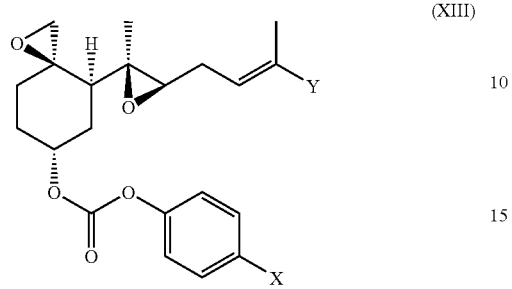

(XIII)

or a stereoisomer thereof, and (c) reacting the active intermediate of Formula (XIII) with an amine of Formula (XIV), (XV) or (XVI):

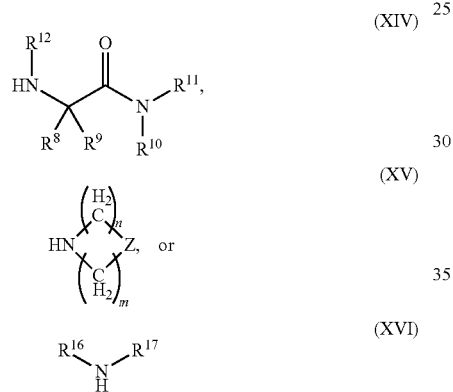

(XIV)

(XV)

(XVI)

or stereoisomer thereof in the presence of a second base, wherein $R^1$ is tosyl, mesyl, triflyl or nonflyl; X is $NO_2$ or hydrogen; each of $R^8$, $R^9$, $R^{10}$, $R^{11}$, $R^{12}$, $R^{13}$, $R^{16}$ and $R^{17}$ is independently hydrogen, or unsubstituted or substituted aryl, alkyl, cycloalkyl, alkenyl, alkynyl, arylalkyl, alkylaryl, heterocycloalkyl, heteroaryl, or —$(CH_2)_k$—$N_3$; Z is a bond, methylene, O, S or $NR^{13}$; Y is —$CH_2$—$R^4$, —$CH_2$—$OR^5$, —C(=O)—$R^6$ or —C(=O)—$OR^7$ where each of $R^4$, $R^5$, $R^6$ and $R^7$ independently H, alkyl, aryl, arylalkyl, alkylaryl, trialkylsilyl, methoxymethyl, dialkylamino, diarylamino or alkylarylamino; and each of n and m is independently an integer from 0 to 9 and the sum of n and m is at least one.

In some embodiments, the each of the first base and the second base is independently an organic base such as pyridine or triethylamine. In certain embodiments, the phenylchloroformate is unsubstituted phenylchloroformate or p-nitrophenylchloroformate.

In some embodiments, the stereoisomer is an enantiomer of Formula (X) or (XI). In other embodiments, the stereoisomer is a diastereomer of Formula (X) or (XI). In further embodiments, the 5-demethoxyfumagillol derivative of Formula (X) or (XI) has one of structures 17a-ac as shown herein:

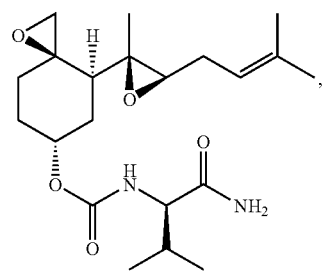

(17a)

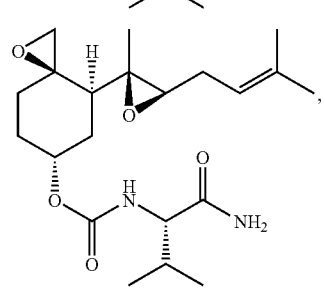

(17b)

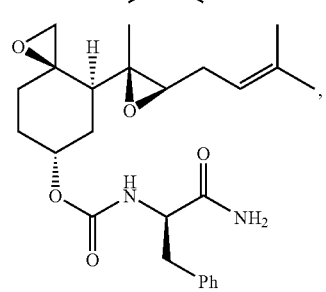

(17c)

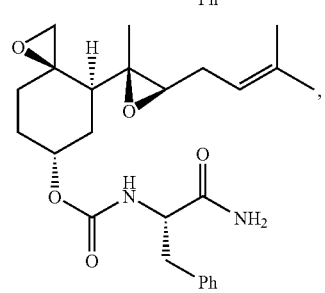

(17d)

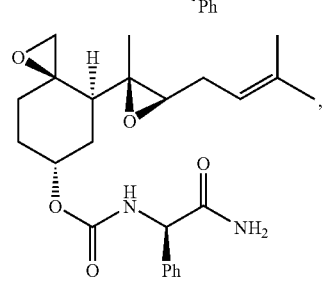

(17e)

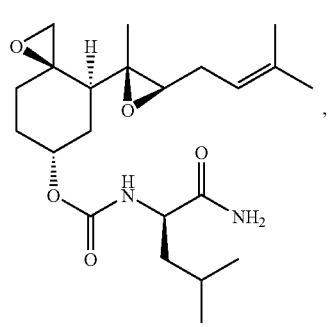

(17f)

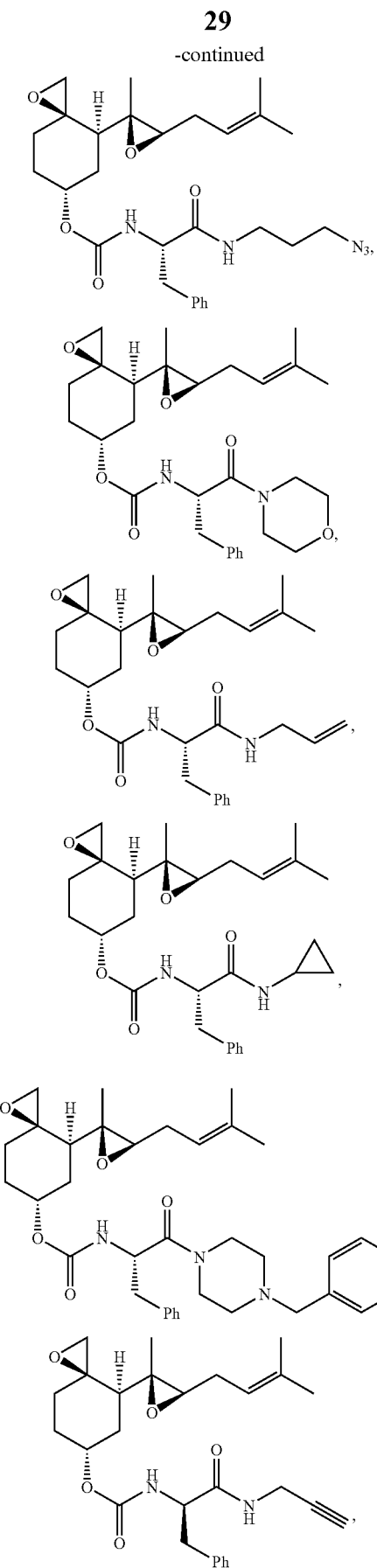
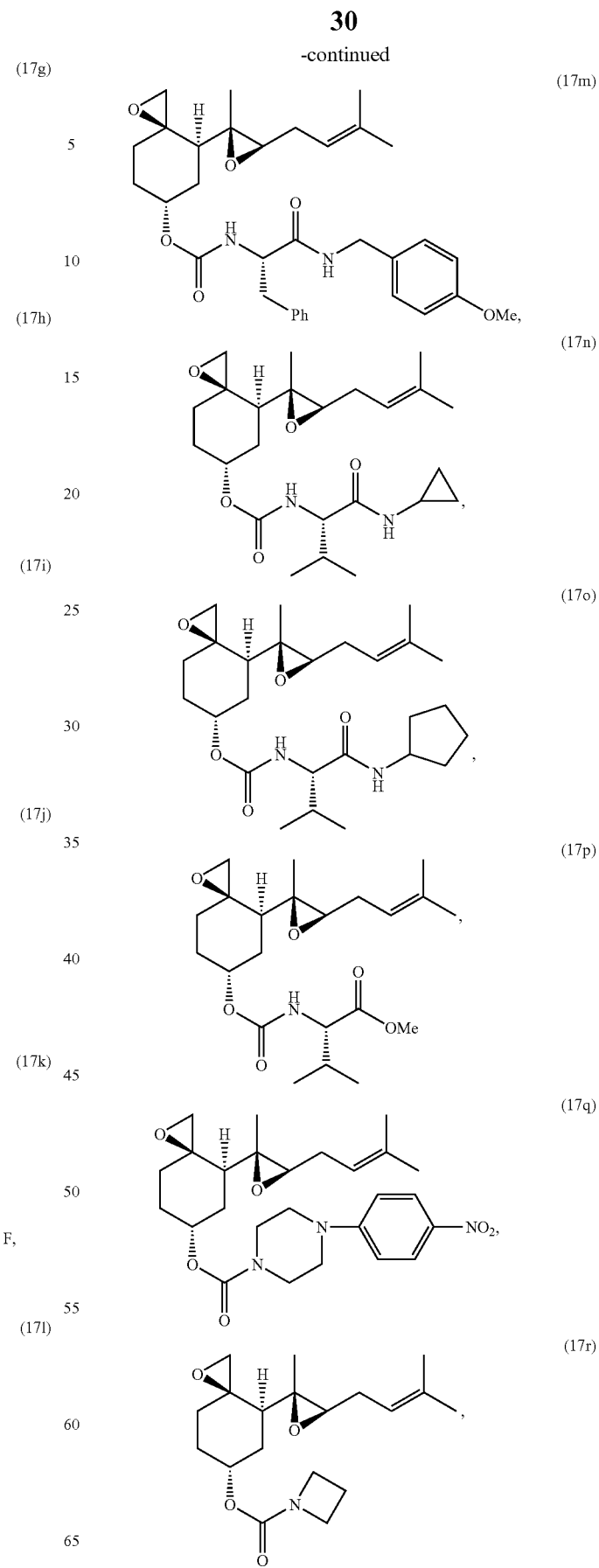

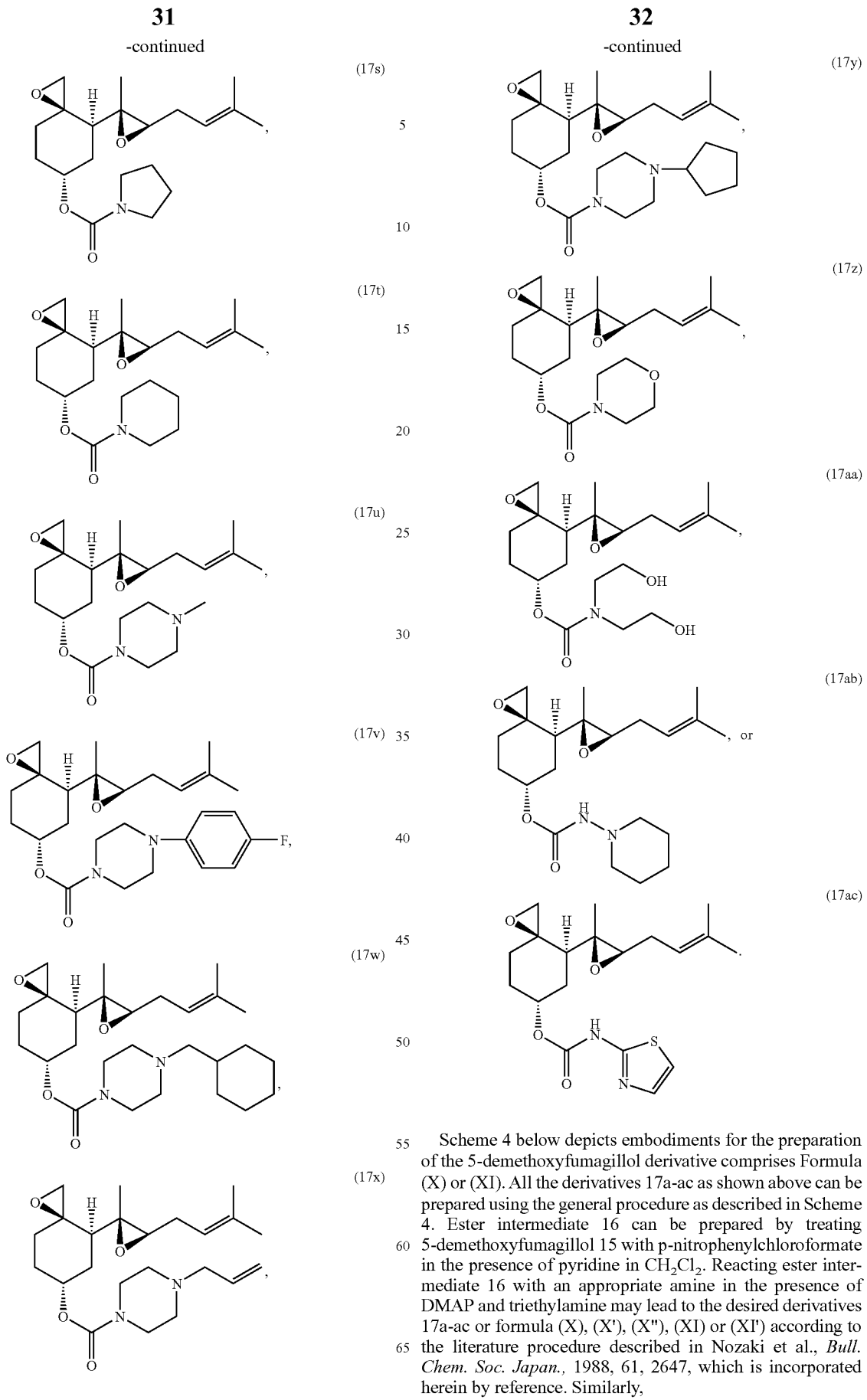

Scheme 4 below depicts embodiments for the preparation of the 5-demethoxyfumagillol derivative comprises Formula (X) or (XI). All the derivatives 17a-ac as shown above can be prepared using the general procedure as described in Scheme 4. Ester intermediate 16 can be prepared by treating 5-demethoxyfumagillol 15 with p-nitrophenylchloroformate in the presence of pyridine in $CH_2Cl_2$. Reacting ester intermediate 16 with an appropriate amine in the presence of DMAP and triethylamine may lead to the desired derivatives 17a-ac or formula (X), (X'), (X"), (XI) or (XI') according to the literature procedure described in Nozaki et al., *Bull. Chem. Soc. Japan.*, 1988, 61, 2647, which is incorporated herein by reference. Similarly,

Scheme 4

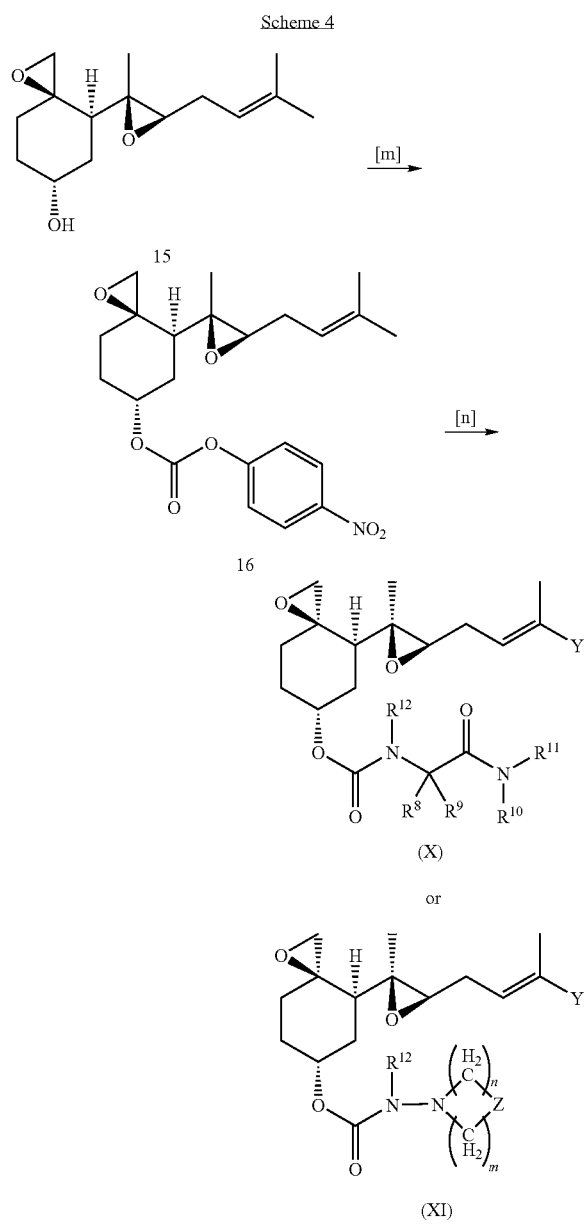

The 5-demethoxyfumagillol derivatives disclosed herein can be used as angiogenesis inhibitors or antiangiogenic agents for treating, managing or preventing a disease that is related to angiogenesis. In some embodiments, the disease related to angiogenesis is a cancer or tumor. In further embodiments, the disease related to angiogenesis is prostate cancer, lung cancer, colorectal cancer, bladder cancer, pancreatic cancer, endometrial cancer, ovarian cancer, cutaneous melanoma, leukemia, non-Hodgkin lymphoma or pancreatic cancer.

In addition to cancer or tumor, the 5-demethoxyfumagillol derivatives disclosed herein can be used for treating, managing or preventing diabetic retinopathy, rheumatoid arthritis, psoriasis, obesity, chronic kidney disease or intestinal infection. In some embodiments, the disease is an intestinal infection selected from intestinal microsporidiosis, taeniasis solium, cysticercosis, amebiasis, anisakiasis, giardiasis, or cryptosporidiosis.

In certain embodiments, the method for treating, managing or preventing a disease related to angiogenesis or other diseases disclosed herein comprises administering a 5-demethoxyfumagillol derivative of disclosed herein, or a pharmaceutically acceptable salt, solvate, polymorph or stereoisomer thereof. In other embodiments, the disease disclosed herein occurs in a mammal. In further embodiments, the mammal is a human.

In another aspect, provided herein are pharmaceutical compositions comprising a 5-demethoxyfumagillol derivative disclosed herein, or a pharmaceutically acceptable salt, solvate, polymorph or stereoisomer thereof, and a pharmaceutically acceptable carrier.

The 5-demethoxyfumagillol derivatives disclosed herein can be used as a medicament or pharmaceutical composition for curative or preventive purpose. Specifically, the 5-demethoxyfumagillol derivatives may be used in a method of therapeutic treatment that consists of administering the 5-demethoxyfumagillol derivative or a pharmaceutically acceptable salt, solvate, polymorph or stereoisomer thereof to a mammal. As such, the compounds may be used in the preparation of a medicament for curative or preventive purposes, intended for the treatment of the human or animal body.

The medicament may be administered directly in vivo, for example, into a muscle by infusion, into the lungs by aerosol and the like. It is also possible to adopt an ex vivo approach, which consists of collecting cells from the patient (bone marrow stem cells, peripheral blood lymphocytes, muscle cells, nerve cells, neuron cells, epithelial cells and the like), administering the compounds and re-administering the cells to the patient.

The 5-demethoxyfumagillol derivatives provided herein may be administered by the intramuscular, intratracheal, intranasal, intracerebral, intrapleural, intratumoral, intracardiac, intragastric, intraperitoneal, epidermal, intravenous or intraarterial route by a syringe or by any other equivalent means, systems suitable for the treatment of the airways or of the mucous membranes such as inhalation, instillation or aerosolization. Other routes of administration include application of a cream, oral administration or any other means known to the person skilled in the art and applicable to the compounds and compositions provided herein.

Administration may be achieved by a variety of different routes. One route is oral administration of a composition such as a pill, capsule or suspension. Such composition may be prepared according to any method known in the art, and may comprise any of a variety of inactive ingredients. Suitable excipients for use within such compositions include insert diluents (which may be solid materials, aqueous solutions and/or oils) such as calcium, potassium, or sodium carbonate, lactose, calcium, potassium, or sodium phosphate, water, arachis oil, peanut oil, liquid paraffin or olive oil; granulating and disintegrating agents such as maize starch, gelatin or acacia and/or lubricating agents suchas magnesium stearate, stearic acid, or talc. Other inactive ingredients that may, but need not, be present include one or more suspending agents (e.g., sodium carboxymethylcellulose, methylcellulose, hydroxypropylmethylcellulose, sodium alginate, polyvinylpyrrolidone, gum tragacanth, and gum acacia), thickeners (e.g., beeswax, paraffin or cetyl alcohol), dispersing or wetting agents, preservatives (e.g., antioxidants such as ascorbic acid), coloring agents, sweetening agents and/or flavoring agents.

A pharmaceutical composition may be prepared with carriers that protect active ingredients against rapid elimination from the body, such as time release formulations or coatings.

Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid, polyethylene glycols, polyethylene glycol ethers, and others known to those of ordinary skill in the art.

In other embodiments, provided are methods in which the compounds are directly administered as a pressurized aerosol or nebulized formulation to the patient's lungs via inhalation. Such formulations may contain any of a variety of known aerosol propellants useful for endopulmonary and/or intranasal inhalation administration. In addition, water may be present, with or without any of co-solvents, surfactants, stabilizers (e.g., antioxidants, chelating agents, insert gases and buffers). For compositions to be administered from multiple dose containers, antimicrobial agents are typically added. Such compositions may also be filtered and sterilized, and may be lyophilized to provide enhanced stability and to improve solubility.

Pharmaceutical compositions can be administered in an amount, and with a frequency, that is effective to inhibit or alleviate the symptoms of a disease or condition, such as cystic fibrosis, and/or delay the progression of the disease. The precise dosage and duration of treatment may be determined empirically using known testing protocols or by testing the composition in model systems known in the art and extrapolating therefrom. Dosages may also vary with the severity of the disease. A pharmaceutical composition may be formulated and administered to exert a therapeutically useful effect while minimizing undesirable side effects. It will be apparent that, for any particular subject, specific dosage regimens may be adjusted over time according to the individual need.

As noted above, a pharmaceutical composition may be administered to a mammal to treat, manage or prevent cancer, tumor, diabetic retinopathy, rheumatoid arthritis, psoriasis, obesity, chronic kidney disease or intestinal infection. Patients that may benefit from administration of a 5-demethoxyfumagillol derivative provided herein are those afflicted with cancer, tumor, diabetic retinopathy, rheumatoid arthritis, psoriasis, obesity, chronic kidney disease or intestinal infection. Such patients may be identified based on standard criteria that are well known in the art.

Also provided are methods of administering the pharmaceutical compositions by intravenous, oral, instillation, inhalation, topical, intraperitoneal, subcutaneous, or intramuscular routes. The pharmaceutical compositions may be administered, for example, in the form of capsules, powders, tablets, liquids, solutions, and aerosolized solutions.

Additional features and advantages of the invention will be set forth, and in part will be apparent from the description, or may be learned by practice of the invention.

Dosages of the compositions provided will vary, depending on factors such as half-life of the compound, potential adverse effects of the compound or of degradation products thereof, the route of administration, the condition of the patient, and the like. Such factors are capable of determination by those skilled in the art. The exact dose level given on a daily basis, of course, is meant to be adapted by a physician to provide the optimum therapeutic response.

EXAMPLES

The methods of making 5-demethoxyfumagillol and derivatives and precursors thereof are described in detail for compounds 4-16 and 17a-a. The detailed disclosure falls within the scope of, and serve to exemplify, the above described General Synthetic Procedures which form part of this disclosure. These examples are presented for illustrative purposes only and are not intended to limit the scope of this disclosure.

Preparation of Compound 4

Compound 4 was prepared according to Step a of Scheme 1 which is described as follows. 1,3-Dithiane was dissolved in THF, and treated dropwise with 1.1 equivalents of n-BuLi (2.5 M in hexane) while stirring at $-78°$ C. Stirring was continued at $-20°$ C. for 2 hours and the anion so obtained was cooled to $-78°$ C. HMPA was added and stirring was kept for 15 minutes. 1.1 Equivalents of neryl bromide 2 was added to the above solution. After stirring for 30 minutes at $-78°$ C., another portion of 1.1 equivalents of n-BuLi (2.5 M in hexane) was added to the solution. Stirring was continued for 2 h, and 1.1 equivalents of 3 were added dropwise at $-78°$ C. Acetal 4 was purified by flash column chromatography (90% yield).

Compound 4 was characterized by the following experimental data: $R_f$=0.48 (silica gel, hexane/EtOAc, 4:1); $^1$H NMR (300 MHz, CDCl$_3$) δ 5.26 (t, J=7.0 Hz, 1H), 5.12 (br s, 1H), 4.90 (t, J=4.5 Hz, 1H), 3.99-3.95 (m, 2H), 3.87-3.84 (m, 2H), 2.88-2.84 (m, 2H), 2.78-2.64 (m, 2H), 2.55 (d,J=7.0 Hz, 2H), 2.07-2.03 (m, 6H), 1.96-1.89 (m, 2H), 1.84-1.77 (m, 2H), 1.74 (d,J=1.2 Hz, 3H), 1.68 (s, 3H), 1.61 (s, 3H); $^{13}$C NMR (75.5 MHz, CDCl$_3$) δ 138.3, 131.5, 124.0, 118.4, 104.1, 64.8, 52.9, 36.7, 32.2, 31.6, 28.9, 26.3, 25.9, 25.6, 25.1, 23.5, 17.5; IR (CH$_2$Cl$_2$) 2933, 1734 cm$^{-1}$; LRMS (EI, 20 eV) m/z 356 (M+, 4), 219 (100) 113 (55); HRMS (EI) calcd for C$_{19}$H$_{32}$O$_2$S$_2$ [M]$^+$ 356.1844, found 356.1830.

Preparation of Compound 5

Compound 5 was prepared according to Step b of Scheme 1 which is described as follows. 3 Equivalents of 2,6-lutidine and 2 equivalents of TMSOTf were added to a solution of 4 in CH$_2$Cl$_2$ at 0° C. under Argon. The mixture was stirred at the same temperature for 1 minute, and H$_2$O was added to the resulting mixture and stirred for 30 minutes. Aldehyde 5 was purified by flash column chromatography (80% yield).

Compound 5 was characterized by the following experimental data: $R_f$=0.50 (silica gel, hexane/EtOAc, 4:1); $^1$H NMR (400 MHz, CDCl$_3$) δ 9.83 (t, J=1.1 Hz, 1H), 5.26 (dt, J=6.9, 1.1 Hz, 1H), 5.11 (br s, 1H), 2.87 (ddd, J=14.5, 9.0, 3.3 Hz, 2H), 2.75 (ddd, J=14.5, 7.0, 3.5 Hz, 2H), 2.63 (dt, J=7.5, 1.0 Hz, 2H), 2.54 (dd, J=7.0, 1.0 Hz, 2H), 2.28 (t, J=7.7 Hz, 2H), 2.08-2.07 (m, 4H), 2.00-1.90 (m, 2H), 1.74 (d, J=1.3 Hz, 3H 1.69 (s, 3H), 1.62 (s, 3H); $^{13}$C NMR (100 MHz, CDCl$_3$) δ 201.1, 139.0, 131.8, 124.0, 118.2, 52.6, 39.7, 37.3, 32.4, 30.2, 26.4, 26.1, 25.7, 25.0, 23.6, 17.7; IR (CH$_2$Cl$_2$) 2929, 2869, 1723 cm$^{-1}$; LRMS (EI, 20 eV) m/z 312 (M$^+$, 2), 175 (100), 119 (8); HRMS (EI) calcd for C$_{17}$H$_{28}$OS$_2$ [M]$^+$ 312.1582, found 312.1581.

Preparation of Compound 6a

Compound 6a was prepared according to Step c of Scheme 1 which is described as follows. t-BuNC (1.2 equivalents) was added to a solution of Compound 5, pyridine N-oxide (0.1 equivalent) and SiCl$_4$ (1.1 equivalents) in CH$_2$Cl$_2$ at $-78°$ C. After being stirred further for 1 hour at 0° C., the solution was cooled to $-78°$ C. and 50 equivalents of dry MeOH was added dropwise to the reation mixture. After stirring for 40 minutes at $-78°$ C., the mixture was transferred dropwise to a vigorously stirred, ice cold saturated aqueous solution of NaHCO$_3$ and further stirred for 2 hours at room temperature. Compound 6 was purified by flash column chromatography (80% yield).

Compound 6a was characterized by the following experimental data: $R_f$=0.12 (silica gel, hexane/EtOAc, 4:1); $^1$H NMR (300 MHz, CDCl$_3$) δ 5.25 (t, J=6.9 Hz, 1H), 5.12 (br s, 1H), 4.24-4.20 (m, 1H), 3.80 (s, 3H), 2.87-2.77 (m, 5H), 2.55 (d, J=6.9 Hz, 2H), 2.07-1.95 (m, 9H), 1.80-1.75 (m, 1H), 1.74 (d, J=1.2 Hz, 3H), 1.69 (s, 3H), 1.61 (s, 3H); $^{13}$C NMR (75.5 MHz, CDCl$_3$) δ 175.4, 138.6, 131.7, 124.1, 118.4, 70.1, 52.9, 52.5, 36.9, 32.9, 32.3, 29.5, 26.4, 26.0, 25.9, 25.6, 25.1, 23.6, 17.6; IR (CH$_2$Cl$_2$) 3548, 2969, 2936, 1736 cm$^{-1}$; LRMS (EI, 20 eV) m/z 372 (M$^+$, 3), 235 (100), 161 (31); HRMS (EI) calcd for C$_{19}$H$_{32}$O$_3$S$_2$ [M]$^+$ 372.1793, found 312.1801.

Preparation of Compound 8

Compound 8 was prepared according to Step e of Scheme 1 which is described as follows. 1,3-Dithiane was dissolved in THF, and treated dropwise with 1.1 equivalents n-BuLi (2.5 M in hexane) while stirring at −78° C. Stirring was continued at −20° C. for 2 hours and the anion so obtained was cooled to −78° C. HMPA was added and stirring was kept for 15 minutes. 1.1 Equivalents of neryl bromide 2 were added to the above solution. After stirring for 30 minutes at −78° C., another portion of 1.1 equivalents of n-BuLi (2.5 M in hexane) was added to the solution. Stirring was continued for 2 h, and the anion so obtained was cannulated into the solution of 1.1 equivalents of tert-butyl 4-iodobutyrate 9 in THF/HMPA (10:1, 25 mL) at −78° C. Unsaturated ester 8 was purified by flash column chromatography (70% yield).

Compound 8 was characterized by the following experimental data: R$_f$=0.42 (silica gel, hexanes/EtOAc, 9:1); IR (CH$_2$Cl$_2$) 2974, 2934, 1724, 1245, 1152 cm$^{-1}$; $^1$H NMR (300 MHz, CDCl$_3$) δ 5.25 (t, J=6.9 Hz, 1H), 5.12 (m, 1H), 2.85-2.80 (m, 4H), 2.58 (d, J=6.9 Hz, 2H), 2.23 (t, J=7.2 Hz, 2H), 2.08-2.07 (m, 4H), 1.94-1.88 (m, 4H) 1.76-1.74 (m, 2H), 1.74 (s, 3H), 1.69 (s, 3H), 1.61 (s, 3H), 1.45 (s, 9H); $^{13}$C NMR (100 MHz, CDCl$_3$) δ 172.4, 138.2, 131.4, 124.0, 118.6, 79.9, 53.0, 37.2, 36.6, 35.3, 32.2, 28.0, 26.3, 26.0, 25.6, 25.1, 23.5, 20.1, 17.5; LRMS (EI, 20 eV) m/z 398 (M$^+$, 2), 261 (33), 205 (100), 145 (15); HRMS (EI) calcd for C$_{22}$H$_{38}$O$_2$S$_2^+$ [M]$^+$ 398.2313, found 398.2317.

Preparation of Compound 6b

Compound 6b was prepared according to Step f of Scheme 1 which is described as follows. To cooled (−78° C.) THF under argon was added 4.0 equivalents of diisopropylamine, followed by 3.6 equivalents n-BuLi (2.5 M in hexane). The reaction was stirred for 10 minutes at 0° C., then cooled to −78° C., 8 in THF was then added dropwise. Stirring was continued at −78° C. for 1 hr, and then 2 equivalents of tert-butyl hydroperoxide (5.5 M in decane) were slowly added. α-Hydroxyl ester 6 was purified by flash column chromatography (68% yield).

Compound 6b was characterized by the following experimental data: R$_f$=0.31 (silica gel, hexanes/EtOAc, 4:1); $^1$H NMR (400 MHz, CDCl$_3$) δ 5.26 (t, J=6.9 Hz, 1H), 5.12 (m, 1H), 4.08 (m, 1H), 2.87-2.85 (m, 2H), 2.79-2.77 (m, 2H), 2.56 (d, J=6.8 Hz, 2H), 2.08-2.07 (m, 5H), 1.98-1.93 (m, 4H), 1.78 (m, 1H), 1.74 (s, 3H), 1.69 (s, 3H), 1.61 (s, 3H), 1.50 (s, 9H); $^{13}$C NMR (100 MHz, CDCl$_3$) δ 174.3, 138.5, 131.7, 124.1, 118.6, 82.5, 70.1, 52.9, 36.9, 32.6, 32.4, 29.4, 28.0, 26.4, 26.0 (2), 25.7, 25.2, 23.6, 17.6; IR (CH$_2$Cl$_2$) 3685, 3041, 1720, 1605, 1159 cm$^{-1}$; LRMS (EI, 20 eV) m/z 414 (M$^+$, 1), 221 (100), 153 (14), 145 (35); HRMS (EI) calcd for C$_{22}$H$_{38}$O$_3$S$_2^+$ [M]$^+$ 414.2262, found 414.2263.

Preparation of Compound 7a

Compounds 7a was prepared according to Step d of Scheme 1 which is described as follows. A solution of Compound 6a in anhydrous CH$_2$Cl$_2$ was treated sequentially at 0° C. with 10 equivalents of solid NaHCO$_3$ and 1.2 equivalents of Dess-Martin periodinane. Keto ester 7a was purified by flash column chromatography (73% yield).

Compound 7a was characterized by the following experimental data: R$_f$=0.31 (silica gel, hexane/EtOAc, 4:1); $^1$H NMR (300 MHz, CDCl$_3$) δ 5.25 (t, J=7.0 Hz, 1H), 5.12 (brs, 1H), 3.88 (s, 3H), 2.96 (t, J=7.1 Hz, 2H), 2.83-2.79 (m, 2H), 2.70-2.65 (m, 2H), 2.55 (dd, J=7.0, 0.9 Hz, 2H), 2.39 (t, J=7.1 Hz, 2H), 2.09-1.98 (m, 5H), 1.90-1.85 (m, 1H), 1.75 (d, J=1.2 Hz, 3H), 1.69 (s, 3H), 1.62 (s, 3H); $^{13}$C NMR (75.5 MHz, CDCl$_3$) δ 192.6, 161.3, 139.3, 131.8, 124.0, 117.8, 53.0, 52.6, 37.3, 34.7, 32.3, 26.4, 26.1, 25.7, 24.8, 23.6, 17.7; IR (CH$_2$Cl$_2$) 2929, 2856, 1731 cm$^{-1}$; LRMS (EI, 20 eV) m/z 370 (M$^+$, 2), 233 (100), 201 (7); HRMS (EI) calcd for C$_{19}$H$_{30}$O$_3$S$_2$ [M]$^+$ 370.1636, found 370.1633.

Preparation of Compound 7b

Compound 7b was prepared according to Step d of Scheme 1 which is described as follows. A solution of Compound 6b in anhydrous CH$_2$Cl$_2$ was treated sequentially at 0° C. with 10 equivalents of solid NaHCO$_3$ and 1.2 equivalents of Dess-Martin periodinane. Keto ester 7b was purified by flash column chromatography (73% yield).

Compound 7b was characterized by the following experimental data: R$_f$=0.56 (silica gel, hexanes/EtOAc, 4:1); $^1$H NMR (300 MHz, CDCl$_3$) δ 5.26 (t, J=6.3 Hz, 1H), 5.12 (m, 1H), 2.90 (t, J=7.1 Hz, 2H), 2.88-2.81 (m, 2H), 2.71-2.63 (m, 2H), 2.54 (d, J=7.0 Hz, 2H), 2.35 (t, J=7.3 Hz, 2H), 2.08-2.05 (m, 5H), 1.95-1.85 (m, 1H), 1.75 (d, J=2.7 Hz, 3H), 1.69 (s, 3H), 1.62 (s, 3H), 1.55 (s, 9H); $^{13}$C NMR (75 MHz, CDCl$_3$) δ 194.2, 160.3, 139.1, 131.7, 124.0, 117.8, 83.7, 52.6, 37.2, 34.4, 32.3, 32.1, 27.7, 26.4, 26.1, 25.7, 24.8, 23.6, 17.6; IR (CH$_2$Cl$_2$) 2977, 1719, 1160 cm$^{-1}$; LRMS (EI, 20 eV) m/z 412 (M$^+$, 3), 279 (19), 219 (55), 167 (45), 149 (100); HRMS (EI) calcd for C$_{22}$H$_{36}$O$_3$S$_2^+$ [M]$^+$ 412.2106, found 412.2112.

Preparation of Compounds 10a and 10b

Compound 10 can be prepared by ene cyclization of a preferred unsaturated α-keto ester, i.e., Compound 7. The ene cyclization can be catalyzed by an acid such as Lewis acids. One embodiment of such ene cyclization catalyzed by a Lewis acid is illustrated in Scheme 2, i.e., step g.

Intramolecular Carbonyl Ene Reaction Catalyzed with Cu(OTf)$_2$ and Ph-box

A mixture of (S,S)-Ph-box (0.22 equivalents) and copper triflate (Cu(OTf)$_2$, 0.2 equivalents) were mixed in CH$_2$Cl$_2$ for 0.5 hours at room temperature in the presence of activated 4 Å MS powder (500 mg per mmol substrate). Then Compound 7 in CH$_2$Cl$_2$ was added. The reaction contents were filtered through a thin pad of silica gel and then concentrated to give an analytically pure compound.

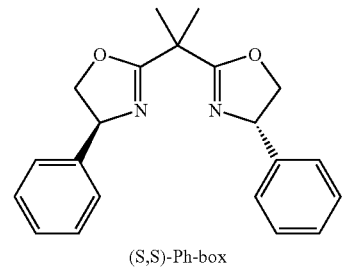

(S,S)-Ph-box

Intramolecular Carbonyl Ene Reaction Catalyzed with Cu(SbF$_6$)$_2$ and Ph-box

Preparation of Compound 10a

Compound 10a was prepared according to Step g of Scheme 2 which is described as follows. 0.22 Equivalents of (S,S)-Ph-box, 0.20 equivalents of CuCl$_2$ and 0.44 equivalents of AgSbF$_6$ were mixed in CH$_2$Cl$_2$ for 8 hours at room temperature, then filtered through cotton to the activated 4 Å MS powder (500 mg per mmol substrate). Then Compound 7a in $CH_2Cl_2$ was added. The reaction contents were filtered through a thin pad of silica gel and then concentrated to give an analytically pure compound.

Compound 10a was characterized by the following experimental data: $R_f$=0.35 (silica gel, hexane/EtOAc, 4:1); $[\alpha]_D^{23}$=−2.4° (c=0.50, $CH_2Cl_2$); $^1$H NMR (500 MHz, $CDCl_3$) δ 5.21 (t, J=7.2 Hz, 1H), 5.05-5.02 (m, 1H), 3.74 (s, 3H), 3.02 (s, 1H) 2.95-2.85 (m, 3H), 2.80-2.75 (m, 2H), 2.64 (t, J=6.9 Hz, 2H), 2.32 (dt, J=13.7, 4.2 Hz, 2.266 (t, J=13.2 Hz, 1H), 2.20-1.17 (m, 1H), 2.13-1.09 (m, 2H), 2.07-1.98 (m, 2H), 1.68 (d, J=1.2 Hz, 3H), 1.61 (s, 3H), 1.60 (s, 3H), 1.59-1.58 (m, 1H); $^{13}$C NMR (125 MHz, $CDCl_3$) δ 176.8, 133.8, 131.9, 127.9, 122.7, 76.5, 52.5, 49.8, 47.4, 37.3, 32.4, 31.8, 26.9, 26.3, 26.1, 25.6, 17.7, 15.5; IR ($CH_2Cl_2$) 3542 (br), 2936, 2877, 1732 cm$^{-1}$; LRMS (EI, 20 eV) m/z 370 (M$^+$, 5), 295 (15), 153 (100), 136 (91); HRMS (EI) calcd for $C_{19}H_{30}O_3S_2$ [M]$^+$ 370.1636, found 370.1640.

Preparation of Compound 10b

Compound 10b was prepared according to Step g of Scheme 2 which is described as follows. 0.22 Equivalents of (S,S)-Ph-box, 0.20 equivalents of $CuCl_2$ and 0.44 equivalents of $AgSbF_6$ were mixed in $CH_2Cl_2$ for 8 hours at room temperature, then filtered through cotton to the activated 4 Å MS powder (500 mg per mmol substrate). Then Compound 7b in $CH_2Cl_2$ was added. The reaction contents were filtered through a thin pad of silica gel and then concentrated to give an analytically pure compound.

Compound 10b was characterized by the following experimental data: $R_f$=0.58 (silica gel, hexanes/EtOAc, 4:1); $[\alpha]_D^{23}$=+12.6° (c=1.0, $CH_2Cl_2$, 96% ee); $^1$H NMR (400 MHz, $CDCl_3$) δ 5.28 (dt, J=2.8 Hz, 7.0 Hz, 1H), 5.05-5.04 (m, 1H), 3.14 (s, 1H), 2.92-2.87 (m, 1H), 2.87-2.79 (m, 2H), 2.78-2.75 (m, 2H), 2.65-2.64 (m, 2H), 2.28-2.20 (m, 2H), 2.14-1.97 (m, 6H), 1.67 (s, 3H), 1.65 (s, 3H), 1.60 (s, 3H), 1.45 (s, 9H); $^{13}$C NMR (100 MHz, $CDCl_3$) δ 175.6, 134.3, 131.5, 127.6, 122.9, 82.4, 76.2, 49.8, 47.0, 37.8, 32.7, 32.6, 28.0, 26.9, 26.3, 26.1, 25.6, 17.6, 15.1; IR ($CH_2Cl_2$) 3039, 1713, 1163, 1132 cm$^{-1}$; HRMS (EI) calcd for $C_{22}H_{36}O_3S_2^+$ [M$^+$] 412.2106, found 412.2106.

A preferred embodiment of the process of making 5-demethoxyfumagillol is illustrated in Scheme 3.

Preparation of Compound 11

Compound 11 was prepared according to Step h of Scheme 3 which is described as follows. To a suspension of 2 equivalents of $LiAlH_4$ in THF was added Compound 10 in THF slowly at 0° C. Following 30 minutes of stirring at 0° C., the reaction contents were diluted with $Et_2O$. Compound 11 was purified by flash column chromatography (99% yield). $R_f$=0.58 (silica gel, hexanes/EtOAc, 1:1).

Compound 11 was characterized by the following experimental data: $R_f$=0.58 (silica gel, hexanes/EtOAc, 1:1); $[\alpha]_D^{23}$=+5.7° (c=1.0, $CH_2Cl_2$); $^1$H NMR (300 MHz, $CDCl_3$) δ 5.30 (t, J=7.0 Hz, 1H), 5.08 (t, J=7.1 Hz, 1H), 3.55 (d, J=11.2 Hz, 1H), 3.30 (d, J=11.2 Hz, 1H), 2.90 (m, 2H), 2.76-2.70 (m, 4H), 2.49 (dd, J=12.9, 3.1 Hz, 1H), 2.16-2.00 (m, 8H), 1.76 (td, J=13.6, 4.7 Hz, 1H), 1.73 (s, 3H), 1.70 (s, 3H), 1.63 (s, 3H), 1.60 (m, 1H); $^{13}$C NMR (75 MHz, $CDCl_3$) δ 136.3, 132.0, 127.0, 122.2, 72.6, 69.7, 50.0, 47.3, 37.9, 32.6, 30.8, 26.8, 26.2, 26.0, 25.8, 25.6, 17.7, 16.4; IR ($CH_2Cl_2$) 3606, 3550, 2933, 1031 cm$^{-1}$; LRMS (EI, 20 eV) m/z 342 (M$^+$, 38), 324 (36), 273 (100), 195 (87), 145 (59); HRMS (EI) calcd for $C_{18}H_{28}O_2S_2^+$ [M$^+$−2H] 340.1531, found 340.1520.

Preparation of Compound 12

Compound 12 was prepared according to Step i of Scheme 3 which is described as follows. A solution of Compound 11 in $CH_2Cl_2$ was treated sequentially at 0° C. with 3 equivalents of DABCO and 2 equivalents of TsCl in small portions. The slurry so obtained was stirred for 30 minutes at 0° C. The tosyl mono-protected alcohol Compound 12 was purified by flash column chromatography (91% yield).

Compound 12 was characterized by the following experimental data: $R_f$=0.34 (silica gel, hexanes/EtOAc, 4:1); $[\alpha]_D^{23}$=+6.1° (c=1.0, $CH_2Cl_2$); $^1$H NMR (400 MHz, $CDCl_3$) δ 7.77 (d, J=8.3 Hz, 2H), 7.35 (d, J=8.3 Hz, 2H), 5.20 (td, J=6.9, 1.0 Hz, 1H), 5.02 (m, 1H), 3.87 (d, J=9.8 Hz, 1H), 3.74 (d, J=9.8 Hz, 1H), 2.91-2.85 (m, 2H), 2.74-2.70 (m, 2H), 2.65 (t, J=7.0 Hz, 2H), 2.48 (dd, J=12.9 Hz, 3.2 Hz, 1H), 2.45 (s, 3), 2.22 (t, J=13.3 Hz, 1H), 2.09-2.08 (m, 1H), 2.04-1.97 (m, 4H), 1.81 (td, J=18.2 Hz, 4.2 Hz, 1H), 1.75 (s, 1H), 1.69 (s, 3H), 1.64 (s, 3H), 1.61 (s, 3H), 1.60-1.58 (m, 1H); $^{13}$C NMR (100 MHz, $CDCl_3$) δ 144.9, 134.3, 132.6, 131.9, 129.8, 127.9, 127.8, 122.4, 75.8, 71.3, 49.7, 46.2, 37.6, 32.3, 30.8, 26.8, 26.3, 26.0, 25.8, 25.6, 21.6, 17.7, 16.2; IR ($CH_2Cl_2$) 3064, 1605, 1417, 1178 cm$^{-1}$; LRMS (EI, 20 eV) m/z 497 ([M+H]$^+$, 8), 253 (35), 172 (42), 145 (100), 107 (60); HRMS (EI) calcd for $C_{25}H_{36}O_4S_3$ [M$^+$]496.1776, found 496.1775.

Preparation of Compound 13

Compound 13 was prepared according to Step j of Scheme 3 which is described as follows. A solution of Compound 12 in $Et_2O$ was added quickly to a well-stirred solution of 4 equivalents of NCS and 4.5 equivalents of $AgNO_3$ in $CH_3CN$/$H_2O$ (4:1) at room temperature. The mixture was stirred for 1 minute and treated successively at 0.5-min intervals with saturated aqueous $Na_2SO_3$, saturated aqueous $Na_2CO_3$, and brine. The expected ketone 13 was purified by flash column chromatography (84% yield).

Compound 13 was characterized by the following experimental data: $R_f$=0.11 (silica gel, hexanes/EtOAc, 4:1); m.p.=42.5-44.0° C.; $[\alpha]_D^{23}$=−3.1° (c=1.0, $CH_2Cl_2$); $^1$H NMR (400 MHz, $CDCl_3$) δ 7.78 (d, J=8.3 Hz, 2H), 7.37 (d, J=8.3 Hz, 2H), 5.17 (td, J=7.0 Hz, 0.8 Hz, 1H), 5.00 (m, 1H), 4.00 (d, J=10.0 Hz, 1H), 3.79 (d, J=10.0 Hz, 1H), 2.96 (t, J=14.0 Hz, 1H), 2.67 (m, 1H), 2.65 (t, J=6.6 Hz, 2H), 2.46 (s, 3H), 2.42 (dd, J=13.9, 4.0 Hz, 1H), 2.34 (s, 1H), 2.25 (m, 1H), 2.10-2.04 (m, 2H), 1.70 (td, J=14.0, 5.0 Hz, 1H), 1.69 (s, 3H), 1.65 (s, 3H), 1.60 (s, 3H); $^{13}$C NMR (100 MHz, $CDCl_3$) δ 210.5, 145.2, 132.9, 132.4, 132.2, 129.9, 128.6, 127.9, 122.0, 75.2, 71.0, 51.4, 41.7, 36.1, 34.6, 26.8, 25.5, 21.6, 17.7, 14.5; IR ($CH_2Cl_2$) 3050, 1713, 1605, 1178 cm$^{-1}$; LRMS (EI, 20 eV) m/z 406 (M$^+$, 3), 337 (15), 165 (27), 155 (100), 120 (70); HRMS (EI) calcd for $C_{22}H_{30}O_5S^+$ 406.1814, found 406.1799.

Preparation of Compound 14

Compound 14 was prepared according to Step k of Scheme 3 which is described as follows. One equivalent of $Ti(OiPr)_4$ was added to a cold (−25° C.) solution of Compound 13 in $CH_2Cl_2$ containing 4 Å molecular sieves (500 mg/mmol). The mixture was stirred for 15 minutes and 2 equivalents of tBuOOH (5.5 M in decane) were added. The reaction was allowed to proceed for 12 hours and 2 equivalents of $Me_2S$ were added. Compound 14 was purified by flash column chromatography (91% yield). $R_f$=0.39 (silica gel, hexanes/EtOAc, 1:1).

Compound 14 was characterized by the following experimental data: $R_f$=0.39 (silica gel, hexanes/EtOAc, 1:1); m.p. 81.5-83.0° C.; $[\alpha]_D^{23}$=−3.4° (c=1.0, $CH_2Cl_2$, >99% ee); $^1$H NMR (300 MHz, $CDCl_3$) δ 7.80 (d, J=8.0 Hz, 2H), 7.38 (d, J=8.0 Hz, 2H), 5.11 (t, J=7.3 Hz, 1H), 4.14 (d, J=9.9 Hz, 1H), 4.08 (d, J=9.9 Hz, 1H), 2.94 (s, 1H) 2.80-2.70 (m, 2H), 2.68-2.58 (m, 1H), 2.47 (s, 3H), 2.33-2.20 (m, 3H), 2.20-2.05 (m, 1H), 1.90 (m, 1H), 1.84-1.78 (m, 2H), 1.77 (s, 3H), 1.64 (s, 3H), 1.34 (s, 3H); $^{13}$C NMR (75 MHz, $CDCl_3$) δ 209.2, 145.4, 135.5, 132.4, 130.1, 128.0, 117.6, 73.8, 71.4, 63.3, 61.9, 47.5, 39.3, 35.9, 34.7, 29.7, 27.4, 25.7, 21.7, 18.0; IR ($CH_2Cl_2$) 2929, 1754, 1722, 1600, 1365, 1190, 1178, 976 cm$^{-1}$; LRMS (EI, 20 eV) m/z 404 (M$^+$, 53), 335 (14), 250 (36), 219 (100), 163 (41), 109 (80); HRMS (EI) calcd for $C_{22}H_{28}O_5S^+$ [M$^+$−$H_2O$] 404.1657, found 404.1656.

Preparation of Compound 15

Compound 15 was prepared according to Step l of Scheme 3 which is described as follows. 2.2 equivalents of K-selectride® (1 M in THF) were added to a cold (−78° C.) solution of Compound 14 in THF. The mixture was stirred for 30 minutes. Compound 15 was purified by flash column chromatography (94% yield).

Compound 15 was characterized by the following experimental data: $R_f$=0.31 (silica gel, hexanes/EtOAc, 1:1); $[\alpha]_D^{23}$=−9.6° (c=1.0, $CH_2Cl_2$); $^1H$ NMR (400 MHz, $CDCl_3$) δ 5.18 (t, J=7.5 Hz, 1H), 4.31 (t, J=2.8 Hz, 1H), 2.87 (d, J=4.3 Hz, 1H), 2.71 (dd, J=7.2, 5.8 Hz, 1H), 2.53 (d, J=4.3 Hz, 1H), 2.41-2.38 (m, 1H), 2.24 (td, J=13.3, 4.9 Hz, 1H), 2.13-2.10 (m, 1H), 2.01-1.94 (m, 2H), 1.91-1.84 (m, 3H), 1.81-1.78 (m, 1H), 1.75 (s, 3H), 1.65 (s, 3H), 1.15 (s, 3H), 1.09 (dt, J=13.7, 3.2 Hz, 1H); $^{13}C$ NMR (100 MHz, $CDCl_3$) δ 134.9, 118.3, 65.5, 64.2, 60.5, 59.6, 51.1, 42.1, 33.1, 30.1, 29.1, 27.5, 25.7, 18.0, 13.6; IR ($CH_2Cl_2$) 3495, 2941, 1606, 1487, 1386, 1083, 984, 950 $cm^{-1}$; LRMS (EI, 20 eV) m/z 252 ($M^+$, 1), 165 (57), 153 (91), 135 (100), 111(81); HRMS (EI) calcd for $C_{15}H_{24}O_3^+$ $[M^+]$ 252.1725, found 252.1724.

In some embodiments, 5-demethoxyfumagillol derivatives can be prepared according to the scheme shown in Scheme 4.

Preparation of Compound 16

Compound 16 was prepared according to Step m of Scheme 4 which is described as follows. To a solution of p-nitrophenylchloroformate (60.5 mg, 0.30 mmol) in $CH_2Cl_2$ (2 mL) was added dry pyridine (32.5 μL, 0.40 mmol). Instantaneously a white precipitate was formed. A solution of Compound 15 (25.2 mg, 0.10 mmol) in $CH_2Cl_2$ (1 mL) was added dropwise. The mixture was stirred for 45 minutes at room temperature and then diluted with $Et_2O$ (30 mL). The resulting mixture was washed with water (3×10 mL) and brine, dried over anhydrous $Na_2SO_4$, filtered and concentrated under reduced pressure.

General Procedure for the Preparation of Compounds 17a-ac

Compounds 17a-ac were prepared according to Step n of Scheme 4 which is described as follows. The yellow residue from step [m] was dissolved in $CH_2Cl_2$ (2 mL), and the appropriate amine (0.11 mmol), DMAP (1.22 mg, 0.010 mmol), and triethylamine (21 μL, 0.15 mmol) was added at rt. After stirring for 3 hours at room temperature, the reaction was quenched with cold saturated aqueous solution of $NaHCO_3$ and extracted with $Et_2O$ (30 mL). The combined organic layers were washed with water and brine, dried over anhydrous $Na_2SO_4$, filtered and concentrated under reduced pressure. The yellow residue was purified by flash silica gel column chromatography to give one of Compounds 17a-ac.

Compounds 17a-ac were characterized by the following experimental data:

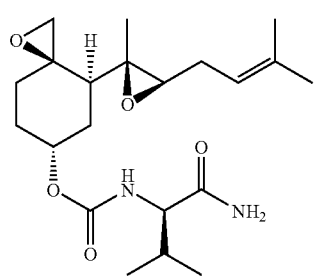

17a

Compound 17a was characterized by the following experimental data: colorless oil; $R_f$=0.34 (silica gel, $CH_2Cl_2$/EtOAc, 2:3); $[\alpha]_D^{23}$=−4.2° (c=2.0, $CHCl_3$); $^1H$ NMR (500 MHz, $CDCl_3$, 50° C.) δ 5.61 (br s, 1H), 5.45 (br s, 1H), 5.20-5.17 (m, 3H), 3.94 (br s, 1H), 2.87 (d, J=4.4 Hz, 1H), 2.73-2.69 (m, 1H), 2.51 (d, J=4.4 Hz, 1H), 2.39-2.33 (m, 1H), 2.18-2.07 (m, 4H), 1.98 (td, J=12.9, 2.6 Hz, 1H), 1.93-1.85 (m, 2H), 1.78 (dd, J=12.6, 3.8 Hz, 1H), 1.74 (s, 3H), 1.65 (s, 3H), 1.14-1.10 (m, 4H), 1.01 (d, J=6.8 Hz, 3H), 0.97 (d, J=6.9 Hz, 3H); $^{13}C$ NMR (125 MHz, $CDCl_3$) δ 173.5, 156.0, 135.0, 118.3, 69.9, 64.1, 60.2, 59.8, 59.2, 51.1, 43.1, 31.0, 30.3, 30.1, 29.7, 27.9, 25.7, 19.2, 18.0, 17.9, 13.5; IR ($CHCl_3$) 3432, 2969, 1691, 1522, 1217 $cm^{-1}$; LRMS (EI, 20 eV) m/z 350 (1), 235 (33), 136 (100); HRMS (EI) calcd for $C_{20}H_{32}NO_4$ $[M-CONH_2]^+$ 350.2331, found 350.2330.

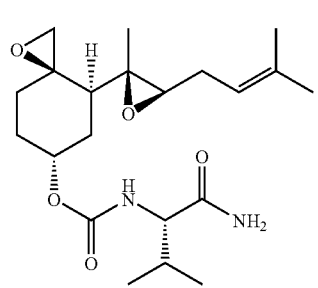

17b

Compound 17b was characterized by the following experimental data: colorless oil; $R_f$=0.31 (silica gel, $CH_2Cl_2$/EtOAc, 2:3); $[\alpha]_D^{23}$=−5.1° (c=1.5, $CDCl_3$); $^1H$ NMR (300 MHz, $CDCl_3$) δ 5.97 (br s, 1H), 5.55 (br s, 1H), 5.23-5.15 (m, 3H), 4.02-4.00 (m, 1H), 2.90 (d, J=4.3 Hz, 1H), 2.70 (t, J=6.0 Hz, 1H), 2.55 (d, J=4.3 Hz, 2.39-2.33 (m, 1H), 2.18-2.07 (m, 5H), 1.98-1.94 (m, 3H), 1.77-1.74 (m, 4H), 1.65 (s, 3H), 1.14-1.11 (m, 4H), 0.99 (d, J=6.8 Hz, 3H), 0.96 (d, J=6.8 Hz, 3H); $^{13}C$ NMR (125 MHz, $CDCl_3$) δ 173.4, 156.0, 135.0, 118.3, 70.0, 64.1, 60.2, 59.8, 59.2, 51.1, 43.1, 30.7, 30.3, 29.8, 27.9, 27.6, 25.7, 19.2, 18.0, 17.7, 13.5; IR ($CDCl_3$) 3416, 2980, 1692, 1504, 1216 $cm^{-1}$; LRMS (EI, 20 eV) m/z 350 (5), 235 (22), 136 (100); HRMS (EI) calcd for $C_{20}H_{32}NO_4$ $[M-CONH_2]^+$ 350.2331, found 350.2335.

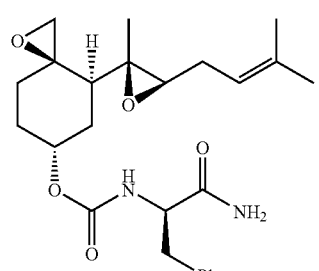

17c

Compound 17c was characterized by the following experimental data: colorless oil; $R_f$=0.44 (silica gel, $CH_2Cl_2$/EtOAc, 2:3); $[\alpha]_D^{23}$=−4.9° (c=2.7, $CDCl_3$); $^1H$ NMR (500 MHz, $CDCl_3$, 50° C.) δ 7.32-7.27 (m, 2H), 7.23-7.22 (m, 3H), 5.50 (br s, 2H), 5.21-5.16 (m, 3H), 4.33 (br s, 1H), 3.07-3.06 (m, 2H), 2.87 (d, J=4.4 Hz, 1H), 2.70 (t, J=6.1 Hz, 1H), 2.51 (d, J=4.4 Hz, 1H), 2.38-2.33 (m, 1H), 2.16-2.03 (m, 3H), 1.97 (td, J=13.5, 2.7 Hz, 1H), 1.90-1.88 (m, 2H), 1.75-1.72 (m, 4H), 1.66 (s, 3H), 1.13-1.10 (m, 4H); $^{13}C$ NMR (150 MHz, $CDCl_3$) δ 173.0, 155.4, 136.4, 135.0, 129.4, 128.8, 127.1, 118.3, 70.0, 64.1, 60.2, 59.2, 55.8, 51.1, 43.0, 38.6, 30.2, 29.7, 27.8, 27.6, 25.8, 18.0, 13.5; IR ($CDCl_3$) 3407, 2954, 1693, 1601, 1497, 1216 cm$^{-1}$; LRMS (EI, 20 eV) m/z 425 (39), 284 (50), 146 (100), 136 (100); HRMS (EI) calcd for C$_{25}$H$_{32}$NO$_4$ [M−H$_2$O]$^+$ 424.2362, found 424.2346

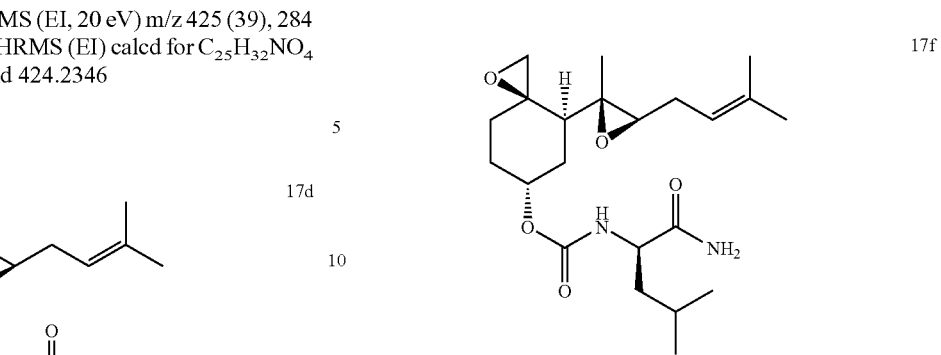

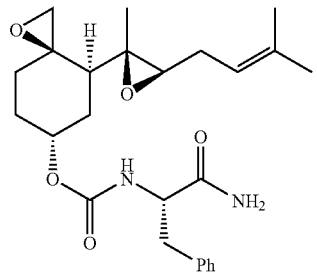

Compound 17d was characterized by the following experimental data: colorless oil; R$_f$=0.37 (silica gel, CH$_2$Cl$_2$/EtOAc, 2:3); [α]$_D^{23}$=−8.6° (c=0.60, CDCl$_3$); $^1$H NMR (300 MHz, CDCl$_3$) δ 7.31-7.21 (m, 5H), 5.76 (br s, 1H), 5.37 (br s, 1H), 5.19-5.15 (m, 3H), 4.46-4.40 (m, 1H), 3.10 (d, J=6.7 Hz, 2H), 2.89 (d, J=4.0 Hz, 1H), 2.68 (t, J=6.1 Hz, 1H), 2.54 (d, J=4.2 Hz, 1H), 2.40-2.35 (m, 1H), 2.16-2.04 (m, 4H), 2.01-1.88 (m, 3H), 1.75 (s, 4H), 1.65 (s, 3H), 1.13-1.08 (m, 4H); $^{13}$C NMR (125 MHz, CDCl$_3$) δ 173.0, 155.5, 136.5, 135.0, 129.3, 128.8, 127.1, 118.3, 70.1, 64.1, 60.2, 59.2, 55.7, 51.1, 43.0, 38.4, 30.2, 29.7, 27.8, 27.5, 25.7, 18.0, 13.4; IR (CDCl$_3$) 3403, 2946, 1693, 1605, 1500, 1223 cm$^{-1}$; LRMS (EI, 20 eV) m/z 398 (11), 301 (11), 235 (11), 146 (79), 136 (100); HRMS (EI) calcd for C$_{25}$H$_{32}$NO$_4$ [M−H$_2$O]$^+$ 398.2331, found 398.2334.

Compound 17f was characterized by the following experimental data: colorless oil; R$_f$=0.40 (silica gel, CH$_2$Cl$_2$/EtOAc, 2:3); [α]$_D^{23}$=−4.2° (c=2.1, CDCl$_3$); $^1$H NMR (500 MHz, CDCl$_3$, 50° C.) δ 5.94 (br s, 1H), 5.47 (br s, 1H), 5.20-5.17 (m, 2H), 5.01-4.98 (m, 1H), 4.13 (br s, 1H), 2.87 (d, J=4.4 Hz, 1H), 2.76-2.67 (m, 1H), 2.51 (d, J=4.4 Hz, 1H), 2.38-2.33 (m, 1H), 2.16-2.08 (m, 3H), 1.98 (td, J=13.6, 2.7 Hz, 1H), 1.92-1.85 (m, 2H), 1.78-1.67 (m, 5H), 1.65 (s, 3H), 1.55-1.48 (m, 1H), 1.15-1.11 (m, 4H), 0.96 (apparent t, J=6.3 Hz, 6H); $^{13}$C NMR (150 MHz, CDCl$_3$), two conformers δ 175.7, 174.8, 155.9, 155.5, 135.0, 118.2, 118.1, 70.7, 70.0, 64.1, 60.7, 60.2, 59.4, 59.2, 55.4, 52.8, 51.3, 51.1, 43.1, 42.4, 41.4, 41.2, 30.3, 30.1, 29.7, 27.9, 27.8, 27.5, 25.8, 24.8 (2), 24.7, 22.9, 22.1, 18.0, 13.4, 13.3; IR (CDCl$_3$) 3409, 2961, 1694, 1597, 1505, 1216 cm$^{-1}$; LRMS (EI, 20 eV) m/z 365 (6), 235 (21), 165 (21), 149 (100); HRMS (EI) calcd for C$_{21}$H$_{35}$NO$_4$ [M−CONH$_2$]$^+$ 365.2566, found 365.2511.

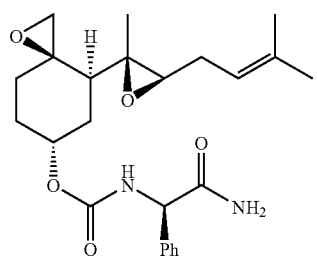

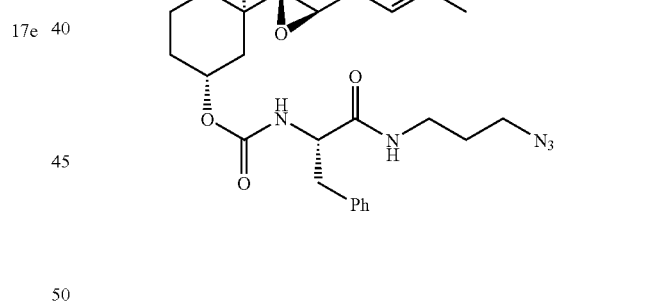

Compound 17e was characterized by the following experimental data: colorless oil; R$_f$=0.37 (silica gel, CH$_2$Cl$_2$/EtOAc, 2:3); [α]$_D^{23}$=−23.1° (c=1.8, CDCl$_3$); $^1$H NMR (500M, CDCl$_3$, 50° C.) δ 7.39-7.30 (m, 5H), 5.83 (br s, 1H), 5.49 (br s, 2H), 5.18 (t, J=7.5 Hz, 1H), 5.14 (br s, 2H), 2.85 (d, J=4.4 Hz, 1H), 2.69 (t, J=6.3 Hz, 1H), 2.48 (d, J=3.6 Hz, 1H), 2.37-2.32 (m, 1H), 2.16-2.10 (m, 1H), 2.06-1.87 (m, 5H), 1.75-1.74 (m, 4H), 1.65 (s, 3H), 1.12 (s, 3H), 1.10 (br s, 1H); $^{13}$C NMR (125 MHz, CDCl$_3$) δ 171.9, 155.2, 137.8, 135.0, 129.2, 128.7, 127.4, 118.3, 69.9, 64.1, 60.2, 59.2, 58.5, 51.1, 43.0, 30.3, 29.7, 27.8, 27.6, 25.7, 18.0, 13.4; IR (CDCl$_3$) 3416, 2954, 1698, 1605, 1496, 1047 cm$^{-1}$; LRMS (EI, 20 eV) m/z 384 (15), 235 (21), 176 (38), 136 (100); HRMS (EI) calcd for C$_{23}$H$_{30}$NO$_4$ [M−CONH$_2$]$^+$ 384.2175, found 384.2180.

Compound 17g was characterized by the following experimental data: colorless oil; R$_f$=0.40 (silica gel, CH$_2$Cl$_2$/EtOAc, 2:3); [α]$_D^{23}$=+9.1° (c=0.11, CH$_2$Cl$_2$); $^1$H NMR (300 MHz, CDCl$_3$) δ 7.34-7.18 (m, 5H), 5.86 (br s, 1H), 5.17-5.15 (m, 3H), 4.33-4.31 (m, 1H), 3.27-3.19 (m, 4H), 3.10 (dd, J=13.5, 6.3 Hz, 1H), 3.04 (dd, J=13.6, 7.7 Hz, 1H), 2.89 (d, J=4.3 Hz, 1H), 2.68 (t, J=6.5 Hz, 1H), 2.55 (d, J=4.3 Hz, 1H), 2.42-2.33 (m, 1H), 2.14-2.08 (m, 2H), 2.04-1.97 (m, 2H), 1.88-1.86 (m, 2H), 1.75 (s, 3H), 1.71 (dd, J=12.7, 3.76 Hz, 1H), 1.68-1.63 (m, 5H), 1.15-1.09 (m, 4H); $^{13}$C NMR (125 MHz, CDCl$_3$) δ 170.9, 155.4, 135.0, 129.3, 128.8, 127.1, 118.3, 70.1, 64.1, 60.2, 59.1, 56.4, 51.1, 49.0, 43.1, 38.7, 37.0, 30.2, 29.8, 28.5, 27.9, 27.6, 25.7, 18.0, 13.4; IR (CH$_2$Cl$_2$) 2930, 2861, 1724, 1670, 1606 cm$^{-1}$; LRMS (EI, 20 eV) m/z 497 (1), 235 (22), 165 (25), 137 (100); HRMS (EI) calcd for C$_{28}$H$_{39}$N$_3$O$_5$ [M−N$_2$]$^+$ 497.2889, found 497.2887.

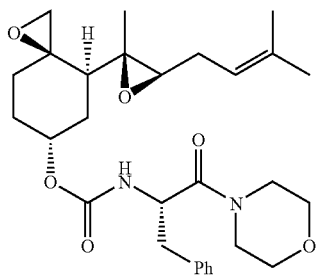

17h

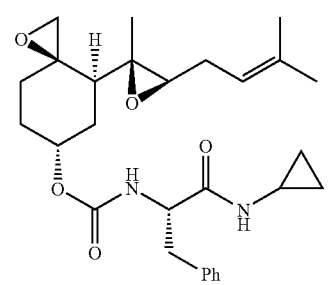

17j

Compound 17h was characterized by the following experimental data: colorless oil; $R_f$=0.37 (silica gel, hexanes/EtOAc, 1:2); $[\alpha]_D^{23}$=+30.0° (c=0.20, CH$_2$Cl$_2$); $^1$H NMR (400 MHz, CDCl$_3$) δ 7.31-7.19 (m, 5H), 5.59 (d, J=8.3 Hz, 1H), 5.20-5.14 (m, 2H), 4.83-4.80 (m, 1H), 3.63-3.41 (m, 5H), 3.31-3.23 (m, 1H), 3.06 (dd, J=14.8, 5.3 Hz, 1H), 2.94 (dd, J=12.9, 9.4 Hz, 1H), 2.90-2.84 (m, 3H), 2.68 (t, J=6.5 Hz, 1H), 2.55 (d, J=4.3 Hz, 1H), 2.42-2.33 (m, 1H), 2.13-2.09 (m, 3H), 1.99-1.88 (m, 3H), 1.75-1.72 (m, 4H), 1.65 (s, 3H), 1.13-1.10 (m, 4H); $^{13}$C NMR (125 MHz, CDCl$_3$) δ 169.9, 155.0, 136.2, 135.0, 129.6, 128.6, 127.2, 118.4, 69.6, 66.4, 66.0, 64.1, 60.2, 59.2, 51.2, 51.1, 46.0, 42.9, 42.3, 40.6, 30.2, 29.8, 28.0, 27.6, 25.7, 18.0, 13.5; IR (CH$_2$Cl$_2$) 2928, 2842, 1725, 1644, 1606 cm$^{-1}$; LRMS (EI, 20 eV) m/z 513 (10), 279 (14), 235 (32), 218 (100), 131(93); HRMS (EI) calcd for C$_{29}$H$_{40}$N$_2$O$_6$ [M]$^+$ 512.2886, found 512.2880.

Compound 17j was characterized by the following experimental data: colorless oil; $R_f$=0.37 (silica gel, hexanes/EtOAc, 1:2); $[\alpha]_D^{23}$=+9.5° (c=0.18, CH$_2$Cl$_2$); $^1$H NMR (300 MHz, CDCl$_3$) δ 7.31-7.17 (m, 5H), 5.69 (br s, 1H), 5.23-5.12 (m, 3H), 4.26-4.24 (m, 1H), 3.10 (dd, J=13.5, 6.3 Hz, 1H), 2.98 (dd, J=13.5, 7.9 Hz, 1H), 2.89 (d, J=4.3 Hz, 1H), 2.69 (t, J=6.3 Hz, 1H), 2.65-2.57 (m, 1H), 2.54 (d, J=4.3 Hz, 1H), 2.43-2.33 (m, 1H), 2.12-2.01 (m, 4H), 1.96-1.87 (m, 2H), 1.75-1.69 (m, 4H), 1.65 (s, 3H), 1.13-1.07 (m, 4H), 0.74-0.67 (m, 2H), 0.35-0.28 (m, 2H); $^{13}$C NMR (125 MHz, CDCl$_3$) δ 172.0, 155.4, 136.7 135.0, 129.3, 128.7, 127.0, 118.3, 69.9, 64.1, 60.1, 59.2, 56.2, 51.1, 43.0, 39.0, 30.2, 29.7, 27.9, 27.6, 25.7, 22.4, 18.0, 13.5, 6.5, 6.4; IR (CH$_2$Cl$_2$) 3434, 2969, 2915, 1725, 1684, 1603, 1496 cm$^{-1}$; LRMS (EI, 20 eV) m/z 483 (6), 235 (26), 187 (44), 137 (100); HRMS (EI) calcd for C$_{28}$H$_{38}$N$_2$O$_5$ [M]$^+$ 482.2780, found 482.2774.

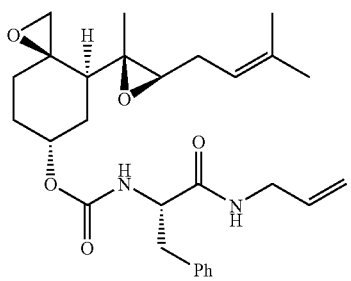

17i

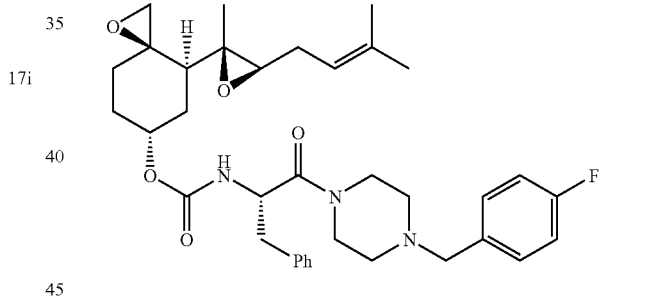

17k

Compound 17i was characterized by the following experimental data: colorless oil; $R_f$=0.50 (silica gel, hexanes/EtOAc, 1:2); $[\alpha]_D^{23}$=+2.2° (c=0.18, CH$_2$Cl$_2$); $^1$H NMR (300 MHz, CDCl$_3$) δ 7.32-7.18 (m, 5H), 5.81 (br s, 1H), 5.75-5.60 (m, 1H), 5.75-5.60 (m, 1H), 5.20-5.01 (m, 5H), 4.31-4.29 (m, 1H), 3.81 (t, J=5.7 Hz, 2H), 3.13-3.01 (m, 2H), 2.89 (d, J=4.3 Hz, 1H), 2.68 (t, J=6.6 Hz, 1H), 2.54 (d, J=4.3 Hz, 1H), 2.42-2.33 (m, 1H), 2.17-1.86 (m, 6), 1.75-1.68 (m, 4H), 1.65 (s, 3H), 1.13-1.07 (m, 4H); $^{13}$C NMR (100 MHz, CDCl$_3$) δ 170.5, 155.4, 136.6, 135.0, 133.5, 129.3, 128.7, 127.0, 118.3, 116.7, 70.0, 64.1, 60.1, 59.1, 56.4, 51.1, 43.0, 41.9, 38.8, 30.2, 29.7, 27.8, 27.5, 25.7, 18.0, 13.4; IR (CH$_2$Cl$_2$) 3440, 2929, 2861, 1719, 1679, 1606 cm$^{-1}$; LRMS (EI, 20 eV) m/z 483 (1), 235 (24), 205 (34), 131 (100); HRMS (EI) calcd for C$_{28}$H$_{38}$N$_2$O$_5$ [M]$^+$ 482.2781, found 482.2792.

Compound 17k was characterized by the following experimental data: colorless oil; $R_f$=0.32 (silica gel, hexanes/EtOAc, 1:2); $[\alpha]_D^{23}$=+27.5° (c=0.12, CH$_2$CL$_2$); $^1$H NMR (300 MHz, CDCl$_3$) δ 7.24-7.15 (m, 7H), 6.99 (t, J=8.6 Hz, 2H), 5.57 (d, J=8.2 Hz, 1H), 5.18 (t, J=5.9 Hz, 1H), 5.13 (br s, 1H), 4.87-4.79 (m, 1H), 3.62-3.48 (m, 2H), 3.37 (s, 2H), 3.32-3.27 (m, 1H), 3.02-2.95 (m, 3H), 2.89 (d, J=4.3 Hz, 1H), 2.67 (t, J=6.3 Hz, 1H), 2.54 (d, J=4.2 Hz, 1H), 2.42-2.33 (m, 2H), 2.24-2.22 (m, 2H), 2.16-1.99 (m, 3H), 1.95-1.80 (m, 4H), 1.75-1.71 (m, 4H), 1.65 (s, 3H), 1.13-1.08 (m, 4H); $^{13}$C NMR (125 MHz, CDCl$_3$) δ 169.5, 162.1 (d, $^1J_{C-F}$=243.8 Hz), 154.9, 136.3, 134.9, 133.3, 130.5 (d, $^3J_{C-F}$=7.9 Hz), 129.6, 128.5, 127.0, 118.4, 115.1 (d, $^2J_{C-F}$=21.1 Hz), 69.5, 64.0, 61.8, 60.1, 59.2, 52.4, 52.3, 51.3, 51.1, 45.6, 42.9, 42.0, 40.5, 30.2, 29.8, 28.0, 27.6, 25.7, 18.0, 13.5; IR (CH$_2$Cl$_2$) 2960, 1719, 1643, 1611 cm$^{-1}$; LRMS (EI, 20 eV) m/z 620 (4), 551 (14), 367 (14), 164 (56), 109 (100); HRMS (EI) calcd for C$_{36}$H$_{46}$FN$_3$O$_5$ [M]$^+$ 619.3421, found 619.3443.

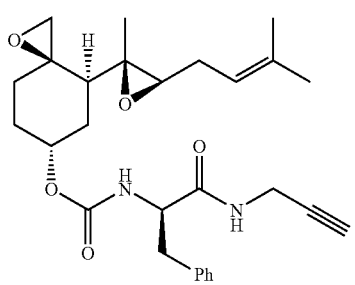

17l

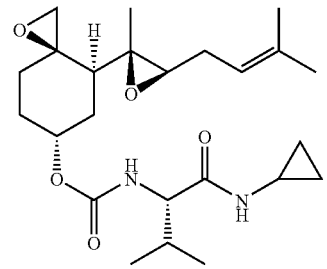

17n

Compound 17l was characterized by the following experimental data: colorless oil; $R_f$=0.29 (silica gel, hexanes/EtOAc, 1:1); $[\alpha]_D^{23}$=−12.2° (c=0.23, $CH_2Cl_2$); $^1$H NMR (400 MHz, $CDCl_3$) δ 7.33-7.20 (m, 5H), 5.88 (br s, 1H), 5.25-5.16 (m, 3H), 4.33 (br s, 1H), 3.96-3.92 (m, 2H), 3.16-3.00 (m, 2H), 2.89 (d, J=4.3 Hz, 1H), 2.69 (t, J=6.3 Hz, 1H), 2.54 (d, J=4.3 Hz, 1H), 2.43-2.33 (m, 1H), 2.18-2.04 (m, 4H), 1.94 (td, J=12.9, 2.6 Hz, 1H), 1.90-1.87 (m, 2H), 1.76-1.72 (m, 4H), 1.67 (s, 3H), 1.14-1.08 (m, 4H); $^{13}$C NMR (100 MHz, $CDCl_3$) δ 170.6, 155.4, 136.2, 135.0, 129.4, 128.8, 127.1, 118.3, 78.9, 71.7, 70.1, 64.1, 60.1, 59.1, 56.2, 51.1, 43.1, 38.7, 30.2, 29.7, 29.1, 27.8, 27.5, 25.7, 18.0, 13.4; IR ($CH_2Cl_2$) 3440, 3305, 2969, 2923, 1725, 1685, 1617 cm$^{-1}$; LRMS (EI, 20 eV) m/z 481 (1), 247 (17), 235 (33), 186 (56), 136 (100); HRMS (EI) calcd for $C_{28}H_{36}N_2O_5$ [M]$^+$ 480.2624, found 480.2639.

Compound 17n was characterized by the following experimental data: colorless oil; $R_f$=0.35 (silica gel, hexanes/EtOAc, 1:2); $[\alpha]_D^{23}$=−7.5° (c=0.24, $CH_2Cl_2$); $^1$H NMR (300 MHz, $CDCl_3$) δ 6.07 (br s, 1H), 5.21-5.15 (m, 3H), 3.84 (dd, J=8.6, 6.3 Hz, 1H), 2.90 (d, J=4.3 Hz, 1H), 2.73-2.69 (m, 2H), 2.55 (d, J=4.3 Hz, 1H), 2.41-2.37 (m, 1H), 2.16-2.10 (m, 4H), 2.01-1.89 (m, 3H), 1.77-1.75 (m, 4H), 1.66 (s, 3H), 1.14-1.11 (m, 4H), 0.96 (d, J=5.1 Hz, 3H), 0.93 (d, J=5.1 Hz, 3H), 0.81-0.76 (m, 2H), 0.53 (br s, 2H); $^{13}$C NMR (75 MHz, $CDCl_3$) δ 172.5, 156.0, 134.9, 118.3, 69.9, 64.0, 60.2, 60.1, 59.2, 51.1, 43.0, 31.0, 30.2, 29.7, 27.9, 27.5, 25.7, 22.6, 19.2, 18.0, 17.9, 13.5, 6.6; IR ($CH_2Cl_2$) 3434, 2956, 2923, 1719, 1678, 1603, 1502 cm$^{-1}$; LRMS (EI, 20 eV) m/z 435 (1), 307 (16), 182 (34), 140 (100); HRMS (EI) calcd for $C_{24}H_{38}N_2O_5$ [M]$^+$ 434.2781, found 434.2793.

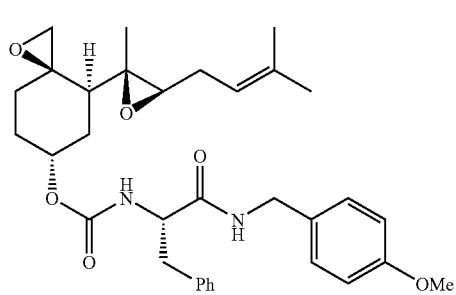

17m

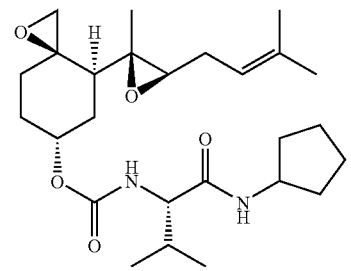

17o

Compound 17m was characterized by the following experimental data: colorless oil; $R_f$=0.53 (silica gel, hexanes/EtOAc, 1:2); $[\alpha]_D^{23}$=+24.2° (c=0.12, $CH_2Cl_2$); $^1$H NMR (300 MHz, $CDCl_3$) δ 7.26-7.15 (m, 5H), 7.04 (d, J=8.5 Hz, 2H), 6.82 (d, J=8.5 Hz, 2H), 5.90 (br s, 1H), 5.20-5.12 (m, 3H), 4.35-4.27 (m, 3H), 3.80-3.78 (m, 3H), 3.13 (dd, J=13.6, 6.4 Hz, 1H), 3.05 (dd, J=13.6, 7.6 Hz, 1H), 2.88 (d, J=4.3 Hz, 1H), 2.67 (t, J=6.4 Hz, 1H), 2.54 (d, J=4.3 Hz, 1H), 2.43-2.33 (m, 1H), 2.16-1.86 (m, 6H), 1.75 (s, 3H), 1.72-1.68 (m, 1H), 1.66 (s, 3H), 1.13-1.06 (m, 4H); $^{13}$C NMR (100 MHz, $CDCl_3$) δ 170.4, 159.0, 155.4, 136.6, 135.0, 129.6, 129.3, 129.2, 128.7, 127.0, 118.3, 114.0, 70.0, 64.1, 60.1, 59.1, 56.4, 55.3, 51.1, 43.1, 38.9, 30.2, 29.7, 27.8, 27.5, 25.7, 18.0, 13.4; IR ($CH_2Cl_2$) 3443, 2963, 2923, 1711, 1670, 1603 cm$^{-1}$; LRMS (EI, 20 eV) m/z 563 (1), 310 (47), 211 (24), 136 (56), 121 (100); HRMS (EI) calcd for $C_{33}H_{42}N_2O_6$ [M]$^+$ 562.3043, found 562.3042.

Compound 17o was characterized by the following experimental data: colorless oil; $R_f$=0.50 (silica gel, hexanes/EtOAc, 1:2); $[\alpha]_D^{23}$=−4.2° (c=0.31, $CH_2Cl_2$); $^1$H NMR (300 MHz, $CDCl_3$) δ 5.80 (br s, 1H), 5.25-5.16 (m, 3H), 4.20 (sext, J=6.9 Hz, 1H), 3.84 (dd, J=8.6, 6.3 Hz, 1H), 2.90 (d, J=4.3 Hz, 1H), 2.70 (t, J=6.8 Hz, 1H), 2.55 (d, J=4.3 Hz, 1H), 2.41-2.34 (m, 1H), 2.14-2.05 (m, 4H), 2.02-1.88 (m, 6H), 1.78-1.75 (m, 4H), 1.70-1.62 (m, 6H), 1.40-1.38 (m, 2H), 1.14-1.11 (m, 4H), 0.94 (d, J=7.9 Hz, 3H), 0.91 (d, J=6.9 Hz, 3H); $^{13}$C NMR (75 MHz, $CDCl_3$) δ 170.5, 162.4, 155.9, 134.9, 118.4, 69.8, 64.0, 60.5, 60.1, 59.2, 51.2, 51.1, 43.0, 33.1, 33.0, 31.1, 30.2, 29.8, 27.9, 27.6, 25.7, 23.7, 19.1, 18.0, 13.5; IR ($CH_2Cl_2$) 3399, 2965, 2861, 1715, 1672, 1597, 1500 cm$^{-1}$; LRMS (EI, 20 eV) m/z 463 (1), 235 (40), 143 (64), 137 (100); HRMS (EI) calcd for $C_{26}H_{42}N_2O_5$ [M]$^+$ 462.3094, found 462.3095.

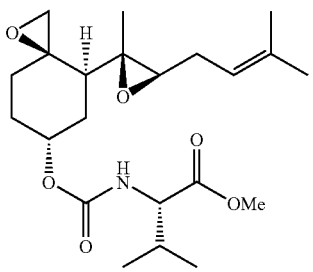

17p

Compound 17p was characterized by the following experimental data: colorless oil; $R_f$=0.39 (silica gel, hexanes/EtOAc, 2:1); $[\alpha]_D^{23}$=−4.7° (c=1.0, CHCl$_3$); $^1$H NMR (500 MHz, CDCl$_3$, 50° C.) δ 5.19 (t, J=7.4 Hz, 1H), 5.14 (br s, 1H), 5.07 (br s, 1H), 4.2 (br s, 1H), 3.73 (s, 3H), 2.88 (d, J=4.4 Hz, 1H), 2.69 (t, J=6.3 Hz, 1H), 2.51 (d, J=4.4 Hz, 1H), 2.38-2.32 (m, 1H), 2.16-2.04 (m, 4H), 2.03-1.86 (m, 3H), 1.76 (dd, J=12.3, 3.2 Hz, 1H), 1.74 (s, 3H), 1.65 (s, 3H), 1.17-1.10 (m, 4H), 0.95 (d, J=6.8 Hz, 3H), 0.91 (d, J=6.8 Hz, 3H); $^{13}$C NMR (125 MHz, CDCl$_3$) δ 172.5, 155.8, 134.9, 118.4, 69.8, 64.0, 60.2, 59.3, 58.9, 52.1, 51.1, 43.0, 31.4, 30.3, 29.7, 27.9, 27.6, 25.7, 18.9, 18.0, 17.7, 13.5; IR (CDCl$_3$) 3440, 2969, 2934, 1738, 1718, 1602, 1507 cm$^{-1}$; LRMS (EI, 20 eV) m/z 350 (2), 235 (14), 165 (23), 136 (100); HRMS (EI) calcd for C$_{20}$H$_{32}$NO$_4$ [M−COOMe]$^+$ 350.2331, found 350.2324.

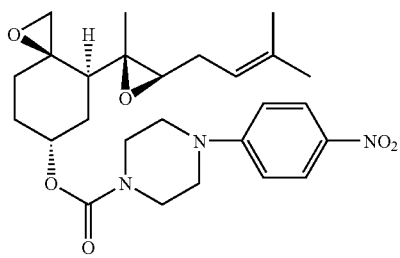

17q

Compound 17q was characterized by the following experimental data: yellow oil; $R_f$=0.53 (silica gel, hexanes/EtOAc, 1:2); $[\alpha]_D^{23}$=−14.5° (c=0.38, CH$_2$Cl$_2$); $^1$H NMR (300 MHz, CDCl$_3$) δ 8.14 (d, J=9.2 Hz, 2H), 6.82 (d, J=9.3 Hz, 2H), 5.25 (br s, 1H), 5.19 (t, J=7.2 Hz, 1H), 3.64 (br s, 4H), 3.44 (br s, 4H), 2.92 (d, J=4.3 Hz, 1H), 2.70 (t, J=6.4 Hz, 1H), 2.56 (d, J=4.3 Hz, 1H), 2.41-2.33 (m, 1H), 2.19-1.93 (m, 6H), 1.75-1.70 (m, 4H), 1.66 (s, 3H), 1.20-1.16 (m, 4H); $^{13}$C NMR (75 MHz, CDCl$_3$) δ 154.6, 154.5, 139.0, 135.0 125.9, 118.3, 112.9, 70.4, 64.1, 60.1, 59.1, 51.1, 46.8, 43.5, 43.0, 30.3, 29.9, 27.9, 27.5, 25.7, 18.0, 13.5; IR (CDCl$_3$) 2930, 2848, 1695, 1598, 1508 cm$^{-1}$; LRMS (EI, 20 eV) m/z 486 (14), 456 (39), 249 (79), 221 (100), 165 (77); HRMS (EI) calcd for C$_{26}$H$_{35}$N$_3$O$_6$ [M]$^+$ 485.2526, found 485.2540.

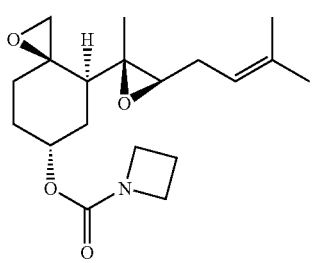

17r

Compound 17r was characterized by the following experimental data: colorless oil; $R_f$=0.14 (silica gel, Hexane/EtOAc, 2:1); $[\alpha]_D^{23}$=−24° (c=0.7, CH$_{CH2}$); $^1$H NMR (400 MHz, CDCl$_3$) δ 5.21-5.15 (m, 2H), 3.99 (t, J=3.65 Hz, 4H), 2.90 (d, J=4.4 Hz, 1H), 2.69 (t, J=6.4 Hz, 1H), 2.53 (d, J=4.4 Hz, 1H), 2.40-2.36 (m, 1H), 2.22 (q, J=7.6 Hz, 2H), 2.15-2.06 (m, 3H), 1.97 (td, J=12.7, 2.6 Hz, 1H), 1.91-1.87 (m, 2H), 1.75 (s, 3H), 1.72-1.70 (m, 1H), 1.66 (s, 3H), 1.15 (s, 3H), 1.11 (dt, J=13.7, 3.3 Hz, 1H); $^{13}$C NMR (100 MHz, CDCl$_3$) δ 155.8, 134.9, 118.4, 68.8, 64.0, 60.2, 59.2, 51.0, 49.1 (2 C), 43.1, 30.4, 29.7, 29.6, 28.0, 27.5, 25.7, 17.9, 15.6, 13.5; IR (CH$_2$Cl$_2$) υ$_{max}$ 2969, 2928, 1695, 1425 cm$^{-1}$.

17s

Compound 17s was characterized by the following experimental data: colorless oil; $R_f$=0.18 (silica gel, Hexane/EtOAc, 2:1); $[\alpha]_D^{23}$=−22° (c=0.8, CH$_2$Cl$_2$); $^1$H NMR (400 MHz, CDCl$_3$) δ 5.22-5.17 (m, 2H), 3.40-3.25 (m, 4H), 2.90 (d, J=4.4 Hz, 1H), 2.67 (t, J=6.4 Hz, 1H), 2.54 (d, J=4.4 Hz, 1H), 2.40-2.34 (m, 1H), 2.18-2.09 (m, 3H), 1.98 (td, J=12.9, 2.7 Hz, 1H), 1.92-1.85 (m, 5H), 1.79-1.76 (m, 1H), 1.75 (s, 3H), 1.65 (s, 3H), 1.15 (s, 3H), 1.11 (dt, J=13.7, 3.3 Hz, 1H); $^{13}$C NMR (100 MHz, CDCl$_3$) δ 154.3, 134.9, 118.4, 68.8, 64.0, 60.1, 59.2, 51.0, 45.9, 45.6, 43.3, 30.4, 29.9, 29.6, 28.0, 27.5, 25.7, 25.6, 24.9, 17.9, 13.5. IR (CH$_2$Cl$_2$) υ$_{max}$ 2982, 2959, 1686, 1425 cm$^{-1}$.

17t

Compound 17t was characterized by the following experimental data: colorless oil; $R_f$=0.30 (silica gel, Hexane/EtOAc, 2:1); $[\alpha]_D^{23}$=−23° (c=0.8, CH$_{Cl2}$); $^1$H NMR (400 MHz, CDCl$_3$) δ 5.21-5.17 (m, 2H), 3.38 (brs, 4H), 2.91 (d, J=4.5 Hz, 1H), 2.69 (dd, J=7.0, 5.9 Hz, 1H), 2.54 (d, J=4.5 Hz, 1H), 2.42-2.34 (m, 1H), 2.15-2.06 (m, 3H), 1.99 (td, J=12.7, 2.7 Hz, 1H), 1.95-1.88 (m, 2H), 1.75 (s, 3H), 1.74-1.65 (m, 1H), 1.65 (s, 3H), 1.59-1.52 (m, 2H), 1.52 (br, 4H), 1.15 (s, 3H), 1.14-1.11 (m, 1H); $^{13}$C NMR (100 MHz, CDCl$_3$) δ 154.7, 134.9, 118.4, 69.3, 63.9, 60.1, 59.2, 51.0, 44.7 (2 C), 43.4, 30.3, 29.9, 27.9, 27.5, 25.7, 25.5 (br, 2 C), 24.3, 17.9, 13.5. IR (CH$_2$Cl$_2$) υ$_{max}$ 2951, 2861, 1682, 1435 cm$^{-1}$.

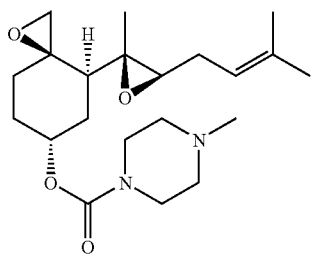

17u

Compound 17u was characterized by the following experimental data: colorless oil; $R_f$=0.11 (silica gel, CH$_2$Cl$_2$/EtOH, 20:1); $[\alpha]_D^{23}$=−20° (c=0.7, CH$_2$Cl$_2$); $^1$H NMR (400 MHz, CDCl$_3$) δ 5.21-5.17 (m, 2H), 3.49 (brs, 4H), 2.91 (d, J=4.4 Hz, 1H), 2.69 (t, J=6.3 Hz, 1H), 2.54 (d, J=4.4 Hz, 1H), 2.44-2.35 (br, 5H), 2.32 (s, 3H), 2.17-2.08 (m, 3H), 2.06-1.99 (m, 1H), 1.97-1.89 (m, 2H), 1.75 (s, 3H), 1.71 (dd, J=12.7, 3.9 Hz), 1.65 (s, 3H), 1.15 (s, 3H), 1.15-1.11 (m, 1H); $^{13}$C NMR (100 MHz, CDCl$_3$) δ 154.6, 134.9, 118.3 69.8, 64.0, 60.1, 59.1, 54.6 (2 C), 51.0, 46.1, 43.6 (br, 2 C), 43.4, 30.3, 29.9, 27.8, 27.5, 25.7, 17.9, 13.5. IR (CH$_2$Cl2) $\upsilon_{max}$ 2951, 2861, 2801, 1691, 1460, 1433 cm$^{-1}$.

17v

Compound 17v was characterized by the following experimental data: colorless oil; $R_f$=0.33 (silica gel, Hexane/EtOAc, 2:1); $[\alpha]_D^{23}$=−18° (c=0.6, CH$_{Cl2}$); $^1$H NMR (400 MHz, CDCl$_3$) δ 6.97 (td, J=8.7, 2.2 Hz, 2H), 6.89-6.86 (m, 2H), 5.23 (s, 1H), 5.18 (t, J=7.5 Hz, 1H), 3.61 (brs, 4H), 3.05 (brs, 4H), 2.91 (d, J=4.3 Hz, 1H), 2.70 (t, J=6.2 Hz, 1H), 2.55 (d, J=4.3 Hz, 1H), 2.40-2.35 (m, 1H), 2.18-1.92 (m, 6H), 1.75 (s, 3H), 1.72 (d, J=3.8 Hz, 0.5H), 1.66 (brs, 3.5H), 1.15 (brs, 4H); $^{13}$C NMR (100 MHz, CDCl$_3$), δ 157.5 (d, J=238 Hz, 1 C), 154.6, 147.8, 134.9, 118.6, 118.5, 118.3, 115.7, 115.5, 70.0, 64.0, 60.1, 59.1, 51.0, 50.4, 43.7 (2 C), 43.5, 30.3, 29.9, 27.8, 27.5, 25.7, 17.9, 13.5. IR (CH$_2$Cl$_2$) $\upsilon_{max}$ 2963, 2930, 2864, 1691, 1506, 1433 cm$^{-1}$.

17w

Compound 17w was characterized by the following experimental data: colorless oil; $R_f$=0.35 (silica gel, Hexane/EtOAc, 2:1); $[\alpha]_D^{23}$=−16° (c=0.9, CH$_{Cl2}$); $^1$H NMR (400 MHz, CDCl$_3$) δ 5.20-5.16 (m, 2H), 3.44 (brs, 4H), 2.90 (d, J=4.2 Hz, 1H), 2.68 (t, J=6.3 Hz, 1H), 2.54 (d, J=4.2 Hz, 1H), 2.39-2.35 (m, 1H), 2.33 (brs, 4H), 2.15-1.89 (m, 8H), 1.80-1.76 (m, 1H), 1.75 (s, 3H), 1.74-1.68 (m, 4H), 1.65 (s, 3H), 1.65-1.44 (m, 1H), 1.25-1.18 (m, 3H), 1.15 (s, 3H), 1.14-1.10 (m, 1H), 0.86 (q, J=10.9 Hz, 2H); $^{13}$C NMR (100 MHz, CDCl$_3$) δ 154.6, 134.9, 118.3, 69.5, 65.5, 63.9, 60.1, 59.1, 53.2 (br, 2 C), 51.0, 43.7 (br, 2 C), 43.3, 34.9, 30.3 (2 C), 27.8, 27.5, 25.7, 26.7, 26.0 (2 C), 25.7, 17.9, 13.5. IR (CH$_2$Cl$_2$) $\upsilon_{max}$ 2930, 2857, 1691, 1460, 1433 cm$^{-1}$.

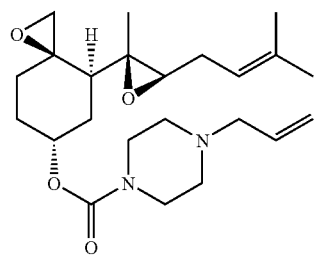

17x

Compound 17x was characterized by the following experimental data: colorless oil; $R_f$=0.16 (silica gel, Hexane/EtOAc, 1:3); $[\alpha]_D^{23}$=−20° (c=0.3, CH$_{Cl2}$); $^1$H NMR (400 MHz, CDCl$_3$) δ 5.89-5.82 (m, 1H), 5.23-5.16 (m, 4H), 3.48 (br s, 4H), 3.02 (d, J=6.5 Hz, 2H), 2.91 (d, J=4.3 Hz, 1H), 2.69 (t, J=6.1 Hz, 1H), 2.54 (d, J=4.3 Hz, 1H), 2.42-2.35 (m, 5H), 2.15-1.93 (m, 6H), 1.75 (s, 3H), 1.71 (dd, J=12.7, 3.9 Hz, 1H), 1.65 (s, 3H), 1.15 (s, 3H), 1.14-1.11 (m, 1H); $^{13}$C NMR (100 MHz, CDCl$_3$) δ 154.6, 134.9, 134.4 118.5, 118.3, 69.7, 64.0, 61.7, 60.1, 59.1, 52.6, 51.0, 43.7 (br, 2 C), 43.4, 30.3, 29.9, 29.6, 27.8, 27.5, 25.7, 17.9, 13.5. IR (CH$_2$Cl$_2$) $\upsilon_{max}$ 2928, 2863, 2807, 2365, 2328, 1690, 1458, 1433 cm$^{-1}$.

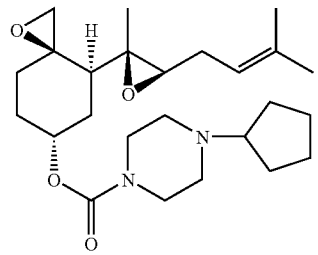

17y

Compound 17y was characterized by the following experimental data: colorless oil; $R_f$=0.13 (silica gel, Hexane/EtOAc, 1:3); $[\alpha]_D^{23}$=−17° (c=0.8,CH$_{C2}$); $^1$H NMR (400 MHz, CDCl$_3$) δ 5.20-5.16 (m, 2H), 3.49 (br s, 4H), 2.90 (d, J=4.2 Hz, 1H), 2.69 (t, J=6.4 Hz, 1H), 2.54 (d, J=4.2 Hz, 1H), 2.52-2.34 (m, 6H), 2.15-1.85 (m, 9H), 1.75 (s, 3H), 1.70-1.69 (m, 2H), 1.65 (s, 3H), 1.57-1.54 (m, 2H), 1.41-1.38 (m, 2H), 1.15 (s, 3H), 1.14-1.12 (m, 1H); $^{13}$C NMR (100 MHz, CDCl$_3$) δ 154.5, 134.9, 118.3, 69.7, 67.3, 64.0, 60.1, 59.1, 51.8, 51.0, 43.7 (br, 2 C), 43.3, 30.2 (3 C), 29.9, 27.9, 27.5, 25.7, 24.0 (2 C), 17.9, 13.4. IR (CH$_2$Cl$_2$) $\upsilon_{max}$ 2967, 2930, 2864, 2822, 1688, 1456, 1435 cm$^{-1}$.

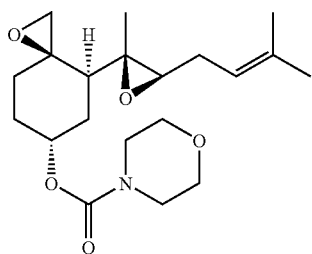

17z

Compound 17z was characterized by the following experimental data: colorless oil; $R_f$=0.12 (silica gel, Hexane/EtOAc, 2:1); $[\alpha]_D^{23}$=−22° (c=0.7, CH$_{Cl2}$); $^1$H NMR (400 MHz, CDCl$_3$) δ 5.22-5.16 (m, 2H), 3.65 (brs, 4H), 3.45 (brs, 4H), 2.91 (d, J=4.4 Hz, 1H), 2.69 (t, J=6.2 Hz, 1H), 2.55 (d, J=4.3 Hz, 1H), 2.40-2.36 (m, 1H), 2.16-2.10 (m, 2H), 2.06 (dd, J=14.4, 4.9 Hz, 1H), 1.99 (d, J=13.6 Hz, 1H), 1.95-1.90 (m, 2H), 1.75 (s, 3H), 1.70 (dd, J=12.8, 3.6 Hz, 2H), 1.66 (s, 3H), 1.17-1.12 (m, 4H); $^{13}$C NMR (100 MHz, CDCl$_3$) δ 154.7, 134.9, 118.3, 69.9, 66.5 (2 C), 64.0, 60.1, 59.1, 51.0, 45.0-44.5 (m, 2C), 43.4, 30.3, 29.9, 27.8, 27.5, 25.7, 17.9, 13.5; IR (CHCl$_3$) $\upsilon_{max}$ 2971, 2930, 2861, 1691, 1460, 1427, 1259 cm$^{-1}$; LRMS (EI, 20 eV) m/z 350 (1), 235 (33), 136 (100); HRMS (EI) calcd for C$_{20}$H$_{32}$NO$_4$ [M−CONH]$^+$ 350.2331, found 350.2330.

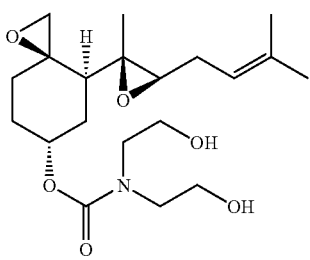

17aa

Compound 17aa was characterized by the following experimental data: colorless oil; $R_f$=0.39 (silica gel, EtOH/CH$_2$Cl$_2$, 1:9); $[\alpha]_D^{23}$=−10° (c=1.0, CH$_2$Cl$_2$); $^1$H NMR (400 MHz, CDCl$_3$) δ 5.22 (t, J=2.8 Hz, 1H), 5.16 (t, J=7.5 Hz, 1H), 3.84-3.75 (m, 4H), 3.48-3.42 (m, 4H), 2.90 (d, J=4.3 Hz, 1H), 2.69 (t, J=5.9 Hz, 1H), 2.55 (d, J=4.3 Hz, 1H), 2.42-2.36 (m, 1H), 2.18-1.90 (m, 6H), 1.75 (s, 3H), 1.70 (dd, J=12.8, 3.7 Hz, 1H), 1.65 (s, 3H), 1.18-1.15 (m, 1H), 1.14 (s, 3H); $^{13}$C NMR (100 MHz, CDCl$_3$) δ 156.3, 135.0, 118.1, 70.2, 64.2, 61.6, 61.4, 60.4, 59.1, 52.1 (2 C), 51.0, 43.4, 30.2, 30.0, 27.9, 27.5, 25.7, 17.9, 13.3; IR (CH$_2$Cl$_2$) $\upsilon_{max}$ 3697, 3606, 3444, 2946, 1690 cm$^{-1}$.

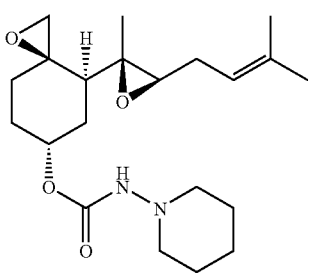

17ab

Compound 17ab was characterized by the following experimental data: colorless oil; $R_f$=0.35 (silica gel, Hexane/EtOAc, 2:1); $[\alpha]_D^{23}$=−22° (c=0.2, CH$_{Cl2}$); $^1$H NMR (400 MHz, CDCl$_3$) δ 5.20-5.16 (m, 2H), 3.38 (br s, 4H), 2.91 (d, J=4.3 Hz, 1H), 2.69 (dd, J=7.0, 5.9 Hz, 1H), 2.54 (d, J=4.3 Hz, 1H), 2.42-2.35 (m, 1H), 2.15-2.07 (m, 3H), 2.01 (dd, J=12.9, 2.7 Hz, 1H), 1.96-1.91 (m, 2H), 1.75 (s, 3H), 1.74-1.71 (m, 1H), 1.65 (s, 3H), 1.60-1.56 (m, 4H), 1.52 (br s, 4H), 1.15 (s, 3H), 1.14-1.10 (m, 1H); $^{13}$C NMR (100 MHz, CDCl$_3$) δ 154.7, 134.9, 118.4, 69.3, 64.0, 60.1, 59.2, 51.0, 44.7 (br, 2 C), 43.3, 30.3, 39.9, 29.6, 27.9, 27.5, 25.7, 25.5, 24.3, 17.9, 13.5. IR (CH$_2$Cl$_2$) $\upsilon_{max}$ 2932, 2861, 1688, 1433 cm$^{-1}$.

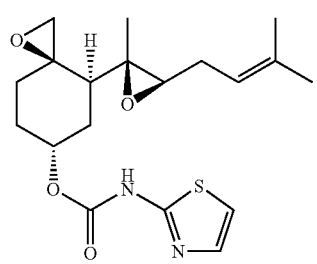

17ac

Compound 17ac was characterized by the following experimental data: colorless oil; $R_f$=0.21 (silica gel, Hexane/EtOAc, 2:1); $[\alpha]_D^{23}$=+16° (c=0.3, CH$_{Cl2}$); $^1$H NMR (400 MHz, CDCl$_3$) δ 12.1 (br s, 1H), 7.45 (d, J=3.6 Hz, 1H), 6.90 (d, J=3.6 Hz, 1H), 5.32 (s, 1H), 5.19 (t, J=7.4 Hz, 1H), 2.91 (d, J=4.3 Hz, 1H), 2.69 (t, J=6.4 Hz, 1H), 2.58 (d, J=4.3 Hz, 1H), 2.43-2.36 (m, 1H), 2.30-2.25 (m, 1H), 2.19-2.02 (m, 4H), 1.98-1.96 (m, 1H), 1.84 (dd, J=12.6, 3.4 Hz, 1H), 1.76 (s, 3H), 1.66 (s, 3H), 1.17 (s, 3H), 1.18-1.15 (m, 1H); $^{13}$C NMR (100 MHz, CDCl$_3$) δ 161.5, 153.3, 137.1, 135.0, 118.2, 112.5, 71.7, 64.0, 60.0, 59.0, 51.1, 43.1, 30.2, 29.6, 27.6, 27.5, 25.7, 18.0, 13.4. IR (CH$_2$Cl$_2$) $\upsilon_{max}$ 2971, 2932, 2857, 1724, 1543 cm$^{-1}$.

Procedure for Test of Anti-Angiogenesis Activity (A) BAEC Proliferation Assay

About 2500 bovine arotic endothelial cells (BAEC) in 195 µl of DMEM (Dulbecco's Modified Eagle's Medium) were plated per well of a 96-well plate and grown at 37° C. and 5% CO$_2$. Cells were allowed to recover for 12 hours. 1 µL of 200 times drug stock solution was added to each treatment well. The final vehicle (DMSO) concentration was 0.5%. Vehicle only was used as a control for maximum proliferation. Three wells were treated for each drug concentration. After 24 hours, 1 µCi of tritiated thymidine (diluted in DMEM to a total volume of 10 µL) was added to each well. After additional 6 hours incubation, each well was washed in 180 µl of PBS buffer. 70 µL of trypsin was added to each well. Plates were incubated for 5 minutes at 37° C. Cells were harvested using a Harvester 96 Mach III M (Tomtec) and transferred to glass fiber filters (Wallac). 6 mL of Betaplate Scint (PerkinElmer) was added to each filter in a sealed sample bag. Scintillation counting was done in using a 1450 MicroBeta counter (Wallac). CPM were normalized to vehicle control, averaged across three replicates, and fit to the following equation using GraphPadPrism v4.0: Y=Bottom+(Top-Bottom)/(1+10^((Log EC50−X)*HillSlope)) wherein X is the logarithm of concentration and Y is the response. Y started at Bottom and went to Top with a sigmoid shape. The bottom value was constrained to zero.

(B) MetAP-2 Enzymatic Assay

Recombinant human MetAP-2 was expressed and purified from insect cells as previously described (Li, X.; Chang, Y.-H. *Biochem. Biophys. Res. Commun.* 1996, 227, 152). To determine the effect of 5-demethoxyfumagillol as well as its derivatives on MetAP-2 activity, various amounts of these inhibitors was added to buffer H (10 mM HEPES, pH 7.35, 100 mM KCI, 10% glycerol, and 0.1 M $Co^{2+}$) containing 1 nM of purified human MetAP-2, and incubated at 37° C. for 30 minutes. To start the enzymatic reaction, Met-Gly-Met-Met was added to a concentration of 1 mM to the reaction mixture. Released methionine was quantified at different time points (0, 2, 3 and 5 min) using the method of Zuo et al (Zuo, S.; Guo, Q.; Ling, C.; Chang, Y-.H. *Mol. Gen. Genet.* 1995, 246, 247).

(C) Matrigel Plug Assay

Figure 2:
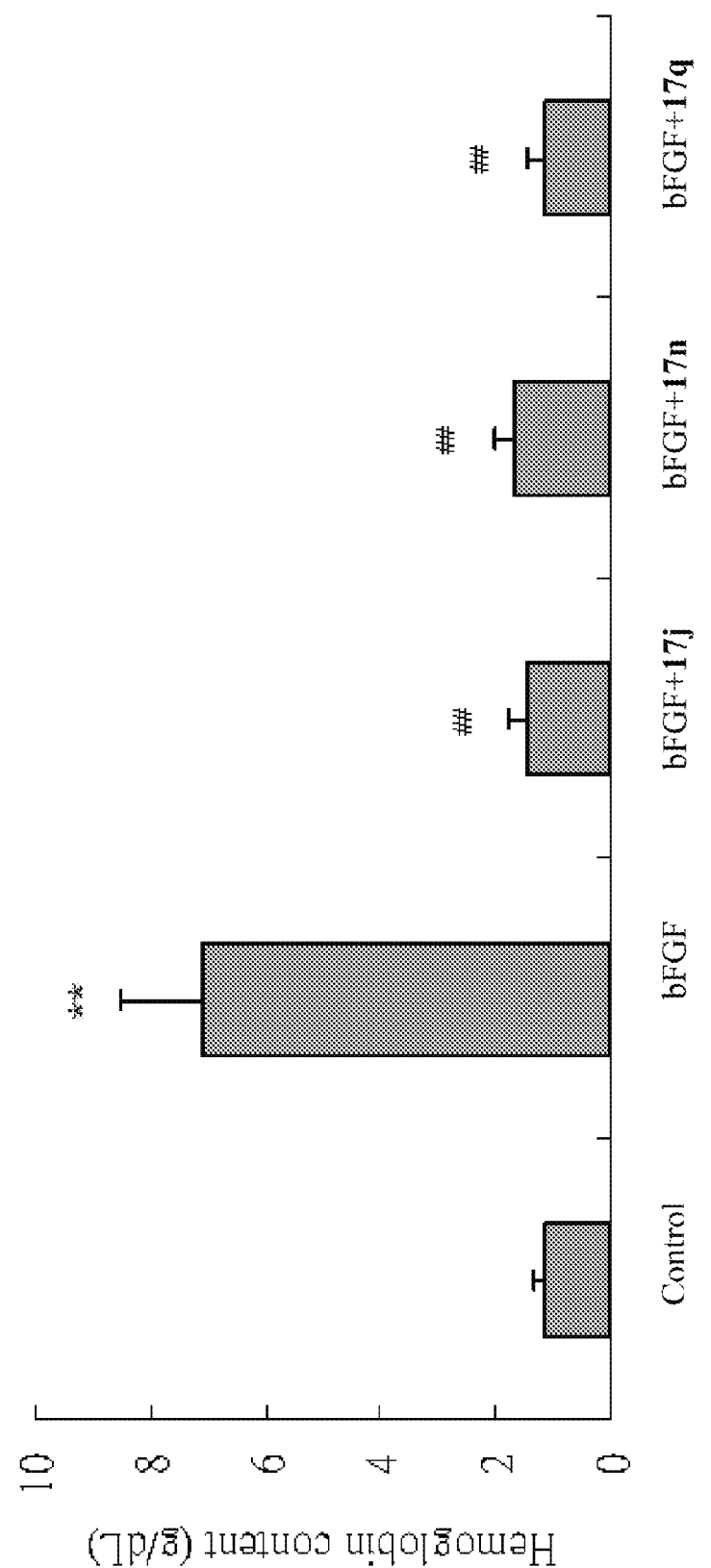
FIG. 2 depicts an analysis of hemoglobin contents in matrigel plugs taken from mice 10 days after injection of matrigel containing bFGF with or without Compound 17j, 17n or 17q.

Matrigel plug assay was used to determine the effects of fumagillol analogues on bFGF induced neovessel formation. C57 mice were injected subcutaneously into the abdomen with 0.2 mL of matrigel containing 300 ng bFGF. A control was performed by injecting matrigel alone. The injected matrigel formed solid gel plug. Fumagillol analogue 17j, 17n or 17q was administrated subcutaneously at a dose of 20 mg/kg/d in DMSO. Mice in control group were given subcutaneous injection of DMSO. Mice were sacrificed 10 days after injection of matrigel plug. The plugs were removed (FIG. 1) and the extent of neovascularization was assessed by measuring the hemoglobin content using the Drabkin's Reagent Kit (FIG. 2).

TABLE 1

Biological testing results of analogs of 5-demethoxyfumagillol

| Compound | MetAP-2 $IC_{50}$ (nM) | BAEC $IC_{50}$ (nM) |
|---|---|---|
| 5-Demethoxyfumagillol | 975 | 0.28 |
| Fumagillol | 909 | 2.04 |
| 17a | 29 | 0.21 |
| 17b | 50 | 0.11 |
| 17c | 16 | 0.039 |
| 17d | 56 | 0.067 |
| 17e | 42 | 0.085 |
| 17f | 39 | 0.092 |
| 17g | 41 | 1.41 |
| 17h | 44 | 0.079 |
| 17i | 47 | 0.059 |
| 17j | 41 | 0.027 |
| 17k | 12 | 0.21 |
| 17l | 21 | 0.051 |
| 17m | 11 | 0.19 |
| 17n | 19 | 0.031 |
| 17o | 28 | 0.035 |
| 17p | 27 | 0.062 |
| 17q | 26 | 0.020 |
| 17r |  | 0.038 |
| 17s |  | 0.040 |
| 17t |  | 0.081 |
| 17u |  | 0.089 |
| 17v |  | 0.068 |
| 17w |  | 0.074 |
| 17x |  | 0.047 |
| 17y |  | 0.031 |
| 17z |  | 0.048 |
| 17ab |  | 0.040 |
| 17ac |  | 0.038 |

As demonstrated above, embodiments disclosed herein provide various compounds that can be used for treating, managing or preventing a disease that is related to angiogenesis and other diseases disclosed herein. While this disclosure has been described with respect to a limited number of embodiments, the specific features of one embodiment should not be attributed to other embodiments disclosed herein. No single embodiment is representative of all aspects of this disclosure. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist. For example, the pharmaceutical compositions disclosed herein need not comprising only the compounds disclosed herein. It can comprise any type of compounds generally suitable for treating, managing or preventing a disease that is related to angiogenesis. It is noted that the methods for making and using the compounds disclosed herein are described with reference to a number of steps. These steps can be practiced in any sequence. One or more steps may be omitted or combined but still achieve substantially the same results. The appended claims intend to cover all such variations and modifications as falling within the scope of this disclosure.

All publications and patent applications mentioned in this specification are herein incorporated by reference to the same extent as if each individual publication or patent application was specifically and individually indicated to be incorporated by reference. It is to be understood that this disclosure has been described in detailed by way of illustration and example in order to acquaint others skilled in the art with the invention, its principles, and its practical application. Further, the specific embodiments provided herein as set forth are not intended to be exhaustive or to limit the disclosure, and that many alternatives, modifications, and variations will be apparent to those skilled in the art in light of the foregoing examples and detailed description. Accordingly, this disclosure is intended to embrace all such alternatives, modifications, and variations that fall within the spirit and scope of the following claims. While some of the examples and descriptions above include some conclusions about the way the compounds, compositions and methods may function, the inventors do not intend to be bound by those conclusions and functions, but put them forth only as possible explanations in light of current understanding.

What is claimed is:

1. A 5-demethoxyfumagillol derivative of Formula (XI):

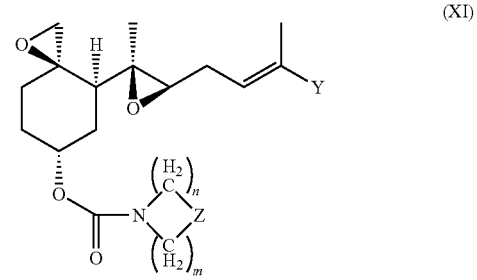

(XI)

or a pharmaceutically acceptable salt or stereoisomer thereof, wherein $R^{13}$ is hydrogen, or unsubstituted or substituted aryl, alkyl, cycloalkyl, alkenyl, alkynyl, arylalkyl, alkylaryl, heterocycloalkyl, heteroaryl, or —$(CH_2)_k$—$N_3$; Z is a bond, methylene, O, or $NR^{13}$; Y is —$CH_2$—$R^4$, —$CH_2$—$OR^5$, —C(=O)—$R^6$ or —C(=O)—$OR^7$; where each of $R^4$, $R^5$, $R^6$ and $R^7$ is independently H, alkyl, aryl, arylalkyl, alkylaryl, trialkylsilyl, methoxymethyl, dialkylamino, diarylamino or alkylarylamino; each of n and m is independently an integer from 0 to 5, wherein when Z is a bond, the sum of n and m is 5, when Z is methylene, O, or $NR^{13}$, the sum of n and m is 4; and k is an integer from 1 to 10.

2. The 5-demethoxyfumagillol derivative of claim 1, wherein the stereoisomer is an enantiomer of Formula (XI).

3. The 5-demethoxyfumagillol derivative of claim 1, wherein the stereoisomer is a diastereomer of Formula (XI).

4. The 5-demethoxyfumagillol derivative of claim 1 having one of the following structures:

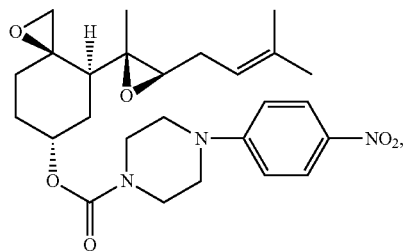
(17q)

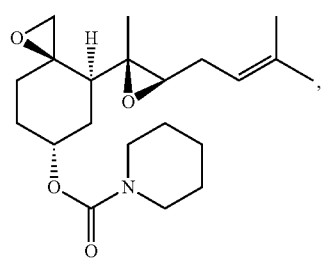
(17t)

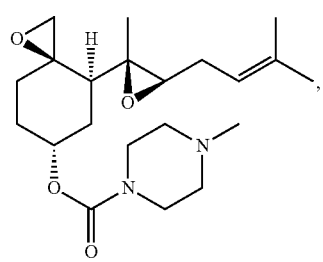
(17u)

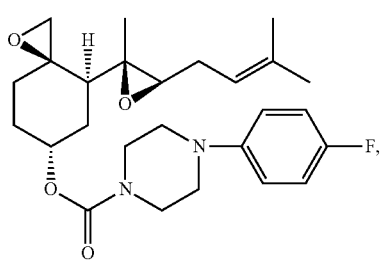
(17v)

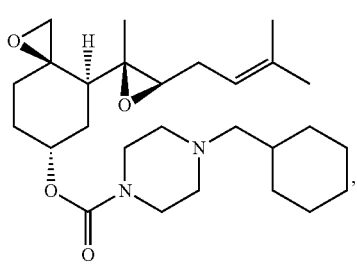
(17w)

-continued

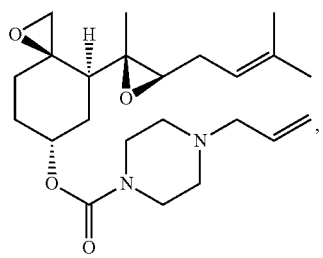
(17x)

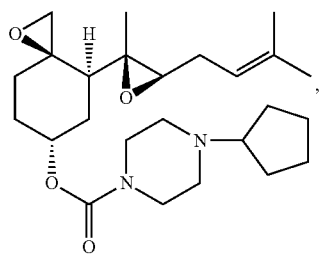
(17y)

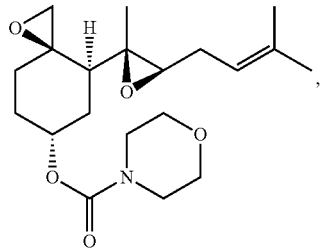
(17z)

or a stereoisomer thereof.

5. A process of making a 5-demethoxyfumagillol derivative having formula (XI) :

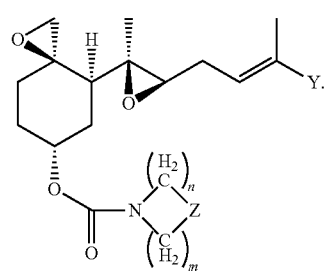
(XI)

or a stereoisomer thereof, wherein the process comprises the steps of:

(a) reacting a keto epoxide comprising Formula (VIII):

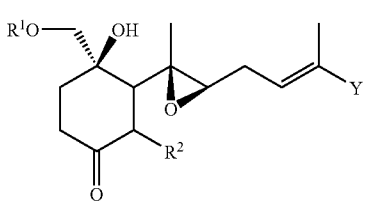
(VIII)

or a stereoisomer thereof, with a first base that is a tri-sec-butylborohydride salt to form 5-demethoxyfumagillol of Formula (XII):

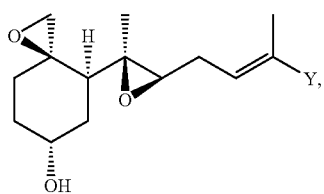

(XII)

or a stereoisomer thereof;
(b) contacting the 5-demethoxyfumagillol of Formula (XII) or a stereoisomer thereof with a phenylchloroformate in the presence of a second base to form an active intermediate of Formula (XIII),

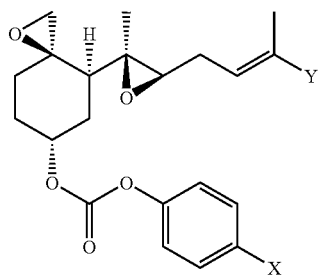

(XIII)

or a stereoisomer thereof; and
(c) reacting the active intermediate of Formula (XIII) with an amine of Formula (XV):

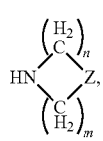

(XV)

or stereoisomer thereof in the presence of a third base, wherein $R^1$ is tosyl, mesyl, triflyl or nonflyl; $R^2$ is hydrogen or $OR^3$ where $R^3$ is H, alkyl, acyl, aryl, arylalkyl or alkylaryl; X is $NO_2$ or hydrogen; $R^{13}$ is hydrogen, or unsubstituted or substituted aryl, alkyl, cycloalkyl, alkenyl, alkynyl, arylalkyl, alkylaryl, heterocycloalkyl, heteroaryl, or —$(CH_2)_k$—$N_3$; Z is a bond, methylene, O, or $NR^{13}$; Y is —$CH_2$—$R^4$, —$CH_2$—$OR^5$, —C(=O)—$R^6$ or —C(=O)—$OR^7$ where each of $R^4$, $R^5$, $R^6$ and $R^7$ is independently H, alkyl, aryl, arylalkyl, alkylaryl, trialkylsilyl, methoxymethyl, dialkylamino, diarylamino or alkylarylamino; and each of n and m is independently an integer from 0 to 5 and wherein when Z is a bond, the sum of n and m is 5, when Z is methylene, O, or $NR^{13}$, the sum of n and m is 4; k is an integer from 1 to 10; and each of the second base and the third base is independently pyridine or triethylamine.

6. The process of claim 5, wherein the phenylchloroformate is unsubstituted phenylchloroformate or p-nitrophenylchloroformate.

7. A pharmaceutical composition, comprising a 5-demethoxyfumagillol derivative of claim 1, or a pharmaceutically acceptable salt, or stereoisomer thereof, and a pharmaceutically acceptable carrier.

8. The pharmaceutical composition of claim 7, further comprising at least an ingredient selected from the group consisting of excipients, moisturizers, diluents, metal stearates and combinations thereof.

9. The pharmaceutical composition of claim 7, which is in a single unit dosage form.

10. The pharmaceutical composition of claim 7, wherein the pharmaceutical composition further comprises a second chemotherapeutic drug.

11. The pharmaceutical composition of claim 10, wherein the second chemotherapeutic drug is selected from the group consisting of alkylating agents, anti-metabolites, plant alkaloids and terpenoids, vinca alkaloids, podophyllotoxins, taxanes, topoisomerase inhibitors, antitumour antibiotics, and monoclonal antibodies and combinations thereof.

12. The process of claim 5, wherein the first base is potassium tri-sec-butylborohydride.

* * * * *

UNITED STATES PATENT AND TRADEMARK OFFICE
CERTIFICATE OF CORRECTION

PATENT NO. : 8,299,067 B2
APPLICATION NO. : 12/410473
DATED : October 30, 2012
INVENTOR(S) : Dan Yang, Chengyong Li and Shiwu Chen It is certified that error appears in the above-identified patent and that said Letters Patent is hereby corrected as shown below:

Column 1,
Lines 32-33, "therapies generally involves" should read --therapies generally involve--.
Lines 37-38, "therapies generally involves" should read --therapies generally involve--.

Column 2,
Line 10, "was stymied" should read --were stymied--.

Column 10,
Line 28, "each of $R^4$, $R^6$," should read --each of $R^4$, $R^5$, $R^6$,--.

Column 14,
Lines 39-40, "disease develops" should read --disease which develops--.

Column 15,
Line 23, "compound disclosed herein" should read --compounds disclosed herein--.
Line 25, "compound comprises" should read --compound comprising--.

Column 16,
Lines 64-65, "can used" should read --can be used--.

Column 23,
Line 67, "slightly modification," should read --slight modification--.

Signed and Sealed this
Fifth Day of February, 2013

Teresa Stanek Rea
*Acting Director of the United States Patent and Trademark Office*

Column 24,
Scheme 3, Compound 14,
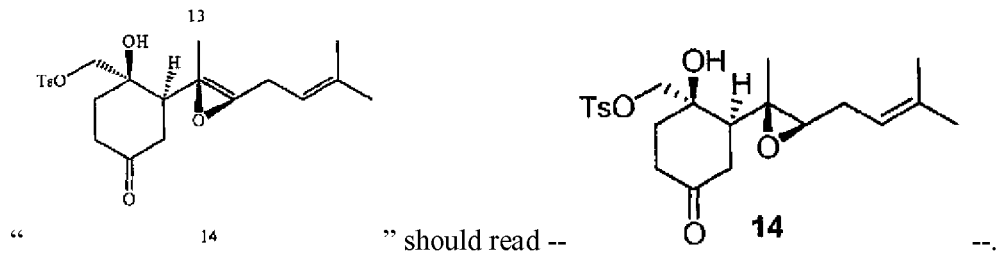
" 14 " should read -- 14 --.
Column 26,
Formula (XI),
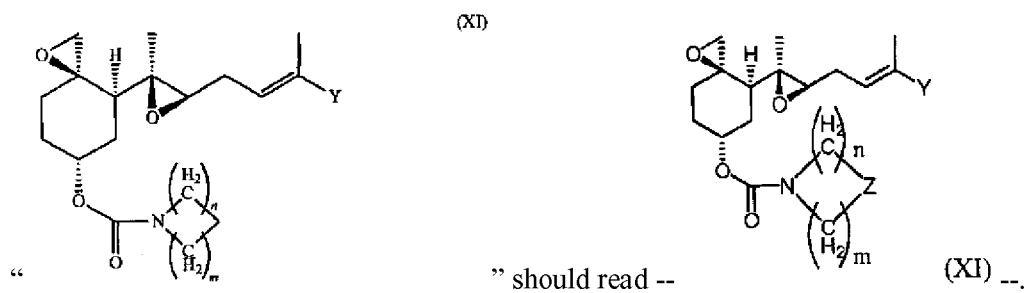
" " should read -- (XI) --.
Column 35,
Line 67, "and 17a-a." should read --and 17a-ac.--.
Column 36,
Line 1, "and serve to" should read --and serves to--.
Line 30, "(M+, 4)," should read --(M$^+$, 4),--.
Line 47, "3H 1.69" should read --3H), 1.69--.
Column 39,
Line 11, "4.2 Hz, 2.266," should read --4.2 Hz, 1H), 2.26--.
Column 40,
Line 9, "2.45 (s, 3)," should read --2.45 (s, 3H)--.
Column 42,
Line 33, "J=4.3 Hz, 2.39-2.33" should read --J = 4.3 Hz, 1H), 2.39-2.33--.
Column 45,
Line 60, "2.17-1.86 (m, 6)" should read --2.17-1.86 (m, 6H)--.

CERTIFICATE OF CORRECTION (continued)
U.S. Pat. No. 8,299,067 B2

Column 50,
Line 1, "c=0.7, $CH_{CH2}$," should read --c = 0.7, $CH_2Cl_2$--.
Line 57, "c=0.8, $CH_{Cl2}$" should read --c = 0.8, $CH_2Cl_2$--.

Column 51,
Line 42, "c=0.6, $CH_{Cl2}$" should read --c = 0.6, $CH_2Cl_2$--.

Column 52,
Line 3, "c=0.9, $CH_{Cl2}$" should read --c = 0.9, $CH_2Cl_2$--.
Line 31, "c=0.3, $CH_{Cl2}$" should read --c = 0.3, $CH_2Cl_2$--.
Line 57, "c=0.8,$CH_{C2}$" should read --c = 0.8, $CH_2Cl_2$--.

Column 53,
Line 15, "c=0.7, $CH_{Cl2}$" should read --c = 0.7, $CH_2Cl_2$--.
Line 27, "[M-CONH]$^+$" should read --[M – $CONH_2$]$^+$--.

Column 54,
Line 3, "c=0.2, $CH_{Cl2}$" should read --c = 0.2, $CH_2Cl_2$--.
Line 29, "c=0.3, $CH_{Cl2}$" should read --c = 0.3, $CH_2Cl_2$--.

Column 56,
Line 11, "need not comprising" should read --need not comprise--.
Line 26, "in detailed by" should read --in detail by--.